United States Patent
Kurn

(10) Patent No.: US 7,846,733 B2
(45) Date of Patent: *Dec. 7, 2010

(54) METHODS AND COMPOSITIONS FOR TRANSCRIPTION-BASED NUCLEIC ACID AMPLIFICATION

(75) Inventor: Nurith Kurn, Palo Alto, CA (US)

(73) Assignee: NuGen Technologies, Inc., San Carlos, CA (US)

(*) Notice: Subject to any disclaimer, the term of this patent is extended or adjusted under 35 U.S.C. 154(b) by 435 days.

This patent is subject to a terminal disclaimer.

(21) Appl. No.: 11/933,258

(22) Filed: Oct. 31, 2007

(65) Prior Publication Data

US 2008/0176311 A1    Jul. 24, 2008

Related U.S. Application Data

(60) Continuation of application No. 10/686,466, filed on Oct. 14, 2003, now Pat. No. 7,294,461, which is a division of application No. 09/893,191, filed on Jun. 26, 2001, now Pat. No. 6,686,156.

(60) Provisional application No. 60/277,748, filed on Mar. 21, 2001, provisional application No. 60/213,908, filed on Jun. 26, 2000.

(51) Int. Cl.
C07H 21/02 (2006.01)
C07H 21/04 (2006.01)
C12Q 1/68 (2006.01)

(52) U.S. Cl. ............ 435/975; 536/23.1; 536/24.3

(58) Field of Classification Search ............ None
See application file for complete search history.

(56) References Cited

U.S. PATENT DOCUMENTS

| | | | |
|---|---|---|---|
| 3,996,345 A | 12/1976 | Ullman et al. |
| 3,999,345 A | 12/1976 | McKelvey |
| 4,174,384 A | 11/1979 | Ullman et al. |
| 4,261,968 A | 4/1981 | Ullman et al. |
| 4,362,867 A | 12/1982 | Paddock |
| 4,458,066 A | 7/1984 | Caruthers et al. |
| 4,582,788 A | 4/1986 | Erlich |
| 4,683,194 A | 7/1987 | Saiki et al. |
| 4,786,600 A | 11/1988 | Kramer et al. |
| 4,876,187 A | 10/1989 | Duck et al. |
| 4,908,385 A | 3/1990 | Bar-Tana et al. |
| 4,996,143 A | 2/1991 | Heller et al. |
| 5,011,769 A | 4/1991 | Duck et al. |
| 5,043,272 A | 8/1991 | Hartley |
| 5,090,591 A | 2/1992 | Long |
| 5,106,727 A | 4/1992 | Hartley et al. |
| 5,130,238 A | 7/1992 | Malek et al. |
| 5,169,766 A | 12/1992 | Berninger et al. |
| 5,175,243 A | 12/1992 | Ash |
| 5,185,243 A | 2/1993 | Ullman et al. |
| 5,194,370 A | 3/1993 | Berninger et al. |
| 5,262,311 A | 11/1993 | Pardee et al. |
| 5,270,184 A | 12/1993 | Walker et al. |
| 5,328,985 A | 7/1994 | Sano et al. |
| 5,340,716 A | 8/1994 | Ullman et al. |
| 5,399,491 A | 3/1995 | Kacian et al. |
| 5,403,711 A | 4/1995 | Walder et al. |
| 5,409,818 A | 4/1995 | Davey et al. |
| 5,427,911 A | 6/1995 | Ruano |
| 5,427,929 A | 6/1995 | Richards et al. |
| 5,427,930 A | 6/1995 | Birkenmeyer et al. |
| 5,437,990 A | 8/1995 | Burg et al. |
| 5,455,166 A | 10/1995 | Walker |
| 5,480,784 A | 1/1996 | Kacian et al. |
| 5,491,063 A | 2/1996 | Fisher et al. |
| 5,508,178 A | 4/1996 | Rose et al. |
| 5,510,270 A | 4/1996 | Fodor et al. |
| 5,545,522 A | 8/1996 | Van Gelder et al. |
| 5,554,516 A | 9/1996 | Kacian et al. |

(Continued)

FOREIGN PATENT DOCUMENTS

EP        0050424        4/1982

(Continued)

OTHER PUBLICATIONS

Wang, S. et al., Nucl. Acids Res., vol. 23, pp. 1157-1164 (1995).*

(Continued)

*Primary Examiner*—Teresa E Strzelecka
(74) *Attorney, Agent, or Firm*—Wilson, Sonsini, Goodrich & Rosati

(57) ABSTRACT

Methods for isothermal exponential amplification of a target polynucleotide are disclosed. The methods employ two transcription modules, the first module providing linear amplification resulting in RNA transcripts, and a second module providing for further (generally cyclical) amplification resulting in more RNA transcripts. In one aspect, the amplification of the first module is composite primer based. In a second aspect, the amplification of the first module is based on target switching to generate a primer extension product comprising a promoter sequence. In all aspects, the RNA transcripts of the first transcription module are subjected to further amplification by creating an intermediate product comprising a double stranded promoter region from which transcription can occur. The invention further provides compositions and kits for practicing said methods, as well as methods which use the amplification results.

22 Claims, 15 Drawing Sheets

U.S. PATENT DOCUMENTS

| | | |
|---|---|---|
| 5,554,517 A | 9/1996 | Davey et al. |
| 5,556,752 A | 9/1996 | Lockhart et al. |
| 5,556,771 A * | 9/1996 | Shen et al. ................. 435/91.2 |
| 5,565,322 A | 10/1996 | Heller |
| 5,578,832 A | 11/1996 | Trulson et al. |
| 5,589,339 A | 12/1996 | Hampson et al. |
| 5,595,891 A | 1/1997 | Rose et al. |
| 5,616,478 A | 4/1997 | Chetverin et al. |
| 5,641,658 A | 6/1997 | Adams et al. |
| 5,648,211 A | 7/1997 | Fraiser et al. |
| 5,654,142 A | 8/1997 | Kievits et al. |
| 5,660,988 A | 8/1997 | Duck et al. |
| 5,665,539 A | 9/1997 | Sano et al. |
| 5,665,545 A | 9/1997 | Malek et al. |
| 5,665,845 A | 9/1997 | Allman |
| 5,679,512 A | 10/1997 | Laney et al. |
| 5,679,524 A | 10/1997 | Nikiforov et al. |
| 5,683,879 A | 11/1997 | Laney et al. |
| 5,686,272 A | 11/1997 | Marshall et al. |
| 5,688,648 A | 11/1997 | Mathies et al. |
| 5,693,502 A | 12/1997 | Gold et al. |
| 5,700,642 A | 12/1997 | Monforte et al. |
| 5,708,154 A | 1/1998 | Smith et al. |
| 5,709,994 A | 1/1998 | Pease et al. |
| 5,710,028 A | 1/1998 | Eyal et al. |
| 5,712,124 A | 1/1998 | Walker |
| 5,712,127 A | 1/1998 | Malek et al. |
| 5,716,785 A | 2/1998 | Van Gelder et al. |
| 5,731,146 A | 3/1998 | Duck et al. |
| 5,731,171 A | 3/1998 | Bohlander |
| 5,744,308 A | 4/1998 | Guillou-Bonnici et al. |
| 5,744,312 A | 4/1998 | Mamone et al. |
| 5,747,255 A | 5/1998 | Brenner |
| 5,763,178 A | 6/1998 | Chirikjian et al. |
| 5,766,846 A | 6/1998 | Schlossmacher et al. |
| 5,766,849 A | 6/1998 | McDonough et al. |
| 5,773,601 A | 6/1998 | Agrawal |
| 5,811,238 A | 9/1998 | Stemmer et al. |
| 5,824,517 A | 10/1998 | Cleuziat et al. |
| 5,824,518 A | 10/1998 | Kacian et al. |
| 5,829,547 A | 11/1998 | Fujii et al. |
| 5,830,655 A | 11/1998 | Monforte et al. |
| 5,830,721 A | 11/1998 | Stemmer et al. |
| 5,837,832 A * | 11/1998 | Chee et al. .................... 506/16 |
| 5,846,710 A | 12/1998 | Bajaj |
| 5,849,478 A | 12/1998 | Cashman |
| 5,849,542 A | 12/1998 | Reeve et al. |
| 5,849,547 A | 12/1998 | Cleuziat et al. |
| 5,854,033 A | 12/1998 | Lizardi et al. |
| 5,858,665 A | 1/1999 | Hepp et al. |
| 5,871,697 A | 2/1999 | Rothberg et al. |
| 5,876,976 A | 3/1999 | Richards et al. |
| 5,882,867 A | 3/1999 | Ullman et al. |
| 5,888,779 A | 3/1999 | Kacian et al. |
| 5,888,819 A | 3/1999 | Goelet et al. |
| 5,916,777 A | 6/1999 | Kacian et al. |
| 5,925,517 A | 7/1999 | Tyagi et al. |
| 5,932,449 A | 8/1999 | Emanuel et al. |
| 5,932,450 A | 8/1999 | Dattagupta et al. |
| 5,932,451 A | 8/1999 | Wang et al. |
| 5,958,681 A | 9/1999 | Wetmur et al. |
| 5,962,271 A | 10/1999 | Chenchik et al. |
| 5,962,272 A | 10/1999 | Chenchik et al. |
| 5,965,409 A | 10/1999 | Pardee et al. |
| 5,985,548 A | 11/1999 | Collier et al. |
| 6,004,744 A | 12/1999 | Goelet et al. |
| 6,004,745 A | 12/1999 | Arnold, Jr. et al. |
| 6,013,431 A | 1/2000 | Soderlund et al. |
| 6,027,889 A | 2/2000 | Barany et al. |
| 6,027,923 A | 2/2000 | Wallace |
| 6,030,774 A | 2/2000 | Laney et al. |
| 6,037,152 A | 3/2000 | Richards et al. |
| 6,040,138 A | 3/2000 | Lockhart et al. |
| 6,060,288 A | 5/2000 | Adams et al. |
| 6,083,689 A | 7/2000 | Martinelli et al. |
| 6,087,103 A | 7/2000 | Burmer |
| 6,090,591 A | 7/2000 | Burg et al. |
| 6,096,715 A | 8/2000 | Rossi et al. |
| 6,107,032 A | 8/2000 | Kilger et al. |
| 6,107,061 A | 8/2000 | Johnson |
| 6,124,120 A | 9/2000 | Lizardi |
| 6,132,997 A | 10/2000 | Shannon |
| 6,136,533 A | 10/2000 | Bekkaoui et al. |
| 6,140,086 A | 10/2000 | Fox et al. |
| 6,143,495 A | 11/2000 | Lizardi et al. |
| 6,159,685 A | 12/2000 | Pinkel et al. |
| 6,183,960 B1 | 2/2001 | Lizardi |
| 6,210,884 B1 | 4/2001 | Lizardi |
| 6,218,105 B1 | 4/2001 | Hall et al. |
| 6,218,151 B1 | 4/2001 | Cleuziat et al. |
| 6,251,600 B1 | 6/2001 | Winger et al. |
| 6,251,639 B1 | 6/2001 | Kurn |
| 6,255,060 B1 | 7/2001 | Eberwine et al. |
| 6,270,961 B1 | 8/2001 | Drmanac |
| 6,271,002 B1 | 8/2001 | Linsley et al. |
| 6,280,935 B1 | 8/2001 | Macevicz |
| 6,280,949 B1 | 8/2001 | Lizardi |
| 6,291,166 B1 | 9/2001 | Gerdes et al. |
| 6,291,170 B1 | 9/2001 | Van Gelder et al. |
| 6,300,073 B1 | 10/2001 | Zhao et al. |
| 6,306,365 B1 | 10/2001 | Ruoslahti et al. |
| 6,309,842 B1 | 10/2001 | Dower et al. |
| 6,309,843 B1 | 10/2001 | Timms |
| 6,316,229 B1 | 11/2001 | Lizardi et al. |
| 6,319,714 B1 | 11/2001 | Crameri et al. |
| 6,326,142 B1 | 12/2001 | Royer |
| 6,335,160 B1 | 1/2002 | Patten et al. |
| 6,344,356 B1 | 2/2002 | Stemmer |
| 6,358,712 B1 | 3/2002 | Jarrell et al. |
| 6,365,375 B1 | 4/2002 | Dietmaier et al. |
| 6,410,278 B1 | 6/2002 | Notomi et al. |
| 6,485,944 B1 | 11/2002 | Church et al. |
| 6,617,137 B2 | 9/2003 | Dean et al. |
| 6,673,549 B1 | 1/2004 | Furness et al. |
| 6,686,156 B2 | 2/2004 | Kurn |
| 6,692,918 B2 | 2/2004 | Kurn |
| 6,794,138 B1 | 9/2004 | Cao et al. |
| 6,815,164 B2 | 11/2004 | Kurn |
| 6,858,413 B2 | 2/2005 | Kurn |
| 6,927,024 B2 | 8/2005 | Dodge et al. |
| 6,946,251 B2 | 9/2005 | Kurn |
| 6,949,633 B1 | 9/2005 | Monforte et al. |
| 6,951,722 B2 | 10/2005 | Mukai et al. |
| 7,056,671 B2 | 6/2006 | Enoki et al. |
| 7,094,536 B2 | 8/2006 | Kurn |
| 7,176,025 B2 | 2/2007 | Kurn |
| 7,294,461 B2 | 11/2007 | Kurn |
| 7,351,557 B2 | 4/2008 | Kurn |
| 7,354,717 B2 | 4/2008 | Kurn |
| 7,402,386 B2 | 7/2008 | Kurn et al. |
| 7,534,569 B2 | 5/2009 | Chang et al. |
| 2001/0000077 A1 | 3/2001 | Engelhardt et al. |
| 2001/0034048 A1 | 10/2001 | Kurn |
| 2001/0041334 A1 | 11/2001 | Rashtchian et al. |
| 2002/0028447 A1 | 3/2002 | Lee et al. |
| 2002/0058270 A1 | 5/2002 | Kurn |
| 2002/0064837 A1 | 5/2002 | Trinh et al. |
| 2002/0115088 A1 | 8/2002 | Kurn |
| 2002/0127575 A1 | 9/2002 | Hoke et al. |
| 2002/0142309 A1 | 10/2002 | Dattagupta |
| 2002/0164628 A1 | 11/2002 | Kurn |
| 2002/0177141 A1 | 11/2002 | Chee et al. |
| 2003/0017591 A1 | 1/2003 | Kurn |
| 2003/0049657 A1 | 3/2003 | Cherry |

| | | | |
|---|---|---|---|
| 2003/0073081 A1 | 4/2003 | Mukai et al. | |
| 2003/0087251 A1 | 5/2003 | Kurn | |
| 2003/0104460 A1 | 6/2003 | Rabbani et al. | |
| 2003/0186234 A1 | 10/2003 | Kurn | |
| 2003/0204331 A1 | 10/2003 | Whitney et al. | |
| 2003/0215926 A1 | 11/2003 | Kurn et al. | |
| 2004/0005614 A1 | 1/2004 | Kurn et al. | |
| 2004/0023271 A1 | 2/2004 | Kurn et al. | |
| 2004/0033499 A1 | 2/2004 | Ilsley | |
| 2004/0096853 A1 | 5/2004 | Mayer | |
| 2004/0203019 A1 | 10/2004 | Kurn et al. | |
| 2004/0203025 A1 | 10/2004 | Kurn | |
| 2005/0003441 A1 | 1/2005 | Kurn | |
| 2005/0014192 A1 | 1/2005 | Kurn | |
| 2005/0019793 A1 | 1/2005 | Kurn et al. | |
| 2005/0064456 A1 | 3/2005 | Kurn | |
| 2005/0079510 A1 | 4/2005 | Berka et al. | |
| 2005/0123950 A1 | 6/2005 | Mukai et al. | |
| 2005/0130173 A1 | 6/2005 | Leamon et al. | |
| 2005/0208538 A1 | 9/2005 | Kurn et al. | |
| 2006/0008824 A1 | 1/2006 | Ronaghi et al. | |
| 2006/0014182 A1 | 1/2006 | Kurn | |
| 2006/0246434 A1 | 11/2006 | Erlander et al. | |
| 2006/0269934 A1 | 11/2006 | Woudenberg et al. | |
| 2007/0054301 A1 | 3/2007 | Becker et al. | |
| 2008/0182300 A1 | 7/2008 | Kurn | |
| 2009/0036663 A1 | 2/2009 | Kurn | |
| 2009/0068709 A1 | 3/2009 | Kurn et al. | |
| 2009/0130721 A1 | 5/2009 | Kurn et al. | |
| 2009/0203085 A1 | 8/2009 | Kurn et al. | |
| 2009/0203531 A1 | 8/2009 | Kurn et al. | |
| 2009/0233804 A1 | 9/2009 | Kurn et al. | |
| 2009/0239232 A1 | 9/2009 | Kurn et al. | |
| 2009/0275486 A1 | 11/2009 | Kurn et al. | |
| 2010/0022403 A1 | 1/2010 | Kurn et al. | |

FOREIGN PATENT DOCUMENTS

| | | | |
|---|---|---|---|
| EP | 0084796 | | 8/1983 |
| EP | 0201184 | | 11/1986 |
| EP | 0237362 | | 9/1987 |
| EP | 0258017 | | 3/1988 |
| EP | 0320308 | | 6/1989 |
| EP | 0365627 | | 5/1990 |
| EP | 0395398 | | 10/1990 |
| EP | 0497272 | | 8/1992 |
| EP | 0500224 | | 8/1992 |
| EP | 0505012 | | 9/1992 |
| EP | 0543612 | | 5/1993 |
| EP | 0329822 | B1 | 6/1994 |
| EP | 0667393 | | 8/1995 |
| EP | 0497271 | B1 | 10/1996 |
| EP | 0878553 | | 11/1998 |
| EP | 0971039 | | 1/2000 |
| EP | 1055736 | A1 | 11/2000 |
| EP | 1167524 | A1 | 1/2002 |
| EP | 1273737 | A2 | 1/2003 |
| EP | 1275737 | A2 | 1/2003 |
| EP | 1281757 | A1 | 2/2003 |
| EP | 1312682 | A1 | 5/2003 |
| JP | 6327500 | A | 11/1994 |
| JP | 07-023799 | A2 | 1/1995 |
| WO | WO 88/02746 | A1 | 4/1988 |
| WO | WO 88/10315 | A1 | 12/1988 |
| WO | WO 89/01050 | A1 | 2/1989 |
| WO | WO 90/01069 | A1 | 2/1990 |
| WO | WO 92/15712 | A1 | 9/1992 |
| WO | WO 92/18521 | A1 | 10/1992 |
| WO | WO 93/15229 | A2 | 8/1993 |
| WO | WO 95/03426 | A2 | 2/1995 |
| WO | WO 93/15229 | A3 | 3/1995 |
| WO | WO 95/03426 | A3 | 6/1995 |
| WO | WO 95/21271 | A1 | 8/1995 |
| WO | WO 97/03207 | A1 | 1/1997 |
| WO | WO 97/04123 | A1 | 2/1997 |
| WO | WO 97/04126 | A1 | 2/1997 |
| WO | WO 97/32040 | A2 | 9/1997 |
| WO | WO 97/32040 | A3 | 10/1997 |
| WO | WO 98/01050 | A1 | 1/1998 |
| WO | WO 98/06736 | A1 | 2/1998 |
| WO | WO 98/28443 | A1 | 7/1998 |
| WO | WO 98/44151 | A1 | 10/1998 |
| WO | WO 98/59066 | A1 | 12/1998 |
| WO | WO 99/18241 | A1 | 4/1999 |
| WO | WO 99/23256 | A1 | 5/1999 |
| WO | WO 99/25873 | A1 | 5/1999 |
| WO | WO 99/29901 | A1 | 6/1999 |
| WO | WO 99/37808 | A1 | 7/1999 |
| WO | WO 99/40219 | A1 | 8/1999 |
| WO | WO 99/42618 | A1 | 8/1999 |
| WO | WO 99/55912 | A1 | 11/1999 |
| WO | WO 00/08208 | A2 | 2/2000 |
| WO | WO 00/09745 | A1 | 2/2000 |
| WO | WO 00/08208 | A3 | 5/2000 |
| WO | WO 00/28082 | A1 | 5/2000 |
| WO | WO 00/40715 | A2 | 7/2000 |
| WO | WO 00/52191 | A1 | 9/2000 |
| WO | WO 00/56877 | A1 | 9/2000 |
| WO | WO 00/56925 | A2 | 9/2000 |
| WO | WO 00/56925 | A3 | 9/2000 |
| WO | WO 00/70095 | A2 | 11/2000 |
| WO | WO 00/40715 | A3 | 2/2001 |
| WO | WO 01/20035 | A2 | 3/2001 |
| WO | WO 01/20035 | A3 | 3/2001 |
| WO | WO 01/23613 | A1 | 4/2001 |
| WO | WO 00/70095 | A3 | 8/2001 |
| WO | WO 01/64952 | A2 | 9/2001 |
| WO | WO 01/73134 | A2 | 10/2001 |
| WO | WO 01/20035 | A3 | 12/2001 |
| WO | WO 02/00938 | A2 | 1/2002 |
| WO | WO 02/06533 | A2 | 1/2002 |
| WO | WO 00/56925 | A3 | 4/2002 |
| WO | WO 02/28876 | A2 | 4/2002 |
| WO | WO 02/29117 | A2 | 4/2002 |
| WO | WO 02/48402 | A2 | 6/2002 |
| WO | WO 02/057487 | A2 | 7/2002 |
| WO | WO 02/057487 | A3 | 7/2002 |
| WO | WO 02/28876 | A3 | 8/2002 |
| WO | WO 02/072772 | A2 | 9/2002 |
| WO | WO 02/072773 | A2 | 9/2002 |
| WO | WO 01/64952 | A3 | 12/2002 |
| WO | WO 02/103013 | A2 | 12/2002 |
| WO | WO 01/73134 | A3 | 1/2003 |
| WO | WO 03/012100 | A2 | 2/2003 |
| WO | WO 03/012100 | A3 | 2/2003 |
| WO | WO 03/012142 | A1 | 2/2003 |
| WO | WO 02/103013 | A3 | 3/2003 |
| WO | WO 02/06533 | A3 | 4/2003 |
| WO | WO 02/00938 | A3 | 8/2003 |
| WO | WO 02/29117 | A3 | 8/2003 |
| WO | WO 02/072772 | A3 | 9/2003 |
| WO | WO 03/078645 | A2 | 9/2003 |
| WO | WO 03/078645 | A3 | 9/2003 |
| WO | WO 03/083435 | A2 | 10/2003 |
| WO | WO 03/083435 | A3 | 10/2003 |
| WO | WO 2004/011665 | A2 | 2/2004 |
| WO | WO 02/48402 | A3 | 4/2004 |
| WO | WO 2004/069849 | A2 | 8/2004 |
| WO | WO 2004/092418 | A2 | 10/2004 |
| WO | WO 2004/092418 | A3 | 12/2004 |
| WO | WO 2004/069849 | A3 | 3/2005 |
| WO | WO 2004/011665 | A3 | 7/2005 |
| WO | WO 2005/065321 | A2 | 7/2005 |
| WO | WO 2006/138257 | A2 | 12/2006 |
| WO | WO 2007/030759 | A2 | 3/2007 |
| WO | WO 2004/069849 | A8 | 4/2007 |

| WO | WO 2007/041201 A2 | 4/2007 |
| WO | WO 2007/030759 A3 | 6/2007 |
| WO | WO 2007/041201 A3 | 11/2007 |
| WO | WO 2007/136717 A1 | 11/2007 |
| WO | WO 2008/005459 A2 | 1/2008 |
| WO | WO 2008/005459 A3 | 2/2008 |
| WO | WO 2006/138257 A3 | 12/2008 |

OTHER PUBLICATIONS

Inoue, H. et al., Nucl. Acids Res., vol. 15, pp. 6131-6148 (1987).*
Stratagene Catalog, p. 39 (1988).*
Bing, et al. Bridge Amplification: A Solid Phase PCR System for the Amplification and Detection of Allelic Differences in Single Copy Genes. Genetic Identity Conference Proceedings. 1996. Available at http://www.promega.com/geneticidproc/ussymp7proc/0726.html. Accessed Dec. 22, 2009.
Hatch, et al. Rolling circle amplification of DNA immobilized on solid surfaces and its application to multiplex mutation detection. Genet Anal. Apr. 1999;15(2):35-40.
International search report dated Nov. 20, 2009 for PCT Application No. US2009/33936.
Westin, et al. Anchored multiplex amplification on a microelectronic chip array. Nat Biotechnol. Feb. 2000;18(2):199-204.
Ausubel, et al., Eds. Current Protocols in Molecular Biology. John Wiley & Sons, Inc. 1987 and updates.
Blanchard, et al. High-Density Oligonucleotide Arrays. Biosensors & Bioelectronics 1996; 11(6-7):687-690.
Caruthers, et al. Chemical Synthesis of Deoxyoligonucleotides by the Phosphoramidite Method. Methods in Enzymology. 1987; 154:287-313.
Derisi, et al. Use of a cDNA Microarray to Analyse Gene Expression Patterns in Human Cancer. Nature Genetics 1996; 14:457-460.
Flanagan, et al. A Cytosine Analog That Confers Enhanced Potency to Antisense Oligonucleotides. Proc. Natl. Acad. Sci. U.S.A. 1999; 96(7):3513-3518.
Fodor, et al. Light-Directed, Spatially Addressable Parallel Chemical Synthesis. Science 1991; 251:767-773.
Freshney, ed. Animal Cell Culture. IRL Press: 1987; Oxford, pp. vii-xii (Table of Contents Only.).
Fu, et al. Sequencing Double-Stranded DNA by Strand Displacement. Nucleic Acids Research. 1997; 25(3):677-679.
Gait, Ed. Oligonucleotide Synthesis: A Practical Approach. IRL Press: Oxford, 1984; pp. vii-xii (Table of Contents).
Gasparini, et al. Scanning the First Part of the Neurofibromatosis Type 1 Gene by RNA-SSCP: Identification of Three Novel Mutations and of Two New Polymorphisms. Hum. Genet. 1996;97:492-495.
Guatelli, et al. Isothermal, In Vitro Amplification of Nucleic Acids by a Multienzyme Reaction Modeled After Retroviral Replication. Proc. Natl. Acad. Sci. U.S.A. 1990; 87:1874-1878.
Gubler, et al. A Simple and Very Efficient Method for Generating cDNA Librarie. Gene. 1983; 25:263-269.
Innis, et al. Eds. PCR Protocols: A Guide to Methods and Applications. Academic Press. 1990; pp. v-x (Table of Contents).
Khrapko, et al. A Method for DNA Sequencing by Hybridization with Oligonucleotide Matrix. DNA Sequence. 1991; 1:375-388.
Kumar, et al. The first analogues of locked nucleic acids: Phosphorothioate-LNA and 2'-thio-LNA. Bioorg. Med. Chem. Lett. 1998; 8(16):2219-2222.
Kwoh, D.Y. et al. Transcription-Based Amplification System and Detection of Amplified Human Immunodeficiency Virus Type 1 with a Bead-Based Sandwich Hybridization Format. Proc. Natl. Acad. Sci. USA. 1989; 86:1173-1177.
Lishanski, A. et al. Branch Migration Inhibition in PCR-Amplified DNA: Homogeneous Mutation Detection. Nucl. Acids Res. 2000; 28(9):E42, pp. i-vii.
Lockhart, et al. Expression Monitoring by Hybridization to High-Density Oligonucleotide Arrays. Nature Biotechnology. 1996; 14:1675-1680.
Marshall, et al. DNA Chips: An Array of Possibilities. Nature Biotechnol. 1998; 16:27-31.
Maskos, et al. Oligonucleotide Hybridisations on Glass Supports: A Novel Linker for Oligonucleotide Synthesis and Hybridisation Properties of Oligonucleotides Synthesised In Situ. Nucl. Acids. Res. 1992; 20(7):1679-1684.
Matson, et al. Biopolymer Synthesis on Polypropylene Supports: Oligonucleotide Arrays. Anal. Biochem. 1995; 224(1):110-116.
Mullis et al. Specific synthesis of DNA in vitro via a polymerase-catalyzed chain reaction. Methods in Enzymology. 1987; 155:335-350.
Mullis, et al., Eds. PCR: Polvmerase Chain Reaction. Birkhauser: Boston, 1994; pp. xv-xvii (Table of Contents).
Okayama et al. High Efficiency Cloning of Full-Length cDNA. Molecular and Cell Biology. 1982; 2:161-170.
Orita, et al. Detection of Polymorphisms of Human DNA by Gel Electrophoresis as Single-Strand Conformation Polymorphisms. Proc. Natl. Acad. Sci. USA. 1989; 86(8):2766-2770.
Orita, et al. Rapid and sensitive detection of point mutations and DNA polymorphisms using the polymerase chain reaction. Genomics 1989; 5(4):874-879.
Patel et al. Formation of chimeric DNA primer extension products by template switching onto an annealed downstream oligonucleotide. Proc. Natl. Acad. Sci. U.S.A. 1996; 93:2969-2974.
Pease et al. Light-generated oligonucleotide arrays for rapid DNA sequence analysis. Proc. Natl. Acad. Sci U.S.A. 1994; 91:5022-5026.
Ramsay, G. DNA chips: State-of-the art. Nature Biotechnol. 1998; 16:40-44.
Saiki et al. Primer-directed enzymatic amplification of DNA with a thermostable DNA polymerase. Science. 1988; 239:487-491.
Sambrook, J. et al., Eds. Molecular Cloning: A Laboratory Manual. 2nd Edition, Cold Spring Harbor Laboratory Press, 1989; pp. xi-xxxviii (Table of Contents).
Sarkar et al Screening for Mutations by RNA Single-Strand Conformation Polymorphism (rSSCP): Comparison with DNA-SSCP. Nucl. Acids Res. 1992; 20(4):871-878.
Sasaki et al. Transcriptional sequencing: A method for DNA sequencing using RNA polymerase. Biochemistry 1998; 95:3455-3460.
Scaringe et al. Novel RNA synthesis method using 5'-0-silyl-2'-0-orthoester protecting groups. J. Am. Chem. Soc. 1998; 120:11820-11821.
Scaringe. Advanced 5'-silyl-2'-orthoester approach to RNA oligonucleotide synthesis. Methods in Enzymology. 2000; 317:3-18.
Schena, et al. Parallel human genome analysis: Microarray-based expression monitoring of 1000 genes. Proc. Natl. Acad. Sci. U.S.A. 1996; 93: 10614-10619.
Schena, et al. Quantitative monitoring of gene expression patterns with a complementary DNA microarray. Science. 1995; 270:467-470.
Shalon et al. A DNA microarray system for analyzing complex DNA samples using two-color fluorescent probe hybridization. 1996; Genome Res. 6:639-645.
Suzuki, et al. Detection of ras Gene Mutations in Human Lung Cancers by Single-Strand Conformation Polymorphism Analysis of Polymerase Chain Reaction Products. Oncogene. 1990; 5(7):1037-1043. (Abstarct Only.).
Wahlestedt et al. Potent and nontoxic antisense oligonucleotides containing locked nucleic acids. Proc. Natl. Acad. Sci. 2000; 97(10):5633-5638.
Walker, et al. Isothermal in vitro amplification of DNA by a restruction enzyme/DNA polymerase system. Proc. Natl. Acad. Sci. U.S.A. 1992; 89:392-396.
Wang, et al. High-fidelity mRNA amplification for gene profiling. Nature Biotechnology. 2000; 18: 457-459.
Wu, et al. The Ligation Amplification Reaction (LAR)—Amplification of Specific DNA Sequences Using Sequential Rounds of Template-Dependent Ligation. Genomics. 1989; 4:560-569.
Kurn. U.S. Appl. No. 60/255,638, entitled "Methods and compositions for generation of multiple copies of nucleic acid sequences and methods of detection thereof ," filed Dec. 13, 2000.
U.S. Appl. No. 60/381,457, filed May 17, 2002, Kurn.
U.S. Appl. No. 60/533,381, filed Dec. 29, 2003, Kurn et al.

Abravaya et al. Detection of point mutations with a modified ligase chain reaction (Gap-LCR). Nucleic Acids Research. 1995;23(4):675-682.

Adessi et al. Solid phase DNA amplification: characterisation of primer attachment and amplification mechanisms. Nucleic Acids Research. 2000;28(20):E87.

Agrawal et al. Site Specific Functionalization of Oligonucleotides for Attaching Two Different Reporter Groups. Nucleic Acids Research. 1990;18(18):5419-5423.

Akhras et al. Connector inversion probe technology: a powerful one-primer multiplex DNA amplification system for numerous scientific applications. PLoS ONE. 2007;2(9):e915.

Arashi-Heese et al. XcmI site-containing vector for direct cloning and in vitro transcription of PCR product. Molecular Biotechnology. 1999;12(3):281-3.

Baner et al. Parallel gene analysis with allele-specific padlock probes and tag microarrays. Nucleic Acids Research. 2003;31(17):e103.

Barbas III et al. In Vitro Evolution of a Neutralizing Human Antibody to Human Immunodeficiency Virus Type I to Enhance Affinity and Broaden Strain Cross-Reactivity. Proc. Natl. Acad. Sci. USA. 1994;91:3809-3813.

Barker et al. Increased DNA microarray hybridization specificity using sscDNA targets. BMC Genomics. 2005;6(1):57.

Barth et al. Combining Phage Display and Screening of cDNA Expression Libraries: A New Approach for Identifying the Target Antigen of an scFv Preselected by Phage Display. Journal of Molecular Biology. 2000;301:751-757.

Beaucage et al. Deoxynucleoside Phosphoramidites—A New Class of Key Intermediates for Deoxypolynucleotide Synthesis. Tetrahedron Letters. 1981;22(20):1859-1862.

Beggs, et al. Characterization of *Mycobacterium tuberculosis* complex direct repeat sequence for use in cycling probe reaction. J Clin Microbiol. Dec. 1996;34(12):2985-9.

Bekkaoui et al. Rapid detection of the mecA gene in methicillin resistant *staphylococci* using a colorimetric cycling probe technology. Diagnostic Microbiology and Infectious disease. 1999;34(2):83-90.

Ben-Artzi, et al. Double-stranded RNA-dependent RNase activity associated with human immunodeficiency virus type 1 reverse transcriptase. Proc Natl Acad Sci U S A. Feb. 1, 1992;89(3):927-31.

Brenner et al. Gene expression analysis by massively parallel signature sequencing (MPSS) on microbead arrays. Nature Biotechnology. 2000;18(6):630-634.

Brown et al. Chemical Synthesis and Cloning of a Tyrosine tRNA Gene. Methods in Enzymology. 1979;68:109-151.

Brown, T.A. Ed. Molecular Biology, LabFax. Bios Scientific Publishers. Academic Press. 1991; pp. 147-148.

Chetverin et al. On the nature of spontaneous RNA synthesis by Q beta replicase. Journal of Molecular Biology. 1991;222(1):3-9.

Church. Genomes for ALL. Scientific American. 2006;294(1):46-54.

Coco et al. DNA Shuffling Method for Generating Highly Recombined Genes and Evolved Enzymes. Nature Biotechnology. 2001;19:354-359.

Cohen et al. Construction of biologically functional bacterial plasmids in vitro. Proc. Natl. Acad. Sci. USA. 1973;70(11):3240-4.

Coljee et al. Seamless Gene Engineering Using RNA- and DNA-Overhang Cloning. Nature Biotechnology. 2000;18:789-791.

Crameri et al. Molecular Evolution of an Arsenate Detoxification Pathway by DNA Shuffling. Nature Biotechnology. 1997;15:436-438.

Dafforn et al. Linear mRNA amplification from as little as 5 ng total RNA for global gene expression analysis. Biotechniques. 2004;37(5):854-857.

Dahl et al. Multigene amplification and massively parallel sequencing for cancer mutation discovery. Proc. Natl. Acad. Sci. USA. 2007;104(22):9387-9392.

Daigo et al. Degenerate Oligonucleotide Primed-Polymerase Chain Reaction-Based Array Comparative Genomic Hybridization for Extensive Amplicon Profiling of Breast Cancers. American Journal of Pathology. 2001;158(5):1623-1631.

Database WPI, Section Ch, Week 199507, Derwent Publications Ltd., London, GB; AN 1995-047919, XP002276586 & JP 06 327500 A (Toyobo KK), Nov. 29, 1994. (Abstract Only). 1 page total.

Dean et al. Comprehensive Human Genome Amplification Using Multiple Displacement Amplification. Proc. Natl. Acad. Sci. USA. 2002;99(8):5261-5266.

Dietmaier et al. Multiple Mutation Analyses in Single Tumor Cells with Improved Whole Genome Amplification. American Journal of Pathology. 1999;154(1):83-95.

Dressman et al. Transforming single DNA molecules into fluorescent magnetic particles for detection and enumeration of genetic variations. Proc. Natl. Acad. Sci. USA. 2003;100(15):8817-8822.

European Search Report (Supplementary partial) mailed Dec. 22, 2005 for European Patent Application No. 02731119.0.

European search report dated Mar. 13, 2006 for Application No. 02731119.

European search report dated Sep. 17, 2009 for Application No. 04002084.4.

European search report dated Nov. 13, 2006 for Application No. 03717952.

European Search Report mailed on May 13, 2004 for patent application No. 02721342.0-2402.

Fan et al. Highly parallel genomic assays. Nature Reviews Genetics. 2006;7(8):632-644.

Freier et al. Improved Free-Energy Parameters for Predictions of RNA Duplex Stability. Proc. Natl. Acad. Sci. USA. 1986;83:9373-9377.

Ghadessy et al. Directed evolution of polymerase function by compartmentalized self-replication. Proc. Natl. Acad. Sci. USA. 2001;98(8):4552-4557.

Go. Protein Structures and Split Genes. Advances in Biophysics. 1985;19:91-131.

Goodchild. Conjugates of Oligonucleotides and Modified Oligonucleotides: A Review of Their Synthesis and Properties. Bioconjugate Chemistry. 1990;1(3):165-187.

Gulick et al. Forced Evolution of Glutathione S-Transferase to Create a More Efficient Drug Detoxication Enzyme. Proc. Natl. Acad. Sci. USA. 1995;92:8140-8144.

Habermann et al. Clostridial Neurotoxins: Handling and Action at the Cellular and Molecular Level. Current Topics in Microbiology and Immunology. 1986;129:93-179.

Heim et al. Engineering Green Fluorescent Protein for Imporved Brightness, Longer Wavelengths and Fluorescence Resonance Energy Transfer. Current Biology. 1996;6:178-182.

Hendrickson et al. High sensitivity multianalyte immunoassay using covalent DNA-labeled antibodies and polymerase chain reaction. Nucleic Acids Research. 1995;23: 522-529.

Hottiger, et al. Strand displacement activity of the human immunodeficiency virus type 1 reverse transcriptase heterodimer and its individual subunits. J Biol Chem. Jan. 14, 1994;269(2):986-91.

Huber, et al. Processing of the primer for plus strand DNA synthesis by human immunodeficiency virus 1 reverse transcriptase. J Biol Chem. Jun. 25, 1990;265(18):10565-73.

Hutchison et al. Cell-free cloning using phi29 DNA polymerase. Proc. Natl. Acad. Sci. USA. 2005;102(48):17332-17336.

International search report dated Feb. 3, 2003 for PCT Application No. US2001/047775.

International search report dated Mar. 9, 2007 for PCT Application No. US2006/035154.

International search report dated Mar. 18, 2003 for PCT Application No. US01/20660.

International search report dated Jun. 23, 2003 for PCT Application No. US02/07306.

International search report dated Jul. 3, 2001 for PCT Application No. US00/25104.

International search report dated Sep. 28, 2009 for PCT Application No. US2009/033964.

International search report dated Oct. 20, 2009 for PCT Application No. US2009/037870.

International Search Report mailed Aug. 8, 2003 for PCT Application No. PCT/US02/07377.

International Search Report mailed on Jan. 8, 2004, for PCT patent application No. PCT/US03/07425 filed on Mar. 11, 2003.

International Search Report mailed on Oct. 15, 2004 for PCT Application No. PCT/US2004/012779 filed on Apr. 14, 2004.

International Search Report mailed on Oct. 30, 2003, for PCT patent application No. PCT/US3/10148 filed on Mar. 31, 2003.
Joyce. Directed Molecular Evolution. Scientific American. 1992;267(6):90-97.
Kass et al. Inter-alu polymerase chain reaction: advancements and applications. Analytical Biochemistry. 1955;228(2):185-193.
Kikuchi et al. An Effective Family Shuffling Method Using Single-Stranded DNA. Gene. 2000;243:133-137.
Kikuchi et al. Novel Family Shuffling Methods for the in vitro Evolution of Enzymes. Gene. 1999;236:159-167.
Kojima et al. PCR amplification from single DNA molecules on magnetic beads in emulsion: application for high-throughput screening of transcription factor targets. Nucleic Acids Research. 2005;33(17):e150.
Kolkman et al. Directed Evolution of Proteins by Exon Shuffling. Nature Biotechnology. 2001;19:423-428.
Kricka. Nonisotopic DNA Probe Techniques. Academic Press. 1992. (Table of Contents only).
Kurn et al. Novel isothermal, linear nucleic acid amplification systems for highly multiplexed applications. Clinical Chemistry. 2005;51(10):1973-1981.
Kurtzman et al. Advances in Directed Protein Evolution by Recursive Genetic Recombination: Applications to Therapeutic Proteins. Current Opinion in Biotechnology. 2001;12:361-370.
Li et al. Amplification and analysis of DNA sequences in single human sperm and diploid cells. Nature. 1988;335(6189):414-417.
Lizardi et al. Mutation detection and single-molecule counting using isothermal rolling-circle amplification. Nature Genetics. 1998;19(3):225-232.
MacMillan et al. Synthesis of Functionally Tethered Oligodeoxynucleotides by the Convertible Nucleoside Approach. The Journal of Organic Chemistry. 1990;55:5931-5933.
Makos et al. Oligonucleotide Hybridisations on Glass Supports: A Novel Linker for Oligonucleotide Synthesis and Hybridisation Properties of Oligonucleotides Synthesised in situ. Nucleic Acids Research. 1992;20(7):1679-1684.
Marcy et al. Nanoliter reactors improve multiple displacement amplification of genomes from single cells. PLoS Genetics. 2007;3(9):1702-1708.
Medical Dictionary, online, definition of RNase I, pp. 1-3, retrieved 2009, from: http://www.mondofacto.com/facts/dictionary?Escherichia+coli+RNase+I.
Mitra et al. In situ localized amplification and contact replication of many individual DNA molecules. Nucleic Acids Research. 1999;27(24):e34.
Mullis et al. Specific Enzymatic Amplification of DNA In Vitro: the Polymerase Chain Reaction. Cold Spring Harbor Symposia on Quantitative Biology. 1986;51:263-273.
Nakano et al. Single-molecule PCR using water-in-oil emulsion. Journal of Biotechnology. 2003;102(2):117-24.
Narang et al. Improved Phosphotriester Method for the Synthesis of Gene Fragments. Methods of Enzymology. 1979;68:90-99.
New England Biolab Polymerases. Polymerases from NEB. 2008;p. 1-2. Available at http://www.neb.com/nebeconun/tech_reference/polymerases/polymerases_from_neb.asp. Accessed Jun. 30, 2008.
Nugen, Inc. Ovation Biotin RNA Amplification and Labeling System User Guide. Catalog #2300-12. Published 2004.
Nugen, Inc. Technical Report #1. The Ovation Biotin System Validation for Use with Affymetrix GeneChip Arrays. Published 2004.
Pieles et al. Preparation of a Novel Psoralen Containing Deoxyadenosine Building Block for the Facile Solid Phase Synthesis of Psoralen-Modified Oligonucleotides for a Sequence Specific Crosslink to a Given Target Sequence. Nucleic Acids Research. 1989;17(22):8967-8978.
Pluckthun et al. In Vitro Selection and Evolution of Proteins. Advances in Protein Chemistry. 2001;55:367-403.
Roget et al. Synthesis and Use of Labelled Nucleoside Phosphoramidite Building Blocks Bearing a Reporter Group: Biotinyl, Dinitrophenyl, Pyrenyl and Dansyl. Nucleic Acids Research. 1989;17:7643-7651.
Sano et al. Immuno-PCR: very sensitive antigen detection by means of specific antibody-DNA conjugates. Science. 1992;258:120-122.
Schmidt-Dannert. Directed Evolution of Single Proteins, Metabolic Pathways, and Viruses. Biochemistry. 2001;40(44):13125-13136.
Schweitzer et al. Immunoassays with rolling circle DNA amplification: a versatile platform for ultrasensitive antigen dectection. Proc. Natl. Acad. Sci. USA. 2000;97(18):10113-10119.
Scott et al. Production of Cyclic Peptides and Proteins in vivo. Proc. Natl. Acad. Sci. USA. 1999;96(24):13638-13643.
Shendure et al. Accurate multiplex polony sequencing of an evolved bacterial genome. Science. 2005;309(5741):1728-32.
Stemmer. DNA Shuffling by Random Fragmentation and Reassembly: In Vitro Recombination for Molecular Evolution. Proc. Natl. Acad. Sci. USA. 1994;91:10747-10751.
Stemmer. Rapid Evolution of a Protein In Vitro by DNA Shuffling. Nature. 1994;370:389-391.
Stoecklein et al. SCOMP Is Superior to Degenerated Oligonucleotide Primed Polymerase Chain Reaction for Global Amplification of Minute Amounts of DNA From Microdissected Archival Tissue Samples. American Journal of Pathology. 2002;161(1):43-51.
Stump et al. The Use of Modified Primers to Eliminate Cycle Sequencing Artifacts. Nucleic Acids Research. 1999;27(23):4642-4648.
Tesler et al. Synthesis and Characterization of DNA Oligomers and Duplexes Containing Covalently attached Molecular Labels: Comparison of Biotin, Fluorescein, and Pyrene Labels by Thermodynamic and Optical Spectroscopic Measurements. Journal of the American Chemical Society. 1989;111:6966-6976.
Tijessen. Hybridization with Nucleic Acid Probes. Elsevier Science Publishers. 1993. (Table of Contents).
Tinoco et al. Improved Estimation of Secondary Structure in Ribonucleic Acids. Nature New Biology. 1973;246:40-41.
Traut. Are Proteins Made of Modules? Molecular and Cellular Biochemistry. 1986;70:3-10.
Vogelstein et al. Digital PCR. Proc. Natl. Acad. Sci. USA. 1999;96(16):9236-41.
Volkov et al. Recombination and Chimeragenesis by in vitro Heteroduplex Formation and in vivo Repair. Nucleic Acids Research. 1999;27(18):e18i-e18vi.
Wadenback et al. Comparison of standard exponential and linear techniques to amplify small cDNA samples for microarrays. BMC Genomics. 2005;6(1):61.
Walker et al. Strand displacement amplification—an isothermal, in vitro DNA amplification technique. Nucleic Acids Research 1992;20(7):1691-1696.
Wang et al. Whole genome amplification and high-throughput allelotyping identified five distinct deletion regions on chromosomes 5 and 6 in microdissected early-stage ovarian tumors. Cancer Research. 2001;61:4169-4174.
Wiltshire et al. Detection of Multiple Allergen-Specific IgEs on Microarrays by Immunoassay with Rolling Circle Amplification. Clinical Chemistry. 2000;46(12):1990-1993.
Wu et al. Detection of *Clostridium botulinum* neurotoxin type a using immuno-PCR. Letters in Applied Microbiology. 2001;32:321-325.
You et al. Directed Evolution of Subtilisin E in *Bacillus subtilis* to Enhance Total Activity in Aqueous Dimethylformamide. Protein Engineering. 1994;9(1):77-83.
Zhang et al. Directed Evolution of a Fucosidase From a Galactosidase by DNA Shuffling and Screening. Proc. Natl. Acad. Sci. USA. 1997;94:4504-4509.
Zhang et al. Protein quantification from complex protein mixtures using a proteomics methodology with single-cell resolution. Proc. Natl. Acad. Sci. USA. 2001;98(10):5497-5502.
Zheng et al. Whole Genome Amplification Increases the Efficiency and Validity of Buccal Cell Genotyping in Pediatric Populations. Cancer Epidemiology. 2001;10:697-700.
European search report dated Nov. 11, 2008 for Application No. 3718172.4.
Miyachi, et al. Application of chimeric RNA—DNA oligonucleotides to the detection of pathogenic microorganisms using surface plasmon resonance. Analytica Chimica Acta. 2000; 407(1):1-10.
Office action dated Feb. 17, 2010 for U.S. Appl. No. 11/933,332.

* cited by examiner

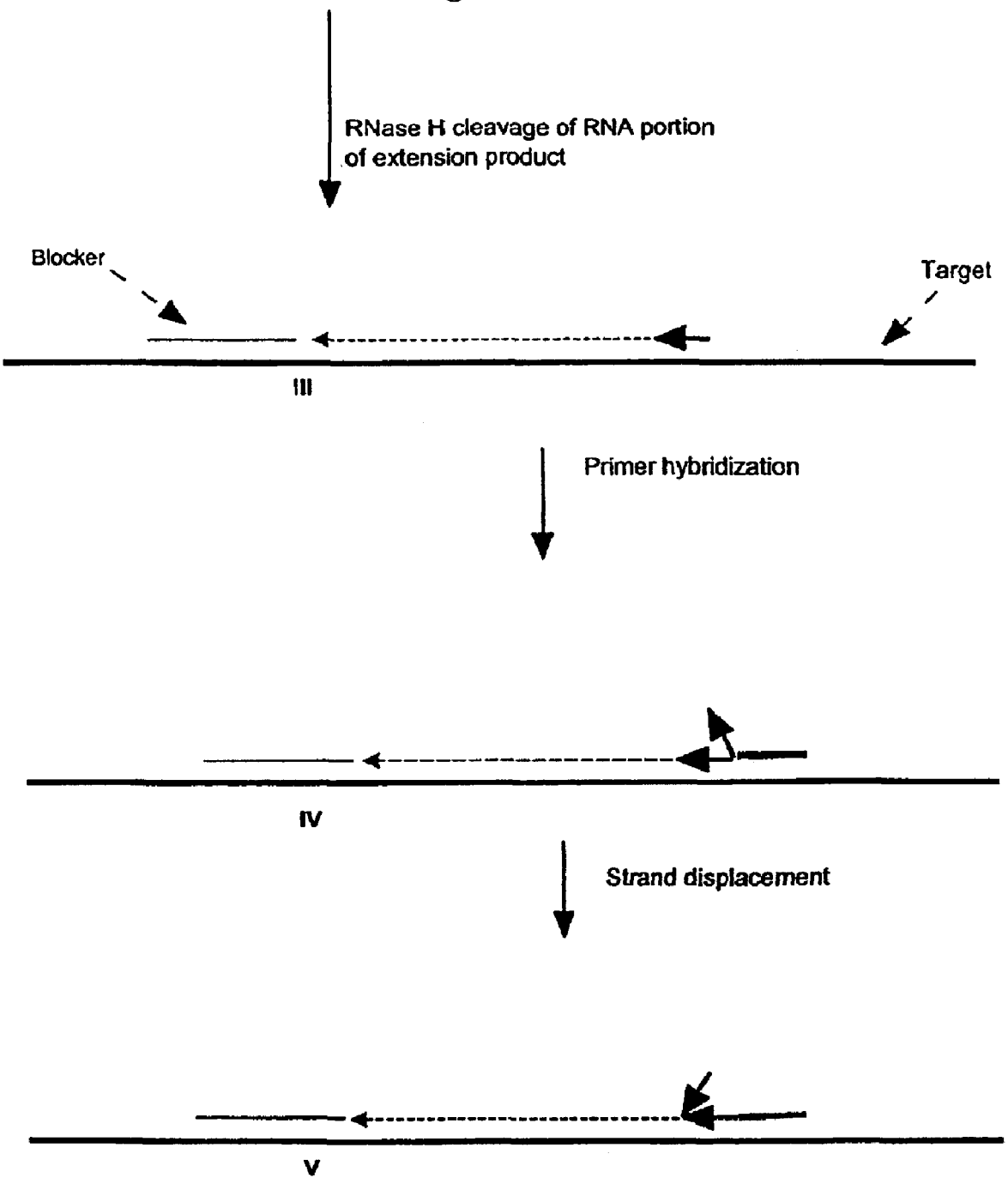

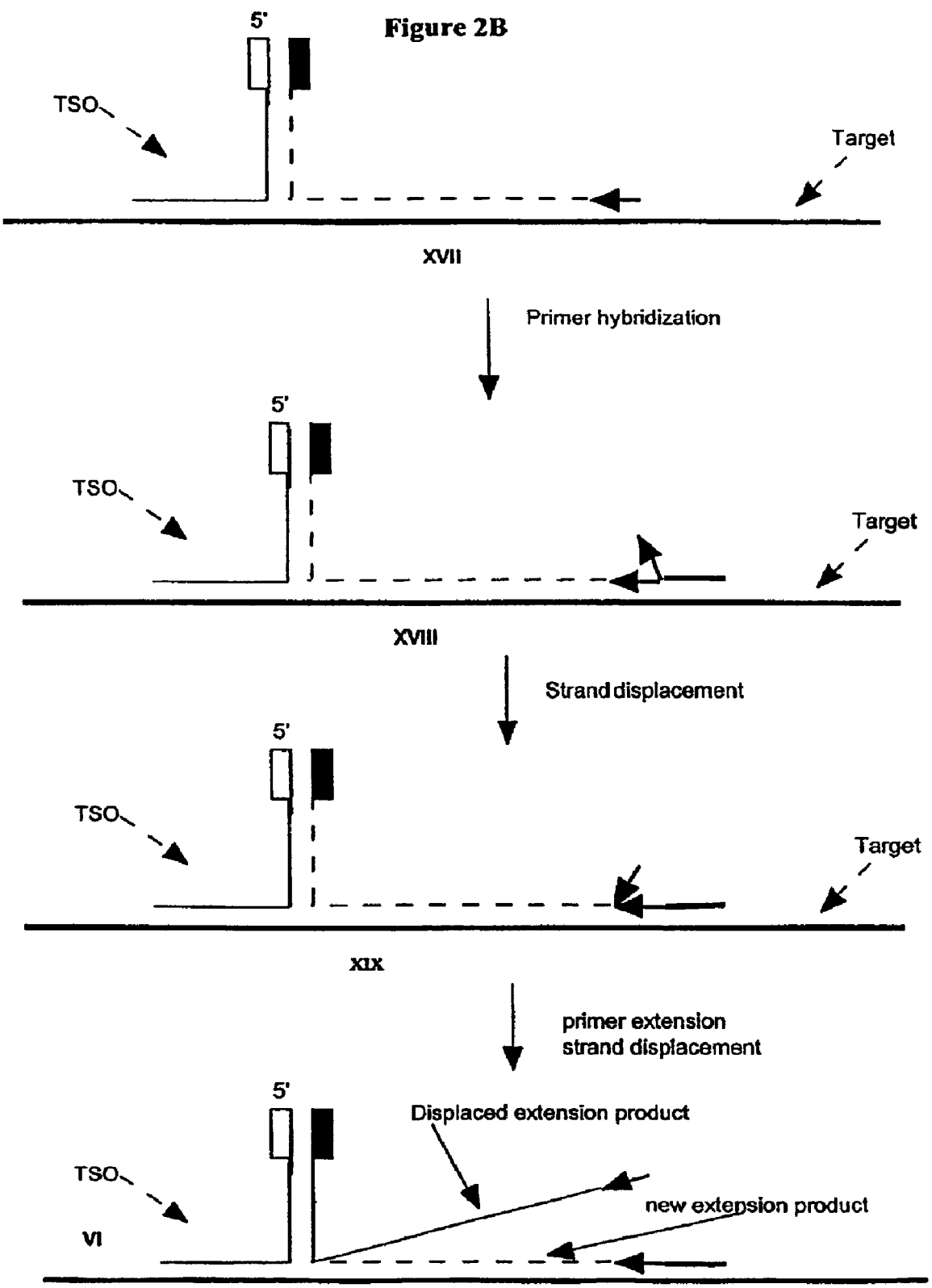

SEQUENCE LISTING

<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: Description of DNA/RNA Molecule: Synthetic

```
                                       primer
<220> FEATURE:
<223> OTHER INFORMATION: Description of Artificial Sequence: Synthetic
      primer

<400> SEQUENCE: 1
acggaugcgg ucuccagtgt                                                    20

<210> SEQ ID NO 2
<211> LENGTH: 115
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cggtacgctg atcaaagatc cgtgcaacaa atgtcatggt catggtcgtg ttgagcgcag        60
caaaacgctg tccgttaaaa tcccggcagg ggtggacact ggagaccgca tccgt           115

<210> SEQ ID NO 3
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
cggtacgctg atcaaagatc cgtgcaacaa atgtcatggt catggtcgtg ttgagcgcag        60
caaaacgctg tccgttaaaa tcccggcagg ggtggacact ggagaccgca tccgtcttgc      120
gggcgaaggt gaagcgggcg agcatggcgc accggcaggc gatctgtacg ttcaggttca      180
ggttaaacag caccgatttt cgagcgtga aggcaacaac ctgtattgcg aagtcccgat       240
caacttcgct atggcggcgc tgggtggcga atcgaagta ccgacccttg atggtcgcgt       300
caaactgaaa gtgcctggcg aaacccagac cggtaagcta ttccgtatgc g               351

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cggtacgctg atcaaagatc cgt                                                23

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgcatacgga atagcttacc ggtct                                              25

<210> SEQ ID NO 6
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 6
atgtcatggt catggtcgtg t                                              21

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctcaacacga ccatgaccat gacatttgtt g                                   31

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
taatacgact cactataggg aggag                                          25

<210> SEQ ID NO 9
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggaattctaa tacgactcac tagggaga gatcgagtag ctccggtacg ctgatcaaag       60
atccgtg                                                              67

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atcgagtagc tc                                                        12

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
taatacgact cactataggg agagcggtac gctgatcaaa gatccgtg                 48

<210> SEQ ID NO 12
<211> LENGTH: 55
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 12
ggaattctaa tacgactcac tatagggaga gcggtacgct gatcaaagat ccgtg          55

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
taatacgact cactataggg agagatcgag tagctccggt acgctgatca aagatccgtg     60

<210> SEQ ID NO 14
<211> LENGTH: 100
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agtgtccacc cctgccggga ttttaacgga cagcgttttg ctgcgctcaa cacgaccatg     60
accatgacat tgttgcacg gatctttgat cagcgtaccg                           100

<210> SEQ ID NO 15
<211> LENGTH: 21
<212> TYPE: DNA
<213> ORGANISM: Artificial Sequence
<220> FEATURE:
<223> OTHER INFORMATION: Description of DNA/RNA Molecule: Synthetic
      primer
<220> FEATURE:
<223> OTHER INFORMATION: Description of Artificial Sequence: Synthetic
      primer

<400> SEQUENCE: 15
gacggaugcg gucuccagtg t                                               21

<210> SEQ ID NO 16
<211> LENGTH: 25
<212> TYPE: DNA
<213> ORGANISM: Artificial Sequence
<220> FEATURE:
<223> OTHER INFORMATION: Description of DNA/RNA Molecule: Synthetic
      primer
<220> FEATURE:
<223> OTHER INFORMATION: Description of Artificial Sequence: Synthetic
      primer

<400> SEQUENCE: 16
gcaagacgga ugcggucucc agtgt                                           25

<210> SEQ ID NO 17
<211> LENGTH: 19
<212> TYPE: DNA
<213> ORGANISM: Artificial Sequence
<220> FEATURE:
<223> OTHER INFORMATION: Description of DNA/RNA Molecule: Synthetic
      primer
<220> FEATURE:
<223> OTHER INFORMATION: Description of Artificial Sequence: Synthetic
      primer
```

<400> SEQUENCE: 17
gacgatgcgu ctccagtgt                                                    19

<210> SEQ ID NO 18
<211> LENGTH: 21
<212> TYPE: DNA
<213> ORGANISM: Artificial Sequence
<220> FEATURE:
<223> OTHER INFORMATION: Description of DNA/RNA Molecule: Synthetic
      primer
<220> FEATURE:
<223> OTHER INFORMATION: Description of Artificial Sequence: Synthetic
      primer

<400> SEQUENCE: 18
gacggatgcg guctccagug t                                                 21

<210> SEQ ID NO 19
<211> LENGTH: 24
<212> TYPE: DNA
<213> ORGANISM: Artificial Sequence
<220> FEATURE:
<223> OTHER INFORMATION: Description of DNA/RNA Molecule: Synthetic
      primer
<220> FEATURE:
<223> OTHER INFORMATION: Description of Artificial Sequence: Synthetic
      primer

<400> SEQUENCE: 19
gacggatgcg guctccagug ucca                                              24

<210> SEQ ID NO 20
<211> LENGTH: 20
<212> TYPE: DNA
<213> ORGANISM: Artificial Sequence
<220> FEATURE:
<223> OTHER INFORMATION: Description of DNA/RNA Molecule: Synthetic
      primer
<220> FEATURE:
<223> OTHER INFORMATION: Description of Artificial Sequence: Synthetic
      primer

<400> SEQUENCE: 20
acggaugcgg ucuccagtgt                                                   20

<210> SEQ ID NO 21
<211> LENGTH: 20
<212> TYPE: DNA
<213> ORGANISM: Artificial Sequence
<220> FEATURE:
<223> OTHER INFORMATION: Description of DNA/RNA Molecule: Synthetic
      primer
<220> FEATURE:
<223> OTHER INFORMATION: Description of Artificial Sequence: Synthetic
      primer

<400> SEQUENCE: 21
acggaugcgg ucuccagtgt                                                   20

<210> SEQ ID NO 22
<211> LENGTH: 21
<212> TYPE: DNA
<213> ORGANISM: Artificial Sequence
<220> FEATURE:
<223> OTHER INFORMATION: Description of DNA/RNA Molecule: Synthetic
      primer
<220> FEATURE:
<223> OTHER INFORMATION: Description of Artificial Sequence: Synthetic

```
                                -continued
    primer

<400> SEQUENCE: 22
gacggaugcg gucuccagtg t                                             21

<210> SEQ ID NO 23
<211> LENGTH: 100
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
agtgtccacc cctgccggga ttttaacgga cagcgttttg ctgcgctcaa cacgaccatg     60
accatgacat ttgttgcacg gatctttgat cagcgtaccg                         100
```

METHODS AND COMPOSITIONS FOR TRANSCRIPTION-BASED NUCLEIC ACID AMPLIFICATION

CROSS-REFERENCE

This application is a continuation of U.S. Ser. No. 10/686,466, filed Oct. 14, 2003, now U.S. Pat. No. 7,294,461, which is a divisional of U.S. Ser. No. 09/893,191, filed Jun. 26, 2001, now U.S. Pat. No. 6,686,156, which claims the priority benefit of provisional patent applications 60/277,748, filed Mar. 21, 2001 and 60/213,908 filed Jun. 26, 2000, all of which are incorporated herein by reference in their entirety.

TECHNICAL FIELD

This invention relates to the filed of polynucleotide amplification. More particularly, the invention provides methods, compositions and kits for amplifying (i.e., making multiple copies) target polynucleotide sequences which involve transcription, and employ either an RNA/DNA composite primer and/or a target switch polynucleotide.

BACKGROUND ART

The development of methods for nucleic acid amplification and detection of amplification products have advanced the detection, identification, quantification and sequence analyses of nucleic acids in recent years. Use of these methods has contributed to rapid advances in the areas of genomics, cell biology, molecular medicine, genetics and the like.

Nucleic acid analysis is widely used for detection and identification of pathogens, detection of gene alterations leading to defined phenotypes, diagnosis of genetic diseases or susceptibility to such disease, assessment of gene expression in development, in disease and in response to defined stimuli, as well as in various genome projects. Other applications of nucleic acid amplification methods include the detection of rare cells, detection of pathogens and the detection of altered gene expression in malignancy, and the like. Nucleic acid amplification is potentially useful for both qualitative analysis such as the detection of the presence of defined nucleic acid sequences, and quantification of defined gene sequences. The latter is useful for assessing and determining the amount of pathogenic sequences in a sample as well as for the determination of gene multiplication or deletion, as often found in cell transformation from normal to malignant type.

Although detection of the presence of a defined nucleic acid sequence, and its sequence analysis, can be carried out by direct probe hybridization to target nucleic acid sequences, the method generally lacks sensitivity when amounts of the target nucleic acid sequence present in the test sample are low. One solution to this obstacle was the development of methods for generation of multiple copies of the defined nucleic acid sequence to make them more accessible to further analysis. Methods for generating multiple copies of a specific nucleic acid sequence in a sample are generally defined as target amplification methods. Other methods for increasing the sensitivity of detection of hybridization analysis are based on the generation of multiple products from the hybridized probe(s), for example, cleaving the hybridized probe to form multiple products or ligating adjacent probes to form a unique hybridization-dependent product. Similarly, increased sensitivity of hybridization reaction is achieved by methods for amplifying signals generated by the hybridization event, such as methods based on hybridization of branched DNA probes.

Various target nucleic acid amplification methods have been described in recent years. Target nucleic acid amplification is carried out through multiple cycles of incubations at various temperatures (thermal cycling) or alternatively, carried out by an isothermal process. The discovery of thermostable nucleic acid modifying enzymes has also contributed to rapid advances in nucleic acid amplification technology. Thermostable nucleic acid modifying enzymes, such as DNA and RNA polymerases, ligases, nucleases and the like, are used both in methods dependent on thermal cycling and isothermal amplification methods. For example, a method for "homogeneous isothermal amplification and detection of nucleic acids using a template switch oligonucleotide" is described in WO/070095A2 (Liu, et al.)

The most commonly used target amplification method is the polymerase chain reaction (PCR) which is based on multiple cycles of denaturation, hybridization of two oligonucleotide primers, one to each strand of a double stranded target, and primer extension by a nucleotide polymerase to produce multiple double stranded copies of the target sequence. Many variations of PCR have been described, and the method is being used for amplification of DNA or RNA nucleic acid sequences, sequence determination, mutation analysis and others. (see PCR Protocols: A Guide to Methods and Applications (Innis, M., Gelfand, D., Sninsky, J. and White, T., eds.) Academic Press (1990); Mullis et al., Methods in Enzymology, 155:335-350 (1987)). Thermocycling-based methods that employ a single primer are also described. Other methods that depend on thermal cycling include the ligase chain reaction (LCR) and the related repair chain reaction (RCR).

Isothermal nucleic acid amplification methods based on strand displacement, are described. See, for e.g., Fraiser et al. in U.S. Pat. No. 5,648,211; Cleuziat et al. in U.S. Pat. No. 5,824,517; and Walker et al. Proc. Natl. Acad. Sci. U.S.A. 89:392-396 (1992). Other isothermal target amplification methods are the transcription-based amplification methods, in which an RNA polymerase promoter sequence is incorporated into primer extension products at an early stage of the amplification (WO/01050), and target sequence, or target complementary sequence, is further amplified by transcription and digestion of the RNA strand in a DNA/RNA hybrid intermediate product. See, for example, U.S. Pat. Nos. 5,169,766 and 4,786,600. Target nucleic acid amplification may be carried out through multiple cycles of incubations at various temperatures, i.e. thermal cycling, or at one temperature (an isothermal process). These methods include transcription-mediated amplification (TMA), self-sustained sequence replication (3SR), nucleic acid sequence-based amplification (NASBA), and variations thereof. See, for example, Guatelli et al. Proc. Natl. Acad. Sci. U.S.A. 87:1874-1878 (1990); U.S. Pat. No. 5,766,849 (TMA); and U.S. Pat. No. 5,654,142 (NASBA). Other amplifications methods use template switching oligonucleotides (TSOs) and blocking oligonucleotides. For example, a template switch amplification method in which chimeric DNA primers are utilized is disclosed in U.S. Pat. No. 5,679,512 and by Patel et al. (Proc. Natl. Acad. Sci. U.S.A. 93:2969-2974 (1996)), and a method that uses blocking oligonucleotides is disclosed by Laney et al. in U.S. Pat. No. 5,679,512.

Since isothermal target amplification methods do not require a thermocycler, they are easier to adapt to common instrumentation platforms. However, previously known isothermal target amplification methods have severe drawbacks. Amplification according to the strand displacement amplification (SDA) process requires the presence of sites for defined restriction enzymes, thus limiting its applicability.

Existing transcription-based amplification methods, such as the NASBA and TMA, on the other hand, are limited by the need for incorporation of the RNA polymerase promoter sequence into the amplification product by means of a primer, a process prone to causing non-specific amplification. Moreover, the mechanism of amplification of a DNA target by these transcription-based amplification methods is not well established.

The completion of sequencing of a number of genomes, and the sequencing of the human genome in particular, has tremendous implications for advances in molecular and cell biology in general and molecular medicine in particular. Development of methods for isothermal gene sequencing will greatly enhance the application of this information in various testing facilities, as isothermal sequencing markedly simplifies the process of genetic identification compared to current methods that require thermocycling.

The methods of the present invention provide for isothermal, high efficiency nucleic acid sequence amplification and methods that use these amplification methods and products, such as in sequence determination.

All references cited herein, including patent applications and publications, are incorporated by reference in their entirety.

DISCLOSURE OF THE INVENTION

The invention provides methods, compositions and kits for amplifying polynucleotide sequences. The methods generally comprise use of a primer (which in some aspects of the invention is an RNA/DNA composite primer), optionally a termination sequence, and a propromoter oligonucleotide sequence.

Accordingly, in one aspect the invention provides methods for generating multiple copies of a nucleic acid sequence of interest, comprising the steps of: (a) hybridizing a single stranded target polynucleotide comprising the nucleic acid sequence of interest with a first primer, wherein said first primer is a composite primer comprising an RNA portion and a 3' DNA portion; (b) optionally hybridizing a polynucleotide comprising a termination polynucleotide sequence to a region of the target polynucleotide 5' with respect to hybridization of the first primer to the target polynucleotide; (c) extending the first primer with a DNA-dependent DNA polymerase to generate a complex comprising a first primer extension product and target polynucleotide; (d) cleaving the RNA portion from the composite primer in the complex of first primer extension product and target polynucleotide with an enzyme that cleaves RNA from an RNA/DNA hybrid such that another composite primer (which is generally and preferably the same as the first primer) can hybridize to the target polynucleotide and repeat primer extension by strand displacement to produce displaced primer extension product; (e) hybridizing a propromoter polynucleotide comprising a propromoter and a region which hybridizes to the displaced primer extension product under conditions which allow transcription to occur by RNA polymerase (these conditions generally but not necessarily include extension of the 3' end of the primer extension product to generate a double stranded promoter region), such that an RNA transcript comprising sequences complementary to the displaced primer extension products is produced; (f) hybridizing a second primer to the RNA transcript of step (e); (g) extending the second primer with RNA-dependent DNA polymerase to generate a complex comprising a second primer extension product and the RNA transcript; (h) cleaving RNA in the complex of step (g) with an enzyme that cleaves RNA in an RNA/DNA hybrid; (i) hybridizing the single stranded second primer extension product with a propromoter polynucleotide, wherein the propromoter polynucleotide comprises a propromoter and a region which hybridizes to the single stranded second primer extension product under conditions which allow transcription to occur by RNA polymerase (these conditions generally but not necessarily include extension of the 3' end of the primer extension product to generate a double stranded promoter region), such that an RNA transcript comprising the sequence of interest is produced; whereby multiple copies of the nucleic acid sequence of interest are produced.

In another aspect the invention provides methods for generating multiple copies of a nucleic acid sequence of interest, comprising (a) combining: the complex comprising a first primer extension product and target polynucleotide as described above; a composite primer (which is generally and preferably the same as the first primer) that is hybridizable to the target polynucleotide, wherein the composite primer is a primer that comprises an RNA portion and a 3' DNA portion; an enzyme that cleaves RNA from an RNA/DNA hybrid; a propromoter polynucleotide comprising a propromoter and a region which hybridizes to displaced composite primer extension product; an RNA polymerase; a second primer that is hybridizable to a sense RNA transcript comprising the sequence of interest; an RNA-dependent DNA polymerase; and a propromoter polynucleotide comprising a propromoter and a region which hybridizes to a second primer extension product; and (b) incubating the mixture of step (a) under conditions that permit primer hybridization and extension, RNA cleavage, displacement of the first primer extension product from the complex comprising a first primer extension product and target polynucleotide when its RNA is cleaved and a composite primer binds to the target polynucleotide in the complex, hybridization of a propromoter polynucleotide to a first primer extension product to form a complex comprising a first primer extension product and a propromoter polynucleotide, hybridization of a propromoter polynucleotide to a second primer extension product to form a complex comprising a second primer extension product and a propromoter polynucleotide, and RNA transcription, whereby multiple copies of the nucleic acid sequence of interest are generated.

In another aspect the invention provides methods for generating multiple copies of a nucleic acid sequence of interest, comprising: (a) combining: the displaced primer extension product generated as described above; a propromoter polynucleotide comprising a propromoter and a region which hybridizes to displaced first primer extension product; an RNA polymerase; a second primer that is hybridizable to a sense RNA transcript comprising the sequence of interest; an RNA-dependent DNA polymerase; an enzyme that cleaves RNA from an RNA/DNA hybrid; and a propromoter polynucleotide comprising a propromoter and a region which hybridizes to a second primer extension product; and (b) incubating the mixture of step (a) under conditions that permit primer hybridization and extension, RNA cleavage, hybridization of a propromoter polynucleotide to a first primer extension product to form a complex comprising a first primer extension product and a propromoter polynucleotide, hybridization of a propromoter polynucleotide to a second primer extension product to form a complex comprising a second primer extension product and a propromoter polynucleotide, and RNA transcription, whereby multiple copies of the nucleic acid sequence of interest are generated.

In another aspect the invention provides methods for generating multiple copies of a nucleic acid sequence of interest, comprising: (a) combining: an RNA transcript comprising sequences complementary to the displaced primer extension products as described above; a second primer that is hybridizable to a sense RNA transcript comprising the sequence of interest; an RNA-dependent DNA polymerase; an enzyme that cleaves RNA from an RNA/DNA hybrid; a propromoter polynucleotide comprising a propromoter and a region which hybridizes to a second primer extension product; and an RNA polymerase; and (b) incubating the mixture of step (a) under conditions that permit primer hybridization and extension, RNA cleavage, hybridization of a propromoter polynucleotide to a primer extension product to form a complex comprising a primer extension product and a propromoter polynucleotide, and RNA transcription, whereby multiple copies of the nucleic acid sequence of interest are generated.

In yet another aspect the invention provides methods for generating multiple copies of a nucleic acid sequence of interest, comprising: (a) combining: a first primer, wherein the first primer is a composite primer that is hybridizable to a target polynucleotide, and wherein the composite primer comprises an RNA portion and a 3' DNA portion; optionally a polynucleotide comprising a termination polynucleotide sequence that is hybridizable to a region of the target polynucleotide which is 5' with respect to hybridization of the composite primer to the target polynucleotide; a DNA-dependent DNA polymerase; an enzyme that cleaves RNA from an RNA/DNA hybrid; a propromoter polynucleotide comprising a propromoter and a region which hybridizes to a first primer extension product; an RNA polymerase; a second primer that is hybridizable to a sense RNA transcript comprising the sequence of interest; an RNA-dependent DNA polymerase; and a propromoter polynucleotide comprising a propromoter and a region which hybridizes to a second primer extension product; and (b) incubating the mixture of step (a) under conditions that permit primer hybridization and extension, RNA cleavage, displacement of a first primer extension product from a complex comprising a first primer extension product and target polynucleotide when its RNA is cleaved and a composite primer binds to the target polynucleotide in the complex, hybridization of a propromoter polynucleotide to a primer extension product to form a complex comprising a primer extension product and a propromoter polynucleotide, and RNA transcription, whereby multiple copies of the nucleic acid sequence of interest are generated.

In another aspect, the invention provides methods for generating multiple copies of a nucleic acid sequence of interest, comprising: (a) hybridizing a second primer to an RNA transcript, said RNA transcript produced by a process comprising (i) hybridizing a single stranded target polynucleotide comprising the nucleic acid sequence of interest with a first primer, wherein said first primer is a composite primer comprising an RNA portion and a 3' DNA portion; (ii) optionally hybridizing a polynucleotide comprising a termination polynucleotide sequence to a region of the target polynucleotide 5' with respect to hybridization of the first primer to the target polynucleotide; (iii) extending the first primer with a DNA-dependent DNA polymerase to generate a complex comprising a first primer extension product and target polynucleotide; (iv) cleaving the RNA portion from the composite primer in the complex of first primer extension product and target polynucleotide with an enzyme that cleaves RNA from an RNA/DNA hybrid such that another composite primer (which is generally and preferably the same as the first primer) can hybridize to the target polynucleotide and repeat primer extension by strand displacement to produce displaced primer extension product; (v) hybridizing a propromoter polynucleotide comprising a propromoter and a region which hybridizes to the displaced primer extension product under conditions which allow transcription to occur by RNA polymerase (these conditions generally but not necessarily include extension of the 3' end of the primer extension product to generate a double stranded promoter region), such that an RNA transcript comprising sequences complementary to the displaced primer extension product is produced; and (b) extending the second primer with RNA-dependent DNA polymerase to generate a complex comprising a second primer extension product and the RNA transcript; (c) cleaving RNA in the complex of step (b) with an enzyme that cleaves RNA in an RNA/DNA hybrid; (d) hybridizing the single stranded second primer extension product with a propromoter polynucleotide, wherein the propromoter polynucleotide comprises a propromoter and a region which hybridizes to the single stranded second primer extension product under conditions which allow transcription to occur by RNA polymerase (these conditions generally but not necessarily include extension of the 3' of the primer extension product to generate a double stranded promoter region), such that an RNA transcript comprising the sequence of interest is produced; whereby multiple copies of the nucleic acid sequence of interest are produced.

Various embodiments of the composite primer used in the composite primer-based methods of the invention are described herein. For example, in some embodiments, the RNA portion of the composite primer is 5' with respect to the 3' DNA portion. In still other embodiments, the 5' RNA portion is adjacent to the 3' DNA portion. For the composite primer-based methods described herein, one or more composite primers can be used. In preferred embodiments of the composite primer-based methods, the first and second primers are different (for example, the first primer is a composite primer and the second primer is not a composite primer). In preferred embodiments wherein the first and second primers are different, the primers are hybridizable to similar, preferably identical, sequences. In still other embodiments of the composite primer-based methods, the first and second primers are hybridizable to different sequences.

Various exemplary embodiments of polynucleotides comprising a termination sequence are also described herein. In some embodiments, the polynucleotide comprising a termination sequence is a template switch oligonucleotide (TSO), which may (but not necessarily) contain one or more modifications to enhance binding to template. Accordingly, in some embodiments, the TSO comprises a modification in the region which hybridizes to the template, wherein, under a given set of conditions, the TSO binds more tightly to the region as compared to a TSO without the modification. Examples of suitable modifications are provided herein. In some embodiments, the polynucleotide comprising a termination sequence is a blocking sequence, which, like the TSO, may contain one or more modifications to enhance binding to template. Accordingly, in some embodiments, the blocker sequence comprises a modification in the region which hybridizes to the template, wherein, under a given set of conditions, the blocker binds more tightly to the region as compared to a blocker without the modification. Examples of suitable modifications are provided herein.

The enzymes which may be used in the methods and compositions are described herein. For example, the enzyme that cleaves RNA may be an RNaseH.

In some aspects, a TSO provides propromoter function and also comprises a region (which may or may not be adjacent to the promoter) which hybridizes to the displaced primer extension product. In other embodiments, the polynucleotide comprising the propromoter comprises a region at the 3' end which hybridizes to the displaced primer extension product, whereby DNA polymerase extension of displaced extension product produces a double stranded promoter from which transcription occurs. In some embodiments, the polynucleotide comprising the propromoter is a propromoter template oligonucleotide (PTO). In some embodiments, the polynucleotide comprising the propromoter is a polynucleotide comprising: (a) a termination sequence that does not effect template switch under conditions wherein the termination sequence is hybridizable to a target polynucleotide; (b) a propromoter sequence, wherein the propromoter sequence is not hybridizable to a target polynucleotide under conditions wherein the termination sequence is hybridizable to the target polynucleotide; and (c) a sequence which is hybridizable to a complementary sequence of said target polynucleotide.

In another aspect the invention provides methods for generating multiple copies of a nucleic acid sequence of interest, comprising: (a) hybridizing a single stranded target polynucleotide comprising the sequence of interest with a first primer; (b) hybridizing a propromoter template switch oligonucleotide (TSO) comprising a propromoter sequence and a region that is hybridizable to a region of the target polynucleotide which is 5' with respect to hybridization of the first primer to the target polynucleotide; (c) extending the first primer with DNA polymerase such that a first primer extension product comprising a sequence complementary to the propromoter sequence of the propromoter TSO is produced, whereby a complex of first primer extension product, target polynucleotide and propromoter TSO is generated, wherein said complex comprises a double stranded promoter region; (d) transcribing from the double stranded promoter region with a DNA-dependent RNA polymerase to generate a sense RNA transcript; (e) hybridizing a second primer (which is generally and preferably the same as the first primer) to the sense RNA transcript of step (d); (f) extending the second primer with RNA-dependent DNA polymerase to generate a complex comprising a second primer extension product and an RNA transcript; (g) cleaving RNA in the complex of step (f) with an enzyme that cleaves RNA in an RNA/DNA hybrid; (h) hybridizing a single stranded second primer extension product with a propromoter polynucleotide, wherein the propromoter polynucleotide comprises a propromoter and a region which hybridizes to the single stranded second primer extension product under conditions which allow transcription to occur by RNA polymerase, such that sense RNA transcripts comprising the sequence of interest are produced; whereby multiple copies of the nucleic acid sequence of interest are produced.

In another aspect the invention provides methods for generating multiple copies of a nucleic acid sequence of interest, comprising: (a) combining: the complex described above of a first primer extension product, target polynucleotide and propromoter TSO, wherein said complex comprises a double stranded promoter region; an RNA polymerase; a second primer (which is generally and preferably the same as the first primer) that is hybridizable to a sense RNA transcript comprising the sequence of interest; an RNA-dependent DNA polymerase; an enzyme that cleaves RNA from an RNA/DNA hybrid; and a propromoter polynucleotide comprising a propromoter and a region which hybridizes to a second primer extension product; and (b) incubating the mixture of step (a) under conditions that permit primer hybridization and extension, RNA cleavage, hybridization of a propromoter polynucleotide to a primer extension product to form a complex comprising a primer extension product and a propromoter polynucleotide, and RNA transcription, whereby multiple copies of the nucleic acid sequence of interest are generated.

In another aspect the invention provides methods for generating multiple copies of a nucleic acid sequence of interest, comprising: (a) combining: a sense RNA transcript generated as described above; a second primer (which is generally and preferably the same as the first primer) that is hybridizable to the RNA transcript; an RNA-dependent DNA polymerase; an enzyme that cleaves RNA from an RNA/DNA hybrid; a propromoter polynucleotide comprising a propromoter and a region which hybridizes to a second primer extension product; and an RNA polymerase; and (b) incubating the mixture of step (a) under conditions that permit primer hybridization and extension, RNA cleavage, hybridization of a propromoter polynucleotide to a primer extension product to form a complex comprising a primer extension product and a propromoter polynucleotide, and RNA transcription, whereby multiple copies of the nucleic acid of interest are generated.

In another aspect the invention provides methods for generating multiple copies of a nucleic acid sequence of interest, comprising: (a) combining: a target polynucleotide; a first primer which is hybridizable to the target polynucleotide; a propromoter template switch oligonucleotide comprising a propromoter sequence and a region that is hybridizable to a region of the target polynucleotide which is 5' with respect to hybridization of the first primer to the target polynucleotide; optionally a DNA-dependent DNA polymerase; an RNA polymerase; a second primer (which is generally and preferably the same as the first primer) that is hybridizable to a sense RNA transcript comprising the sequence of interest; an RNA-dependent DNA polymerase; an enzyme that cleaves RNA from an RNA/DNA hybrid; and a propromoter polynucleotide comprising a propromoter and a region which hybridizes to a second primer extension product; and (b) incubating the mixture of step (a) under conditions that permit primer hybridization and extension, RNA cleavage, hybridization of a propromoter polynucleotide to a primer extension product to form a complex comprising a primer extension product and a propromoter polynucleotide, and RNA transcription, whereby multiple copies of the nucleic acid sequence of interest are generated.

In another aspect, the invention provides methods for generating multiple copies of a nucleic acid sequence of interest, comprising: (a) hybridizing a second primer to an RNA transcript, said RNA transcript produced by a process comprising (i) hybridizing a single stranded target polynucleotide comprising the sequence of interest with a first primer (which is generally and preferably the same as the second primer); (ii) hybridizing a propromoter template switch oligonucleotide (TSO) comprising a propromoter sequence and a region that is hybridizable to a region of the target polynucleotide which is 5' with respect to hybridization of the first primer to the target polynucleotide; (iii) extending the first primer with DNA polymerase such that a first primer extension product comprising a sequence complementary to the propromoter sequence of the propromoter TSO is produced, whereby a complex of first primer extension product, target polynucleotide and propromoter TSO is generated, wherein said complex comprises a double stranded promoter region; (iv) transcribing from the double stranded promoter region with a DNA-dependent RNA polymerase to generate a sense RNA transcript; (b) extending the second primer with RNA-dependent DNA polymerase to generate a complex comprising a second primer extension product and an RNA transcript; (c) cleaving RNA in the complex of step (b) with an enzyme that cleaves RNA in an RNA/DNA hybrid; (d) hybridizing a single stranded second primer extension product with a propromoter polynucleotide, wherein the propromoter polynucleotide comprises a propromoter and a region which hybridizes to the single stranded second primer extension product under conditions which allow transcription to occur by RNA polymerase, such that sense RNA transcripts comprising the sequence of interest are produced; whereby multiple copies of the nucleic acid sequence of interest are produced.

In preferred embodiments of the propromoter TSO-based methods, the first primer and the second primer are the same. In other embodiments of the propromoter TSO-based methods, the first and second primers are different. In certain embodiments wherein the first and second primers are different, the primers are hybridizable to similar, preferably identical, sequences. In still other embodiments of the propromoter TSO-based methods, the first and second primers are hybridizable to different sequences.

The methods are applicable to amplifying any DNA or RNA target, including, for example, genomic DNA or RNA and cDNA. One or more steps may be combined and/or performed sequentially (often in any order, as long as the requisite product(s) are formed).

The invention also provides methods which employ (usually, analyze) the products of the amplification methods of the invention, such as sequencing and detection of sequence alteration(s). A method of sequencing according to the invention comprises: (a) amplifying a target polynucleotide by the methods of the invention in the presence of a mixture of rNTPs and rNTP analogs such that transcription is terminated upon incorporation of an rNTP analog; and (b) analyzing the amplification products to determine sequence.

Another method of sequencing according to the invention comprises: (a) amplifying a target polynucleotide by the methods of the invention wherein RNA transcripts generated from a first primer extension product are amplified in the presence of a mixture of rNTPs and rNTP analogs such that transcription is terminated upon incorporation of an rNTP analog; and (b) analyzing the amplification products to determine sequence. Another method of sequence analysis according to the invention comprises: (a) amplifying a target polynucleotide by the methods of the invention; and (b) analyzing the amplification products for single stranded conformation, wherein a difference in conformation as compared to a reference single stranded polynucleotide indicates a mutation in the target polynucleotide sequence.

The invention provides methods of characterizing a sequence of interest in a target polynucleotide comprising (i) amplifying a target polynucleotide sequence containing the sequence of interest by the methods of the invention, wherein the sequence of the RNA portion of the composite primer is known, and (ii) comparing the amplification products if any from step (i) with the amount of amplification products from a reference template wherein (1) production of detectably fewer amplification products from the template as compared to the amount of amplification products from the reference template which comprises a region complementary to the RNA portion of the composite primer indicates that the target polynucleotide does not comprise a sequence complementary to the RNA portion of the composite primer and is a sequence variant with respect to the sequence complementary to the RNA portion of the composite primer; or (2) production of detectably more amplification products from the template as compared to the amount of amplification products from the reference template which does not comprise a region which is complementary to the RNA portion of the composite primer indicates that the target polynucleotide comprises a sequence complementary to the RNA portion of the composite primer and is not a sequence variant with respect to the sequence complementary to the RNA portion of the composite primer.

In the methods of the invention the sequence of the RNA portion of the composite primer may comprise a sequence complementary to the sequence of interest which may be a wild type sequence, a mutant sequence, or an allelic variant sequence.

The methods of the invention are useful for detection and quantification of a target nucleic acid sequence.

For example, in one aspect, the invention provides methods of sequencing a sequence of interest comprising sequencing a nucleic acid amplification product, wherein said nucleic acid amplification product is generated by an amplification method described herein. Sequencing of the amplification products reveals the sequence of the sequence of interest.

In yet another example, the invention provides methods of detecting presence of a nucleic acid sequence of interest in a sample, said method comprising detecting presence of the sequence of interest in a nucleic acid amplification product generated by an amplification method described herein. Detection of the sequence of interest in the amplification products is indicative of presence of the sequence of interest in a sample.

In various embodiments of methods of the invention, a sequence of interest comprises a mutation. In some embodiments wherein a sequence of interest comprises a mutation, the mutation is a single nucleotide polymorphism. In some embodiments, detecting of a sequence of interest comprises hybridizing an amplification product comprising the sequence of interest with a nucleic acid probe that is hybridizable to said nucleic acid sequence of interest. In other embodiments, detecting of a sequence of interest comprises hybridizing an amplification product comprising the complement of the sequence of interest with a nucleic acid probe that is hybridizable to said complement. In some embodiments, a nucleic acid probe comprises DNA. In other embodiments, a nucleic acid probe comprises RNA. In some embodiments, a probe is provided as a microarray. In some embodiments, a microarray comprises a probe immobilized on a substrate fabricated from a material selected from the group consisting of paper, glass, plastic, polypropylene, nylon, polyacrylamide, nitrocellulose, silicon, and optical fiber. In some embodiments, a sequence of interest or its complement is detected by conducting limited primer extension, wherein the limited primer extension comprises extending a primer hybridized to an amplification product such that a primer extension product is generated that has a characteristic that indicates presence or absence of the sequence of interest.

Thus, the methods of the invention are useful for detection and quantification of a target nucleic acid sequence. The single-stranded nucleic acid amplification products of the invention can also be used for the detection and quantification of a target nucleic acid sequence by hybridization to probes, such as immobilized probes. The invention also provides methods of producing a microarray, comprising (a) amplifying a target polynucleotide by the methods of the invention; and (b) immobilizing the amplification products on a substrate to fabricate a microarray comprising the amplification products.

One aspect of the invention provides methods of determining gene expression profile in a sample comprising: (a) amplifying at least two sequences of interest in the sample by the methods of the invention; and (b) determining amount of amplification products of each sequence of interest, wherein each said amount is indicative of amount of each sequence of interest in the sample, whereby the gene expression profile in the sample is determined. In one embodiment each target polynucleotide is a cDNA. In another embodiment each target polynucleotide is RNA.

The invention also provides compositions, kits, complexes, reaction mixtures and systems comprising various components (and various combinations of the components) used in the amplification methods described herein. One aspect of the invention provides a system for amplifying a sequence of interest, comprising: (a) a first primer which is a composite primer; (b) a second primer; (c) a DNA-dependent DNA polymerase; (d) an RNA-dependent DNA polymerase; (e) a propromoter polynucleotide; (f) an RNA polymerase; and (g) an enzyme that cleaves RNA from an RNA/DNA hybrid; and optionally, (h) a polynucleotide comprising a termination polynucleotide sequence. Another aspect of the invention provides a system for amplifying a sequence of interest, comprising: (a) a propromoter TSO; (b) a first primer; (c) optionally a DNA-dependent DNA polymerase; (d) an RNA-dependent DNA polymerase; (e) an enzyme that cleaves RNA from an RNA/DNA hybrid; (f) an RNA polymerase; and optionally (g) a second primer.

In another aspect, the invention provides reaction mixtures (or compositions comprising reaction mixtures) which contain various combinations of components described herein. In another aspect, the invention provides kits for conducting the methods described herein. These kits, in suitable packaging and generally (but not necessarily) containing suitable instructions, contain one or more components used in the amplification methods. For example, the invention provides kits that comprise a composite primer (for example, comprising a 3' DNA portion and an RNA portion, which may be 5' and may further be adjacent to the 3' DNA portion) that is hybridizable to a target polynucleotide, a propromoter polynucleotide, and instructions for amplifying the target polynucleotide according to any composite primer-based method described herein. The composite primer and propromoter polynucleotide in the kits can be any described herein. The kits can contain further components, such as any of (a) a polynucleotide comprising a termination polynucleotide sequence; (b) any of the enzymes described herein, such as an enzyme which cleaves RNA from an RNA/DNA hybrid (for example, RNaseH); (c) a propromoter TSO; and (d) a second primer. In another example, the invention provides kits comprising a propromoter TSO and a first primer (which may or may not be a composite primer), wherein both are hybridizable to a target polynucleotide, and instructions for amplifying the target polynucleotide according to any propromoter TSO-based method described herein. The kits can contain further components, such as any of (a) any of the enzymes described herein, such as an enzyme which cleaves RNA from an RNA/DNA hybrid (for example, RNaseH); (b) a polynucleotide comprising a propromoter and a region which hybridizes to a second primer extension product; and (c) optionally a second primer.

BRIEF DESCRIPTION OF THE DRAWINGS

FIGS. 1A-F is a diagrammatic representation of the steps of a composite primer isothermal amplification process using a blocker sequence component as a termination polynucleotide.

FIGS. 2A-E is a diagrammatic representation of the steps of a composite primer isothermal amplification process using a template switch oligonucleotide sequence as a termination polynucleotide.

MODES FOR CARRYING OUT THE INVENTION

Figure 1A:
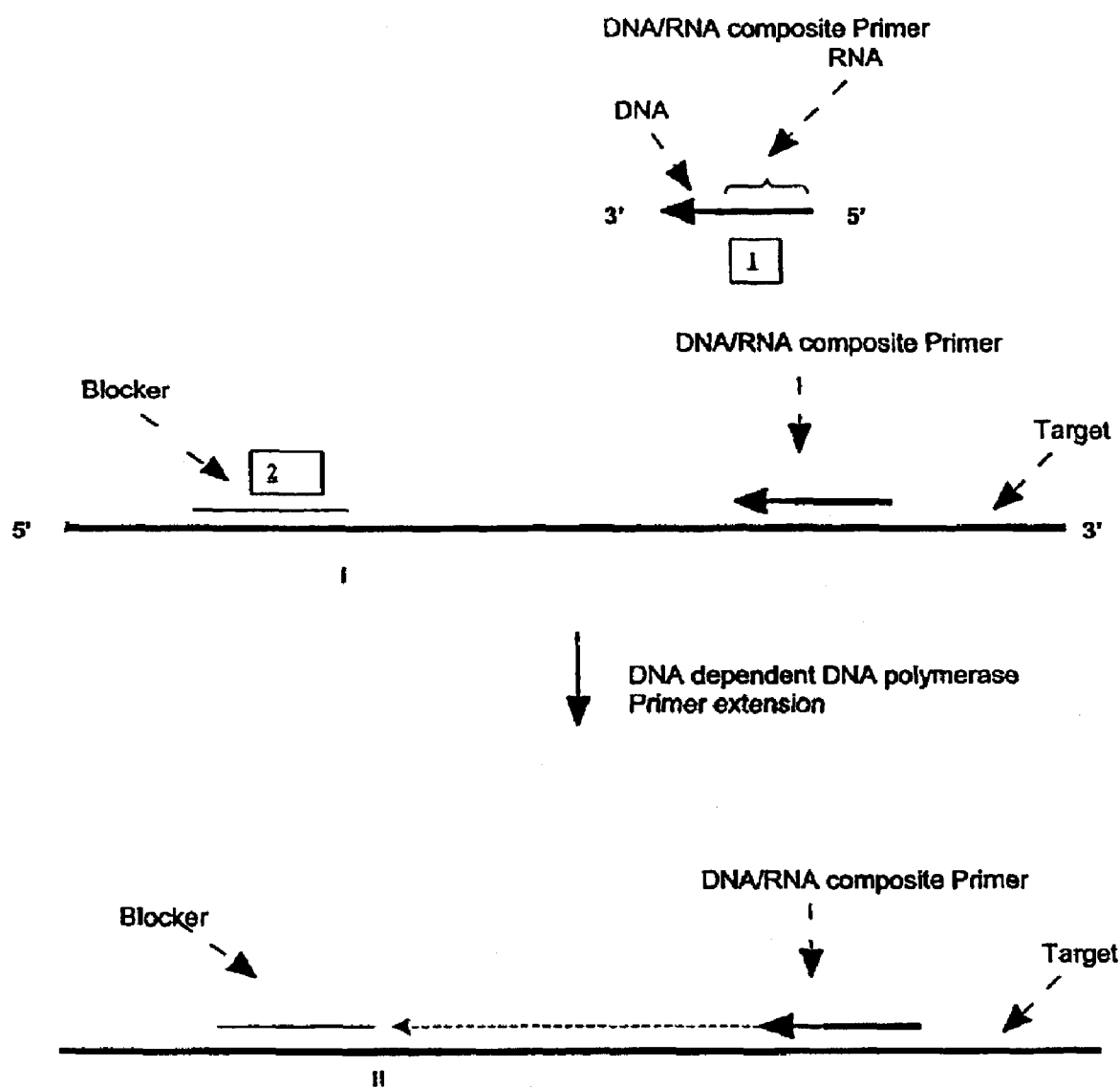

The invention provides methods, compositions and kits for amplifying nucleic acid sequences. Amplification of target nucleic acid sequence can be advantageous in many instances, for example in cases where the target polynucleotide is present in very small quantities, or where only a few molecules of a target polynucleotide is available, or for the purpose of nucleotide sequence determination of a defined target nucleic acid.

In one aspect, the invention provides methods generally using an RNA/DNA composite primer and two sets or rounds of transcription steps (each set or round referred to herein as a "transcription module") based on hybridization of a propromoter polynucleotide to intermediate polynucleotides. In another aspect, the invention provides methods comprising using, in a first transcription module, a propromoter template switch oligonucleotide to generate an intermediate polynucleotide complex capable of being transcribed to generate sense RNA transcripts and, in a second transcription module, further amplifying the RNA transcripts of the first transcription module by transcription.

In one aspect, the amplification methods generally work as follows: a composite RNA/DNA primer and a first propromoter polynucleotide form the basis for transcription of a target polynucleotide in the first transcription module. In some embodiments, a termination sequence provides an endpoint for the replication by either diverting or blocking further replication along the target strand. Generally, the termination sequence comprises a sequence that is sufficiently complementary to hybridize to the target strand. As described below, in some embodiments a polynucleotide comprising a termination sequence is a template switch oligonucleotide (TSO) which comprises sequences that are not sufficiently complementary to hybridize to the target strand in addition to the sequences which are sufficiently complementary to hybridize. A DNA polymerase uses the primer to initiate copying of the target polynucleotide to generate a primer extension product. An enzyme (such as RNaseH) which cleaves RNA from an RNA/DNA hybrid cleaves (removes) RNA sequences from the hybrid of template strand and primer extension product, leaving a sequence on the template strand available for binding by another composite primer. A second strand is then produced by DNA polymerase, which displaces the previously replicated strand, resulting in a displaced extension product. A polynucleotide comprising a propromoter and a region which hybridizes to the displaced primer extension product (which can be, for example, a template switch oligonucleotide or propromoter template oligonucleotide) is hybridized to the displaced primer extension product.

If the primer extension product comprises a propromoter sequence, hybridization of a propromoter polynucleotide (such as a template switch oligonucleotide (TSO)) to this sequence generates a double stranded promoter region. Where the displaced primer extension product does not comprise a suitable propromoter sequence, a propromoter sequence is incorporated using a propromoter polynucleotide, such as a propromoter template oligonucleotide (PTO). A propromoter polynucleotide binds to the displaced primer extension product. The double stranded promoter that is created from the displaced primer extension product is used by a DNA-dependent RNA polymerase to produce sense RNA products (i.e., RNA which comprises the target sequence, as opposed to its complement). A second primer is then hybridized to the sense RNA transcript and extended by an RNA-dependent DNA polymerase to generate a complex of a second primer extension product and the sense RNA transcript. A ribonuclease that cleaves RNA in an RNA/DNA hybrid (such as RNaseH) cleaves the RNA in the complex. A propromoter polynucleotide is then hybridized to a single stranded second primer extension product such that a double stranded promoter region is created (which, as described herein, can arise directly via hybridization or indirectly via extension of the primer extension product along the propromoter polynucleotide). Transcription from the double stranded promoter region produces sense RNA transcripts comprising the sequence of interest.

Accordingly, the invention provides methods of producing at least one copy of a nucleic acid sequence of interest (generally, methods of amplifying a target polynucleotide sequence) comprising combining and reacting the following: (a) a single-stranded target polynucleotide comprising a target sequence; (b) a first primer, which is a composite primer comprising an RNA portion and a 3' DNA portion; (c) a DNA polymerase; (d) deoxyribonucleoside triphosphates or suitable analogs; (e) an enzyme, such as RNaseH, which cleaves RNA from an RNA/DNA duplex; (f) optionally a polynucleotide comprising a termination sequence, such as any of those described herein, which comprises a portion (or region) which hybridizes to the template polynucleotide; (g) a polynucleotide comprising a propromoter sequence (which can be in any of a number of forms, as described herein) and a region which hybridizes to the displaced primer extension product; (h) ribonucleoside triphosphates or suitable analogs; (i) a second primer (which may or may not be the same as the first primer; and (j) RNA polymerase, under conditions such that transcription of the displaced strand can occur. The combination is subjected to suitable conditions such that (a) the composite primer (and, optionally, a polynucleotide comprising a termination sequence) hybridizes to the template; (b) primer extension occurs from the composite primer, to form a duplex; (c) RNaseH cleaves RNA of the composite primer from the RNA/DNA duplex; (d) another composite primer (which is generally and preferably the same as the first primer) hybridizes to the template, and another round of primer extension (mediated by DNA polymerase) occurs, displacing the strand already copied from the template; (e) transcription occurs to generate RNA transcripts complementary to a composite primer extension product; (f) a second primer hybridizes to the RNA transcript of step (e); (g) primer extension occurs from the second primer, to form a duplex; (h) a ribonuclease such as RNaseH cleaves RNA from the duplex of step (g); (i) a propromoter polynucleotide hybridizes to the single stranded second primer extension product that is generated by step (h) such that a double stranded promoter region is generated (either directly or indirectly as described herein); and (j) transcription occurs to generate sense RNA transcripts comprising the sequence of interest. Optional repetition of the second set of transcription steps using the sense transcripts of step (j) as the starting substrate (to which the second primer would hybridize) results in exponential amplification of the sequence of interest.

It is understood that, with respect to the combinations described herein, it is not necessary to react all components in the same vessel and/or simultaneously. Accordingly, the invention provides subcombinations, as long as the subcombinations expressly or implicitly reflect the amplification manipulations/methods described herein.

In another aspect, as a general summary, the amplification methods work as follows: template switching during extension of a first primer due to a propromoter TSO that is hybridized 5' with respect to the hybridization site of the first primer on a target polynucleotide results in generation of a polynucleotide complex that comprises a double stranded promoter region. The propromoter TSO comprises a sequence hybridizable (i.e., that hybridizes) to the target polynucleotide, and a sequence that is not hybridizable (i.e., does not hybridize under conditions that permit hybridization of the hybridizable sequence) to the target polynucleotide, wherein the sequence that is not hybridizable comprises a propromoter sequence. In a first transcription module, extension of the first primer along the target polynucleotide sequence is switched to the non-hybridizable sequence of the propromoter TSO at the point where the TSO is hybridized to the target polynucleotide. In some embodiments wherein the target polynucleotide is RNA, the RNA is cleaved following first primer extension. In other embodiments wherein the target polynucleotide is RNA, the RNA is not cleaved following first primer extension. The complex of the primer extension product and the non-hybridizable sequence of the TSO comprises a double stranded promoter region. Transcription occurs from the double stranded promoter region to generate sense RNA transcripts. In a second transcription module, these sense RNA transcripts are subjected to further amplification. In the second module, a second primer (which is generally and preferably the same as the first primer) is hybridized to a sense RNA transcript and extended by an RNA-dependent DNA polymerase to generate a complex of a second primer extension product and the sense RNA transcript. A ribonuclease that cleaves RNA in an RNA/DNA hybrid (such as RNaseH) cleaves RNA in the complex. A propromoter polynucleotide is then hybridized to a single stranded second primer extension product such that a double stranded promoter region is created (either directly or indirectly, as described herein). Transcription from the double stranded promoter region produces sense RNA transcripts comprising the sequence of interest.

Accordingly, the invention provides methods of producing at least one copy of a nucleic acid sequence of interest (generally, methods of amplifying target polynucleotide sequence) comprising combining and reacting the following: (a) a single stranded target polynucleotide; (b) a first primer that is hybridizable to the target polynucleotide at a location 3' of the sequence of interest; (c) a propromoter TSO; (d) a DNA polymerase; (e) deoxyribonucleoside triphosphates or suitable analogs; (f) an RNA polymerase; and (g) ribonucleoside triphosphates or suitable analogs; (h) a second primer (which is generally and preferably the same as the first primer) that is hybridizable to an RNA transcript produced in the first transcription step; (i) an enzyme, such as RNaseH, which cleaves RNA from an RNA/DNA duplex; (j) a propromoter polynucleotide (which can be in any of a number of forms, as described herein) which hybridizes to a second primer extension product. The combination is subjected to suitable conditions such that: (a) the first primer and propromoter TSO hybridize to the target polynucleotide; (b) primer extension occurs from the first primer along the target polynucleotide, and the non-hybridizable sequence of the propromoter TSO following template switching, to form a complex comprising a double stranded promoter region; (c) transcription occurs from the double stranded promoter region of step (b); and (d) a second primer (which is generally and preferably the same as the first primer) hybridizes to the RNA transcript of step (c); (e) primer extension occurs from the second primer, to form a duplex; (f) a ribonuclease such as RNaseH cleaves RNA from the duplex of step (e); (g) a propromoter polynucleotide hybridizes to a single stranded second primer extension product such that a double stranded promoter region is generated (either directly or indirectly, as described herein); and (h) transcription occurs to generate sense transcripts comprising the sequence of interest.

Any of the methods of the invention can be used to generate RNA products that are labeled by incorporating labeled nucleotides into appropriate steps of the methods. These labeled products are particularly suitable for quantification and/or identification of the nucleic acids by methods known in the art, which include the use of arrays such as cDNA microarrays and oligonucleotide arrays.

In some embodiments, the invention provides methods of sequencing a nucleic acid sequence of interest. For sequencing methods based on methods described herein, the appropriate rNTPs, or analogs thereof, which may be labeled or unlabelled, are used. Accordingly, the invention provides methods of sequencing a target polynucleotide comprising a sequence of interest based on the methods described above, wherein rNTPs and rNTP analogs, which may be labeled or unlabelled primer elongation terminators, are used and the amplification products are analyzed for sequence information, as described below. Sequencing by transcription can be used for both DNA and RNA target sequences using rNTPs and rNTP analogs.

The invention provides methods of detecting nucleic acid sequence mutations in target sequence(s). In one embodiment of the composite primer-based methods, the presence or absence of a mutation in a target polynucleotide is detected based on the ability to amplify the target polynucleotide using a composite primer whose RNA portion either contains or lacks the mutated sequence using the methods of the invention. The amplified products of the methods of the invention can also be characterized for sequences of interest. For example, the amplification products can be sequenced to determine a sequence of interest. They can also be used for detection of mutations, such as by hybridization with specific probes. The amplified products can also be used to detect and/or identify sequence alterations or single nucleotide polymorphisms in the target nucleic acid sequence by determining single strand conformation polymorphisms. Thus, the invention provides methods to characterize (for example, detect and/or quantify) a sequence of interest by generating RNA products using amplification methods of the invention, and analyzing the products by detection/quantification methods such as those based on array technologies or solution phase technologies. Generally, but not necessarily, these amplified products are labeled.

In yet another embodiment, the invention provides methods for generating microarrays of nucleic acids (RNA) using products of the amplification methods of the invention.

Details regarding the various components of the methods of the present invention are provided below.

General Techniques

The practice of the present invention employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", 2d. edition (Sambrook et al., (1989)); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., (1987)), and periodic updates); "PCR: The Polymerase Chain Reaction", (K. Mullis et al., eds., (1994)).

Primers, oligonucleotides and polynucleotides employed in the present invention can be generated using standard techniques known in the art. The primers of the present invention can be prepared by methods known in the art. Preferably, the primers are synthesized by chemical methods. For example, Caruthers et al. (Methods In Enzymology, vol. 154, p. 287 (1987)) describe using standard phosphoramidite solid-phase chemistry to join nucleotides by phosphodiester linkages.

Definitions

A "target polynucleotide," as used herein, is a polynucleotide known or suspected of comprising a nucleic acid sequence of interest, for which amplification is desired. The nucleic acid sequence of interest may be known or not known, in terms of its actual sequence. Generally, a "template," as used herein, is a polynucleotide that contains a nucleic acid sequence of interest. In some instances, the terms "target sequence," "template DNA," "template polynucleotide," "target nucleic acid," and variations thereof, are used interchangeably.

"Amplification," as used herein, generally refers to the process of producing multiple copies of a desired sequence. "Multiple copies" mean at least 2 copies. A "copy" does not necessarily mean perfect sequence complementarity or identity to the template sequence. For example, copies can include nucleotide analogs (such as deoxyinosine), intentional sequence alterations (such as sequence alterations introduced through a primer comprising a sequence that is hybridizable, but not complementary, to the template), and/or sequence errors that occur during amplification.

A "sense" polynucleotide (for example, a sense RNA transcript), as used herein, refers to a polynucleotide that comprises a sequence of interest from a target nucleic acid sequence as opposed to its complement.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, □-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "first transcription module," as used herein, refers to a process comprising steps of the methods up to and including the first transcription step. A "second transcription module," as used herein, refers to a process comprising steps of the methods starting from priming of the RNA transcript generated in the first transcription module to creating a DNA product up to and including the second transcription step.

A "labeled rNTP," as used herein, refers, respectively, to an rNTP, or analogs thereof, that is directly or indirectly attached with a label. For example, a "labeled" rNTP may be directly labeled with, for example, a dye and/or a detectable moiety, such as a member of a specific binding pair (such as biotin-avidin). A "labeled" rNTP may also be indirectly labeled by its attachment to, for example, a moiety to which a label is/can be attached. An rNTP may also comprise a moiety (for example, an amine group) to which a label may be attached following incorporation of the rNTP into an extension product. Useful labels in the present invention include fluorescent dyes (e.g., fluorescein isothiocyanate, Texas red, rhodamine, green fluorescent protein and the like), radioisotopes (e.g., 3H, 35S, 32P, 33P, 125I, or 14C), enzymes (e.g., lacZ, horseradish peroxidase, alkaline phosphatase, digoxigenin) and colorimetric labels such as colloidal gold or colored glass or plastic (e.g., polystyrene, polypropylene, latex, etc.) beads. Various anti-ligands and ligands can be used (as labels themselves or as a means for attaching a label). In the case of a ligand that has a natural anti-ligand, such as biotin, thyroxine and cortisol, the ligand can be used in conjunction with labeled anti-ligands.

The "type" of rNTP, as used herein, refers to the particular base of a nucleotide, namely adenine, cytosine, uridine, or guanine.

"Oligonucleotide," as used herein, generally refers to short, generally single stranded, generally synthetic polynucleotides that are generally, but not necessarily, less than about 200 nucleotides in length. Oligonucleotides in the present invention include the composite primer, TSO, PTO and blocker sequence. The terms "oligonucleotide" and "polynucleotide" are not mutually exclusive. The description above for polynucleotides is equally and fully applicable to oligonucleotides.

A "primer" is generally a nucleotide sequence, generally with a free 3'-OH group, that hybridizes with a template sequence (such as a target RNA, or a primer extension product) and is capable of promoting polymerization of a polynucleotide complementary to the template. A "primer" can be, for example, an oligonucleotide. It can also be, for example, a sequence of the template (such as a primer extension product) that is hybridized to a sequence in the template itself (for example, as a hairpin loop), and that is capable of promoting nucleotide polymerization.

A "random primer," as used herein, is a primer that comprises a sequence that is designed not based on a particular or specific sequence in a sample, but rather is based on a statistical expectation that the sequence (of the random primer) is hybridizable (under a given set of conditions) to one or more sequences in the sample. The sequence of a random primer (or its complement) may or may not be naturally existing, or present in a pool of sequences in a sample of interest. The amplification of a plurality of RNA species in a single reaction mixture would generally employ a multiplicity, preferably a large multiplicity, of random primers. As is well understood in the art, a "random primer" can also refer to a primer that is a member of a population of primers (a plurality of random primers) which collectively are designed to hybridize to a desired and/or a significant number of target sequences. A random primer may hybridize at a plurality of sites on a nucleic acid sequence. The use of random primers provides a method for generating primer extension products complementary to a target polynucleotide by a polymerase which does not require prior knowledge of the exact sequence of the target.

A "termination polynucleotide sequence" or "termination sequence," as used interchangeably herein, is a polynucleotide sequence which effects cessation of DNA replication by DNA polymerase with respect to the template comprising the target sequence. A termination sequence comprises a portion (or region) that generally hybridizes to the template at a location 5' to the termination point (site). The hybridizable portion may or may not encompass the entire termination sequence. Examples of suitable termination polynucleotide sequences (such as blocker sequences and TSOs) are provided herein. Other examples of suitable termination polynucleotide sequences include a combination polynucleotide comprising a termination sequence (which generally and preferably does not effect template switch under conditions in which the termination sequence is hybridizable to a target polynucleotide) and a propromoter sequence, as described herein.

"Blocker sequence," or "blocking sequence" as used interchangeably herein, is an example of a termination sequence, and refers to an oligonucleotide that binds, generally with high affinity, to the template nucleic acid at a location 5' to the termination site and effects cessation of DNA replication by DNA polymerase with respect to the template comprising the target sequence. Its 3' end may or may not be blocked for extension by DNA polymerase.

"Termination site," or "termination point," as used interchangeably herein, refers to the site, point or region of the template that is last replicated by the DNA polymerase before termination of polymerization (generally, primer extension) or template switch. For example, with respect to a TSO, it is the position or region in the target sequence that is complementary to the 3' end of the primer extension product prior to switching template from the template polynucleotide to the unhybridized portion of the TSO.

"Protopromoter sequence," and "propromoter sequence," as used herein, refer to a single-stranded DNA sequence region which, in double-stranded form is capable of mediating RNA transcription. In some contexts, "protopromoter sequence," "protopromoter," "propromoter sequence," "propromoter," "promoter sequence," and "promoter" are used interchangeably. A propromoter sequence may be provided by any of the propromoter polynucleotides described herein, for example TSO, PTO, or a combination polynucleotide comprising a termination sequence (which generally and preferably does not effect template switch under conditions in which the termination sequence is hybridizable to a target polynucleotide) and a propromoter sequence, as described herein.

"Template switch oligonucleotide," "target switch oligonucleotide" or "TSO," as used herein, refers to an oligonucleotide that comprises a portion (or region) that is hybridizable to a template at a location 5' to the termination site of primer extension and that is capable of effecting a template switch in the process of primer extension by a DNA polymerase, generally due to a sequence that is not hybridized to the template. TSOs are generally known in the art. "Template switch" refers to a change in template nucleic acid, generally from the target nucleic acid to the unhybridized portion of a TSO, during the course of a single round of primer extension.

A "propromoter TSO," as used herein, is a TSO that further comprises a propromoter sequence that is not hybridizable to a target polynucleotide (under a given set of conditions, which are generally those in effect when the hybridizable portion or region of the TSO is hybridized to the target). The propromoter sequence is generally, but not necessarily, in the 5' region of the TSO.

"Propromoter template oligonucleotide (PTO)," as used herein, refers to an oligonucleotide that comprises a propromoter sequence and a portion, generally a 3' portion, that is hybridizable to the 3' region of a primer extension product. The propromoter sequence and the hybridizable portion may be the same, distinct or overlapping nucleotides of an oligonucleotide.

A first sequence which "corresponds" to a second sequence, such as an RNA portion of a composite primer, means that the first sequence has significant sequence identity with respect to the second sequence. This term is generally used in the context of detecting mutations, or characterizing sequences of a target.

To "inhibit" is to decrease or reduce an activity, function, and/or amount as compared to a reference.

A "complex" is an assembly of components. A complex may or may not be stable and may be directly or indirectly detected. For example, as is described herein, given certain components of a reaction, and the type of product(s) of the reaction, existence of a complex can be inferred. For purposes of this invention, a complex is generally an intermediate with respect to the final amplification product(s).

A "portion" or "region," used interchangeably herein, of a polynucleotide or oligonucleotide is a contiguous sequence of 2 or more bases. In other embodiments, a region or portion is at least about any of 3, 5, 10, 15, 20, 25 contiguous nucleotides.

A region, portion, or sequence which is "adjacent" to another sequence directly abuts that region, portion, or sequence. For example, an RNA portion which is adjacent to a 5' DNA portion of a composite primer directly abuts that region. For an illustration of this example, see FIG. 1A-C.

A "reaction mixture" is an assemblage of components, which, under suitable conditions, react to form a complex (which may be an intermediate) and/or a product(s).

"A", "an" and "the", and the like, unless otherwise indicated include plural forms.

"Comprising" Means Including.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in a sequence of interest in comparison to a reference sequence. A reference sequence can be a wild type sequence or a sequence to which one wishes to compare a sequence of interest. A sequence mutation includes single nucleotide changes, or alterations of more than one nucleotide in a sequence, due to mechanisms such as substitution, deletion or insertion. Single nucleotide polymorphism (SNP) is also a sequence mutation as used herein.

"Single stranded conformation polymorphism," and "SSCP," as used herein, generally refers to the specific conformation of a single stranded nucleic acid as is affected by its specific nucleic acid sequence. Alteration of the sequence of the single stranded polynucleotide, such as single nucleotide substitution, deletions or insertions, results in change, or polymorphism, of the conformation of the single stranded polynucleotide. The conformation of the polynucleotide is generally detectable, identifiable and/or distinguishable using methods known in the art, such as electrophoretic mobility as measured by gel electrophoresis, capillary electrophoresis, and/or susceptibility to endonuclease digestion.

"Microarray" and "array," as used interchangeably herein, comprise a surface with an array, preferably ordered array, of putative binding (e.g., by hybridization) sites for a biochemical sample (target) which often has undetermined characteristics. In a preferred embodiment, a microarray refers to an assembly of distinct polynucleotide or oligonucleotide probes immobilized at defined positions on a substrate. Arrays are formed on substrates fabricated with materials such as paper, glass, plastic (e.g., polypropylene, nylon), polyacrylamide, nitrocellulose, silicon, optical fiber or any other suitable solid or semi-solid support, and configured in a planar (e.g., glass plates, silicon chips) or three-dimensional (e.g., pins, fibers, beads, particles, microtiter wells, capillaries) configuration. Probes forming the arrays may be attached to the substrate by any number of ways including (i) in situ synthesis (e.g., high-density oligonucleotide arrays) using photolithographic techniques (see, Fodor et al., Science (1991), 251:767-773; Pease et al., Proc. Natl. Acad. Sci. U.S.A. (1994), 91:5022-5026; Lockhart et al., Nature Biotechnology (1996), 14:1675; U.S. Pat. Nos. 5,578,832; 5,556, 752; and 5,510,270); (ii) spotting/printing at medium to low-density (e.g., cDNA probes) on glass, nylon or nitrocellulose (Schena et al, Science (1995), 270:467-470, DeRisi et al, Nature Genetics (1996), 14:457-460; Shalon et al., Genome Res. (1996), 6:639-645; and Schena et al., Proc. Natl. Acad. Sci. U.S.A. (1995), 93:10539-11286); (iii) by masking (Maskos and Southern, Nuc. Acids. Res. (1992), 20:1679-1684) and (iv) by dot-blotting on a nylon or nitrocellulose hybridization membrane (see, e.g., Sambrook et al., Eds., 1989, Molecular Cloning: A Laboratory Manual, 2nd ed., Vol. 1-3, Cold Spring Harbor Laboratory (Cold Spring Harbor, N.Y.)). Probes may also be noncovalently immobilized on the substrate by hybridization to anchors, by means of magnetic beads, or in a fluid phase such as in microtiter wells or capillaries. The probe molecules are generally nucleic acids such as DNA, RNA, PNA, and cDNA but may also include proteins, polypeptides, oligosaccharides, cells, tissues and any permutations thereof which can specifically bind the target molecules.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

The term "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide. The 3' most nucleotide(s) can be preferably from about 1 to about 20, more preferably from about 3 to about 18, even more preferably from about 5 to about 15 nucleotides.

The term "5'-DNA portion," "5'-DNA region," "5'-RNA portion," and "5'-RNA region," refer to the portion or region of a polynucleotide or oligonucleotide located towards the 5' end of the polynucleotide or oligonucleotide, and may or may not include the 5' most nucleotide(s) or moieties attached to the 5' most nucleotide of the same polynucleotide or oligonucleotide. The 5' most nucleotide(s) can be preferably from about 1 to about 20, more preferably from about 3 to about 18, even more preferably from about 5 to about 15 nucleotides.

"Detection" includes any means of detecting, including direct and indirect detection. For example, "detectably fewer" products may be observed directly or indirectly, and the term indicates any reduction (including no products). Similarly, "detectably more" product means any increase, whether observed directly or indirectly.

Amplification Methods

The following are examples of amplification methods of the invention. It is understood that various other embodiments may be practiced, given the general description provided. For example, reference to using a composite primer means that any of the composite primers described herein may be used.

In one aspect, the methods of the invention utilize two linked transcription modules: a first transcription module that provides a composite primer-based linear nucleic acid amplification that is transcription-based (also referred to herein as "enhanced linear amplification"), which is in turn linked to a second transcription module that enables further isothermal amplification of the amplification products of the first module. The methods of the invention generally utilize two primers, both of the same sense with respect to the target nucleic acid strand to be amplified. All amplification reactions can be isothermal, and do not require thermocycling.

In another aspect, methods for generating multiple copies of sense RNA transcripts of a nucleic acid of interest are based on using a propromoter template switch oligonucleotide (TSO) to generate an intermediate polynucleotide product capable of being transcribed in a first set of transcription steps (a first transcription module) to generate RNA transcripts that are further amplified through a second set of transcription steps (a second transcription module).

The products of the amplification methods can be detected by either homogenous or heterogeneous detection, including identification by size and/or migration properties in gel electrophoresis, or by hybridization to sequence-specific probes. The detection of the amplification product is indicative of the presence of the target nucleic acid. Quantitative analysis is also feasible. For example, by comparing the amount of product amplified from a test sample containing an unknown amount of a polynucleotide containing a target sequence to the product of amplification of a reference sample that has a known quantity of a polynucleotide that contains the target sequence, the amount of target sequence in the test sample can be determined. Further extensions of this amplification method to the analysis of sequence alterations and sequencing of target nucleic acids are also feasible, as described below.

As amounts of single stranded DNA amplification products increase, the level of components such as free TSO and/or other propromoter polynucleotides becomes limiting, thus controlling the total amplification capacity. This is an unique feature of the amplification methods of the invention wherein amounts of such components used in the process can be adjusted to fine tune amplification capacity for maximal detection potential which is advantageous for nucleic acid detection and quantification processes.

The ability to modulate the total amount of the amplification product as determined by the amount of components such as TSO in the reaction mixture can facilitate more accurate detection and/or quantification of target polynucleotides. Excessive amplification produced by other known amplification methods, such as PCR, NASBA, TMA, etc. can pose problems for detection and/or quantification using methods employing two or more detection probes. The "hook effect" from binding excess analyte is well known in the art and results in non-linearity and signal drop-offs leading to false negatives or reduced signal strengths relative to expected levels at high analyte concentrations. The present invention has the advantage of limiting the maximum amount of product generated as appropriate for the chosen method for detection of the amplified product.

Amplification methods of the invention have the additional advantage of being resistant to non-specific incorporation of a promoter sequence into primer extension products which can lead to non-specific amplification. In the composite primer-based methods, the promoter sequence is introduced by a TSO and/or another propromoter polynucleotide as described herein. In the propromoter TSO-based methods, the promoter sequence is introduced by a propromoter TSO in the first transcription module, and another propromoter polynucleotide which, as described herein, can be a TSO, in the second transcription module. In the first transcription module of the propromoter TSO-based methods, the formation of a double stranded functional promoter is dependent on primer extension and template switch. The formation of a functional promoter in the second module requires hybridization of the second primer extension product to a propromoter polynucleotide such as a propromoter TSO. The step of propromoter polynucleotide hybridization in the methods of the invention increases the specificity of the process. A non-specific extension product would not be likely to have a sequence (e.g., a 3' end sequence) which is complementary to a propromoter polynucleotide designed to be hybridizable to a particular sequence in a primer extension product.

The methods are applicable to amplification of either DNA or RNA target molecules. The amplification methods of the invention can be used for, for example, detection, quantification and sequencing of a target sequence.

Composite Primer-Based Amplification Methods

In one aspect, methods for generating multiple copies of sense RNA transcripts of a nucleic acid sequence of interest using composite primers are provided. The composite primer-based amplification methods of the invention provide for isothermal exponential amplification of a nucleic acid sequence of interest. The methods utilize a composite primer and generally a second primer which is generally, but not necessarily, non-composite. In one embodiment, the methods also employ a termination sequence, such as a blocker sequence (as described in Method 1) or a TSO (as described in Method 2). Methods 1 and 2 are described below.

The termination sequence (either TSO or blocker sequence component, if used) is added for generating a product with a defined 3'-end. In some embodiments, natural sequence(s) within the template 5' of the primer binding site inhibits nucleic acid polymerization such that termination of primer extension is achieved. Such natural sequences are known in the art (for example, GC rich sequences) or can be empirically determined. Use of a termination sequence is particularly beneficial when amplifying genomic DNA so as to provide a defined end for primer extension. When this feature is not desired, the isothermal amplification according to the methods of the invention can be carried out without a termination sequence.

The isothermal amplification utilizes three enzymes, a DNA polymerase, a ribonuclease such as RNaseH, and an RNA polymerase. One embodiment of method 1, which utilizes a blocker sequence, is illustrated in FIG. 1A-F. An embodiment of method 2, which utilizes a TSO, is illustrated in FIG. 2A-E.

The composite primer-based methods of the invention are generally designed to amplify a single stranded DNA target. When the target nucleic acid to be amplified is double stranded DNA, the target is first denatured to produce a single stranded target. Target denaturation may be carried out using methods known in the art, such as heat denaturation or alkali treatment. When the target is single stranded RNA, such as mRNA or viral RNA, the target is first transcribed to produce a cDNA target by methods known in the art.

The target polynucleotide is combined with a composite primer, DNA polymerase, a ribonuclease such as RNaseH and optionally, a blocker sequence component or a TSO, as described above. In one embodiment, each amplification reaction includes composite primers of identical sequence. In another embodiment, each amplification reaction includes a mixture of composite primer variants, wherein the variants represent two or more homologous but non-identical sequences, and wherein all are capable of hybridizing to the same target nucleic acid sequence. The complementarity is preferably at least about 50%, more preferably at least about 75%, and most preferably at least about 90%. Advantages of this embodiment include the ability to introduce different sequences of interest into the primer extension products. In yet another embodiment, each amplification reaction includes a mixture of composite primers, wherein the primers represent two or more non-identical sequences that are of low or no homology, and wherein the primers preferentially hybridize to different target nucleic acid sequences or different sites along the same target nucleic acid strand. Advantages of this embodiment include multiplex detection and/or analysis of target nucleic acids through amplification of a plurality of target nucleic acid species in a single amplification reaction.

Methods that utilize a blocker sequence (or that do not utilize a termination polynucleotide) result in the generation of a displaced primer extension product which when hybridized to a propromoter polynucleotide forms a complex, which is a substrate for the RNA polymerase. The methods that utilize a TSO result in the generation of a unique intermediate amplification product comprising target and template switch oligonucleotide (TSO)-related portions. The complex formed by the hybridization of a TSO to a displaced primer extension product is a substrate for transcription by the RNA polymerase, which generates an RNA product of the same sense as the initial target sequence.

Two exemplary embodiments of the composite primer-based methods are described below:

Method 1: Blocker Sequence-Based Polynucleotide Amplification

In some embodiments, blocker sequence-based amplification methods are provided. An illustrative embodiment is shown in FIGS. 1A-F.

FIGS. 1A-F illustrate an embodiment of the method that utilizes a composite primer, as described herein; a blocker sequence component which is either an oligonucleotide or an oligonucleotide analog which, as described herein, is further able to hybridize to a sequence on the same target nucleic acid strand as the single primer; and a third oligonucleotide, a promoter template (PTO) which, as described herein, comprises a 3'-portion which is able to hybridize (and is preferably complementary) to the 3'-end of the displaced extension product and a 5'-portion which includes a sequence of a DNA-dependent RNA polymerase promoter. As in the TSO described herein, the sequence immediately adjacent to the promoter sequence can be designed to provide for preferably optimal transcriptional activity by the RNA polymerase used in the amplification according to the method of the invention. The blocker sequence component is generally designed to hybridize to the target sequence at a site which is upstream, i.e., located towards the 5' end of the target relative to the hybridization site of the single primer. Stated alternatively, and as described herein, the blocker sequence hybridizes to a segment of the target nucleic acid sequence which is 5' to the target sequence complementary to the 3' end of the primer extension product. The blocker sequence binds with sufficiently high affinity so as to terminate primer extension at the site where the blocker hybridizes to the target. This feature provides a strong stop for primer extension by the polymerase and defines the 3'-end of the primer extension product.

Suitable reaction medium and conditions are as described herein. In one embodiment, transcription is performed at a different temperature, generally lower, than that of the preceding steps. In another embodiment, all steps of the method are performed isothermally.

Figure 1C:
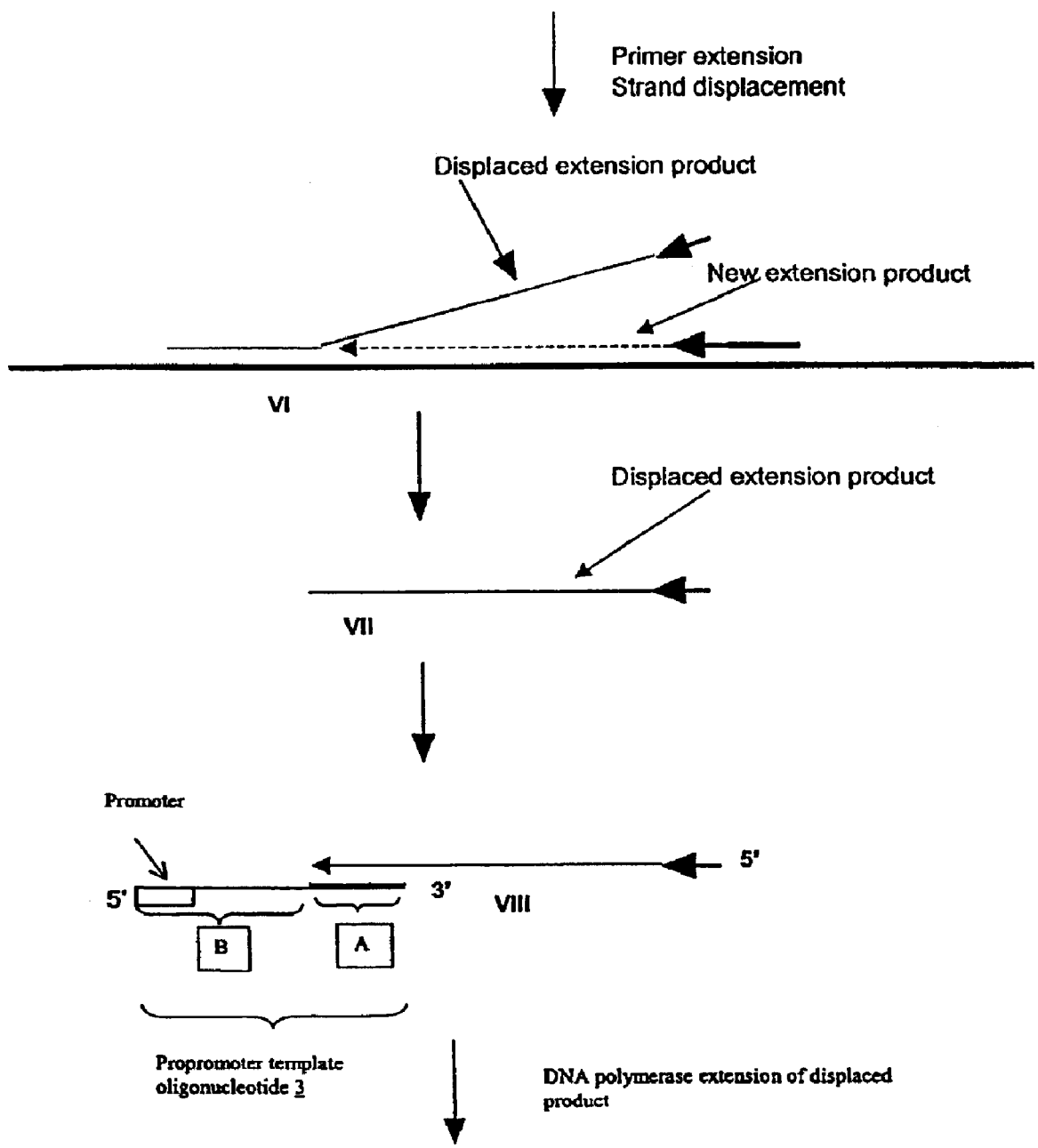

The single stranded nucleic acid target is combined with the composite primer, the blocker component, the propromoter template (PTO), DNA polymerase, ribonuclease such as RNaseH, a DNA dependent RNA polymerase, and nucleotides, such as NTPs (e.g., dNTPs and rNTPs). The composite primer and the blocker sequence component hybridize to the same target strand to form a tri molecular complex I (FIG. 1A). The primer is extended along the target up to the site of hybridization of the blocker sequence, to form complex II (FIG. 1A).

A ribonuclease, such as RNaseH, cleaves the RNA portion, generally the 5' RNA portion, of the single composite primer of complex II to form complex III (FIG. 1B). As described herein, the ribonuclease is specific for cleaving the RNA strand of an RNA/DNA hybrid, and does not digest single stranded RNA. Thus, the ribonuclease does not degrade the free composite primer. Free primer hybridizes to the primer complementary site of the target nucleic acid in complex III (FIG. 1B). This hybridization results in formation of complex IV (FIG. 1B), in which only the 5' RNA portion of the primer is hybridized to the target strand. Displacement of the 5' most portion of the primer extension product by the 3' DNA portion of the partially hybridized primer will result in formation of complex V (FIG. 1C), a substrate for a DNA polymerase. Extension of the primer along the target strand results in displacement of the first primer extension product (VI) from the complex. Cycles of the process of RNaseH cleavage, hybridization of a free composite primer and generation of strand displacement product proceeds to form multiple single stranded DNA products (VII). The displaced extension products are fully complementary to the target sequence and does not comprise a 3' end portion which is not complementary to the target.

Figure 1D:
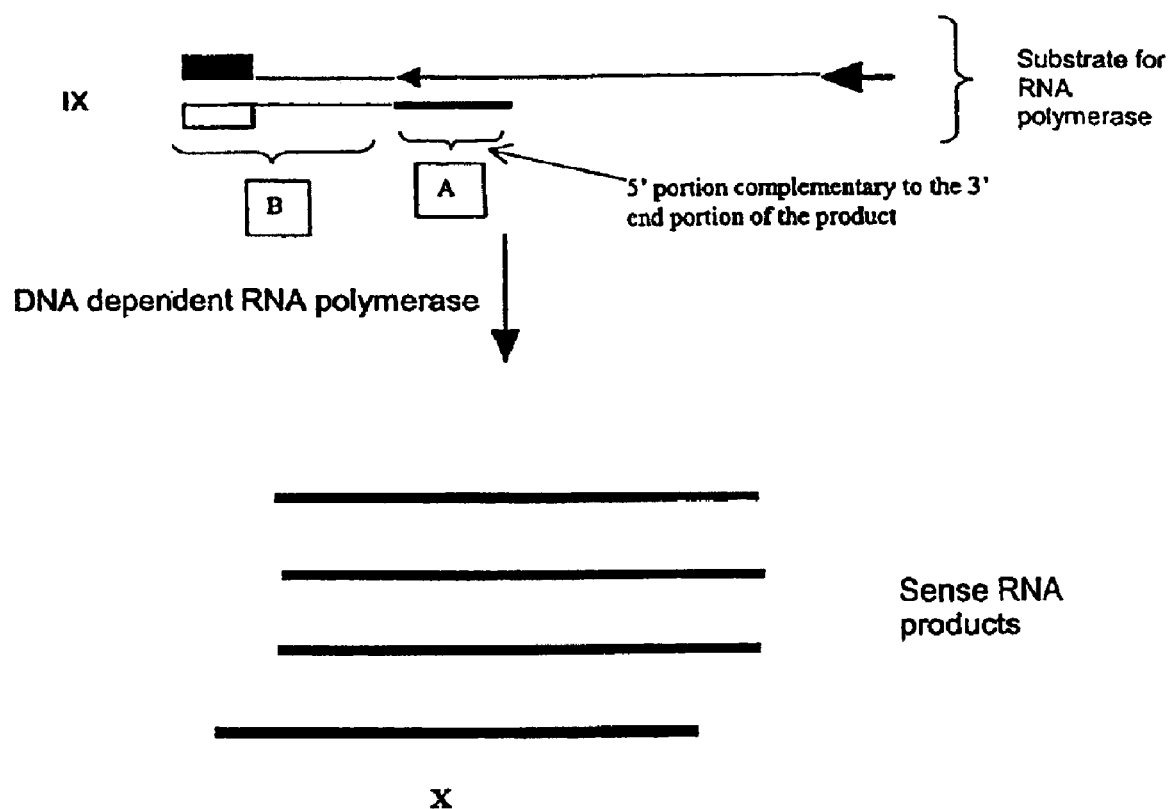

The promoter template oligonucleotide (PTO) binds to the displaced extension product to form complex VIII (FIG. 1C), by hybridization of the 3' end portion (A) of the propromoter template to the 3' end of the displaced primer extension product. As described herein, the 3' end of the PTO may or may not be blocked. When the 3' end of the propromoter template is not blocked, the template will be extended along the displaced primer extension product. The 3' end of the displaced extension product will be extended by the nucleotide (DNA) polymerase along the B portion of the hybridized propromoter template to form complex IX (see FIG. 1D), which comprises at one end a double stranded promoter sequence for the DNA-dependent RNA polymerase. Complex IX is depicted in FIG. 1D as the product of hybridization of a promoter template (PTO) in which the 3' end is blocked for extension by the polymerase. Alternatively, when the 3' end of the promoter template is not blocked, extension of the 3' end along the displaced primer extension product results in formation of a fully double stranded complex. The DNA-dependent RNA polymerase will transcribe both forms of the extended displaced primer extension product of complex IX. The choice of RNA polymerase takes into account its capability to transcribe either the partial duplex or the fully double stranded duplex forms of the complex. Multiple copies of a sense single stranded RNA (X) are produced by this transcription step. (FIG. 1D).

The production of preferably at least about 1, more preferably at least about 50, even more preferably at least about 75, still more preferably at least about 100, and most preferably at least about 1000, RNA transcript products from each primer extension product is expected.

Figure 1E:
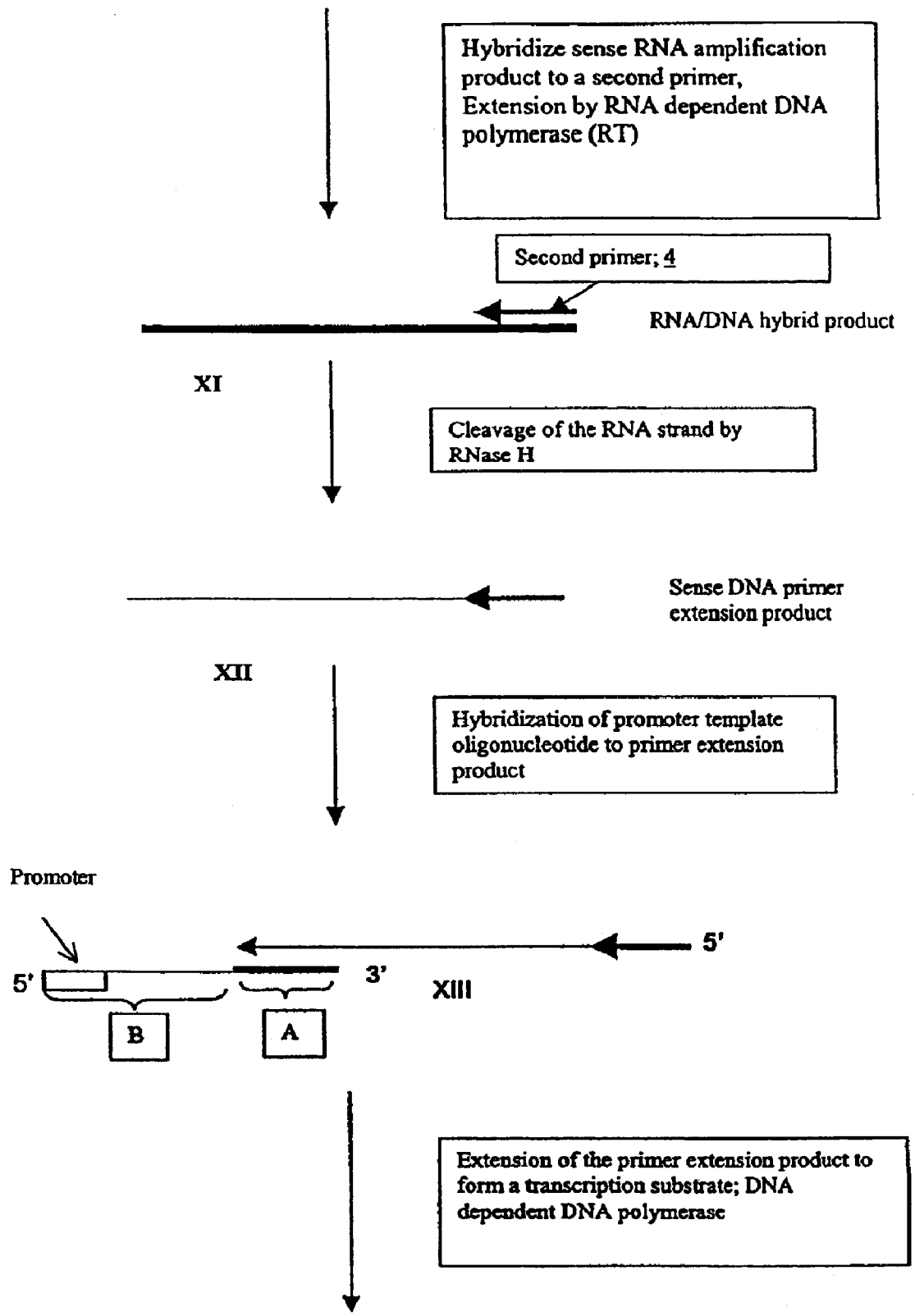

As illustrated in FIG. 1E, the second set of steps (second transcription module) utilize a second oligonucleotide primer, 4, which is the same sense as the composite primer relative to the target nucleic acid sequence, the promoter template oligonucleotide as used in the first module, an RNA-dependent DNA polymerase or reverse transcriptase (RT), a DNA-dependent DNA polymerase, RNaseH and a DNA-dependent RNA polymerase. The DNA polymerase, reverse transcriptase, and the RNaseH activities may be contained in the same enzyme, as is known in the art.

The two modules may be combined or carried out sequentially. For the purpose of simplicity, the processes are described herein as sequential steps. An aliquot of the reaction mix of the first set of steps is combined with a mixture containing the above mentioned components and the amplification reaction carried out isothermally.

The second primer, 4, hybridizes to a sequence at the 3' end of the RNA product of the first module. The second primer is thus generally designed to be complementary to a sequence which is upstream of the sequence which is complementary to the composite primer used in the first set of steps, e.g. a nested primer. The second primer is generally, although not necessarily, a DNA oligonucleotide (which is generally, but not necessarily, non-composite). The hybridized primer is extended by RT to form a RNA/DNA double stranded complex XI (FIG. 1E). The RNA strand of complex XI is cleaved by RNaseH to produce a single stranded DNA product XII (FIG. 1E), which is anti-sense relative to the target nucleic acid sequence (i.e., is complementary), similar to the primer extension product of the first set of steps.

Figure 1F:
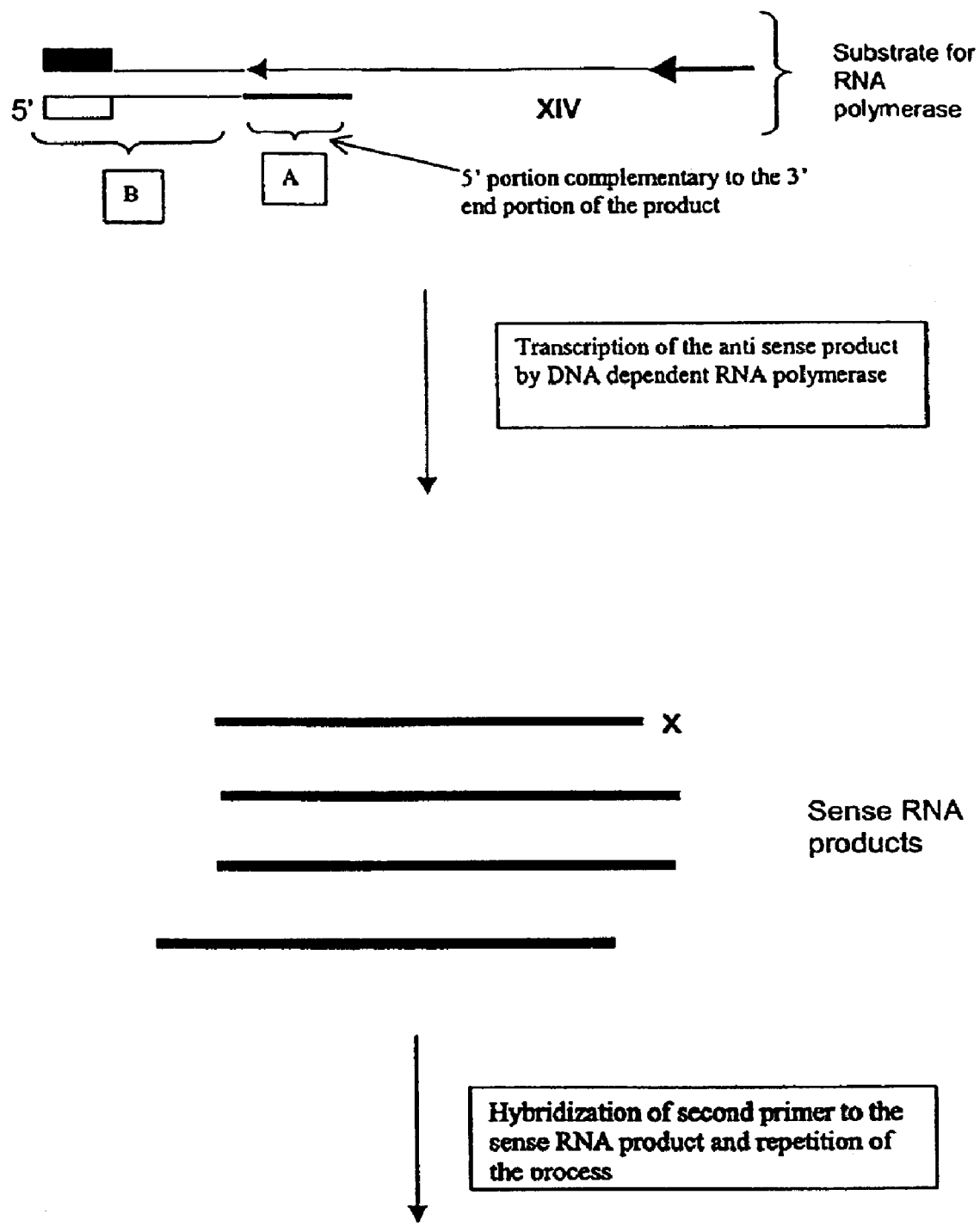

The 3'-end of primer extension product XII is generally complementary to the 3'-end of the promoter template oligonucleotide (as is the primer extension product of the first set of steps). Hybridization of product XII to the promoter template oligonucleotide results in formation of complex XIII (FIG. 1E). The 3'-end of the primer extension product is extended along the promoter template oligonucleotide by RT to form the partial duplex XIV (FIG. 1F) which has a double stranded promoter sequence at one end. Partial duplex XIV is a substrate for transcription by a DNA-dependent RNA polymerase, to form sense RNA products X (FIG. 1F).

Hybridization of primer 4 to product X will reinitiate the process described for the second transcription module, thus creating a cyclical amplification process, or exponential amplification. In the second set of steps, the extent of amplification of the initial sequence of interest will be limited by the concentration of the promoter template oligonucleotide and the second primer.

As evident from the above description, methods of the invention are suitable for highly efficient amplification of target nucleic acid as well as for applications of the amplification methods for purposes such as isothermal sequencing described herein.

Method 2: TSO-Based Enhanced Linear Nucleic Acid Amplification

In one embodiment, the TSO-based linear amplification method of the present invention is linked to transcription from the primer extension products to provide enhanced nucleic acid amplification. A schematic description of one embodiment of this novel amplification method, Method 2, is shown in FIGS. 2A-2E.

The TSO-based nucleic acid amplification method of the invention employs a composite primer, as described herein. A second oligonucleotide used in the amplification method of the invention is a template switch oligonucleotide (TSO), as described above. The nucleic acid target to be amplified can be DNA or RNA. Amplification of an RNA target will require an initial cDNA synthesis step according to methods known in the art. The TSO-based enhanced linear amplification method of the present invention produces multiple copies of an RNA product homologous (i.e., sense) to the target DNA sequence.

The single stranded target nucleic acid is combined with the composite primer, a TSO oligonucleotide, DNA polymerase, ribonuclease such as RNaseH, a DNA dependent RNA polymerase, and nucleotides, such as deoxyribonucleoside triphosphates (dNTPs) and ribonucleoside triphosphates (rNTPs) in a reaction medium suitable for nucleic acid hybridization and amplification, as is known in the art. In one embodiment, transcription is performed at a different temperature, generally lower, than that of the preceding steps. In another embodiment, all the steps of the methods are performed isothermally.

In one embodiment, the TSO functions as a termination sequence and provides a propromoter sequence. In another embodiment, the TSO does not comprise a propromoter sequence. In this embodiment, a propromoter sequence is provided separately by another oligonucleotide, such as a PTO, that comprises a propromoter sequence and is hybridizable to the 3' portion of the primer extension product such that transcription of the primer extension product can occur.

Figure 2A:
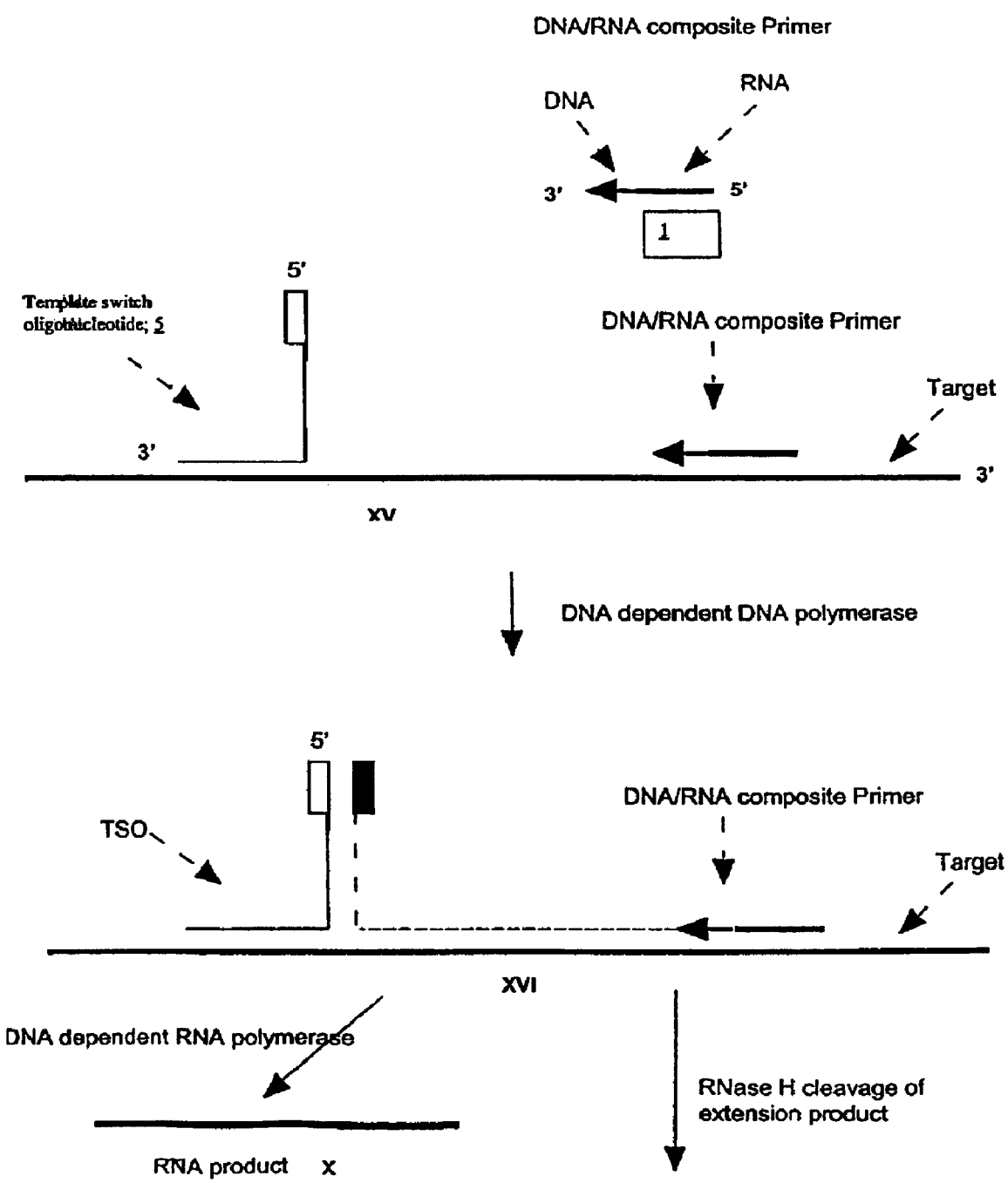

The single composite primer and the TSO then hybridize to the same strand of the nucleic acid to be amplified. The two oligonucleotides may be added to the sample suspected of containing the nucleic acid target prior to the target nucleic acid denaturation step. Hybridization of the two oligonucleotides to the target strand results in the formation of the tri molecular complex XV (FIG. 2A).

A DNA polymerase carries out primer extension. The primer is extended along the target nucleic acid strand of complex XV (FIG. 2A) and terminates at the site of TSO hybridization. Template switching from the target strand to the 5' unhybridized portion of the TSO, and further primer extension along the TSO template results in the formation of the tri molecular complex XVI which comprises a target nucleic acid, the TSO and the first primer extension product. The first primer extension product is a unique DNA comprising both a target dependent portion (i.e., sequence complementary to the target nucleic acid) and a TSO dependent portion (i.e., sequence complementary to the unhybridized portion of the TSO).

Complex XVI (FIG. 2A) is a substrate for both an RNA polymerase and a ribonuclease such as RNaseH. The DNA dependent RNA polymerase binds to the functional double stranded promoter of complex XVI and transcribes the first primer extension product to produce a sense RNA product X (FIG. 2A). A ribonuclease, such as RNaseH, which is specific for degradation of the RNA strand of an RNA/DNA heteroduplex, degrades the 5' portion of the primer extension product in complex XVI to form the tri molecular complex XVII (FIG. 2B).

Figure 2C:
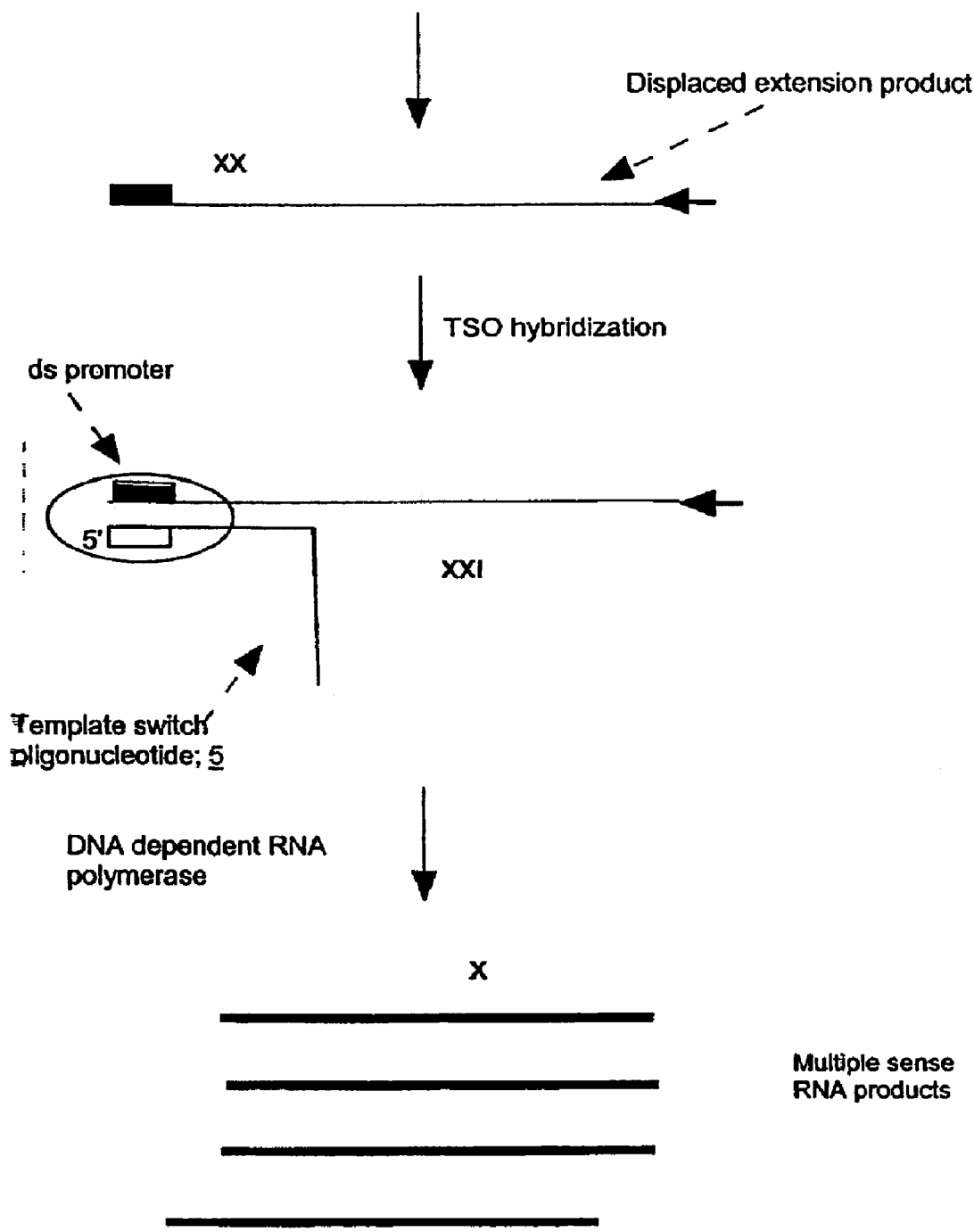

Free composite primer hybridizes to the primer complementary site of the target nucleic acid in complex XVII (FIG. 2B). This hybridization results in formation of complex XVIII (FIG. 2B) in which only the RNA portion, generally the 5' RNA portion, of the primer is hybridized to the target strand. Displacement of the 5' most portion of the primer extension product by the 3' DNA portion (XVIII) of the partially hybridized primer will result in formation of complex XIX (FIG. 2B), which is a substrate for a DNA polymerase. Extension of the primer along the target strand (XIX; FIG. 2B) results in displacement of the first primer extension product XX from the complex. Repeated primer extensions and strand displacements result in generation of multiple copies of polynucleotides (XX; FIG. 2C) that are substantially complementary to the target nucleic acid.

The primer extension product generated as described above is used as a template for transcription in the embodiment wherein TSO that comprises a propromoter sequence is provided. The displaced primer extension product (XX; FIG. 2C) hybridizes to free TSO oligonucleotide to form the partial duplex XXI (FIG. 2C). Complex (duplex) XXI comprises a double stranded portion at one end and two non-complementary single strands respectively derived from the primer extension product and the TSO. The double stranded portion of this partial duplex contains a fully functional double stranded promoter for the DNA dependent RNA polymerase. The latter recognizes the promoter of the partial duplex XXI and transcribes the primer extension product to form multiple copies of a sense RNA product X (FIG. 2C).

Figure 2D:
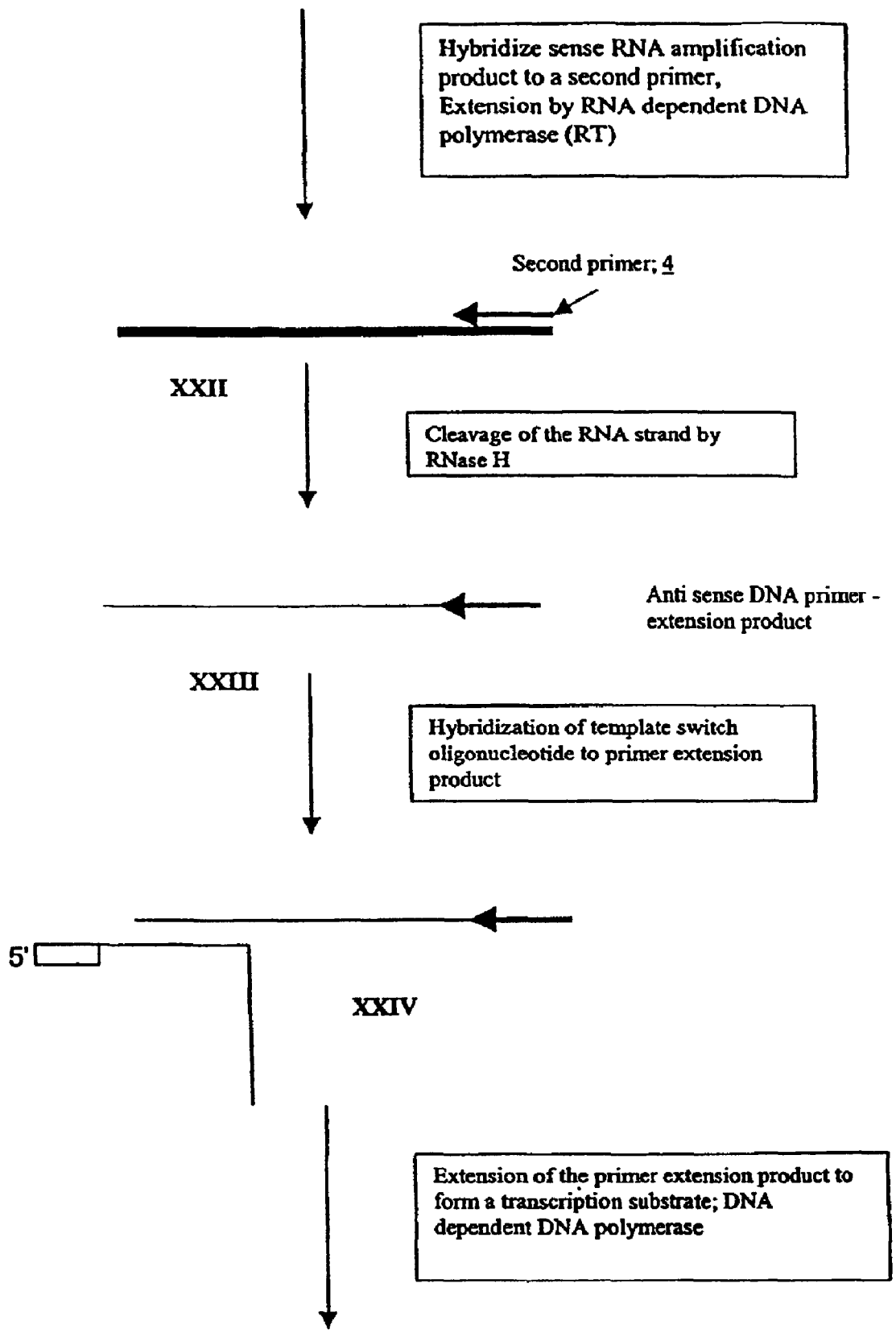
Figure 2E:
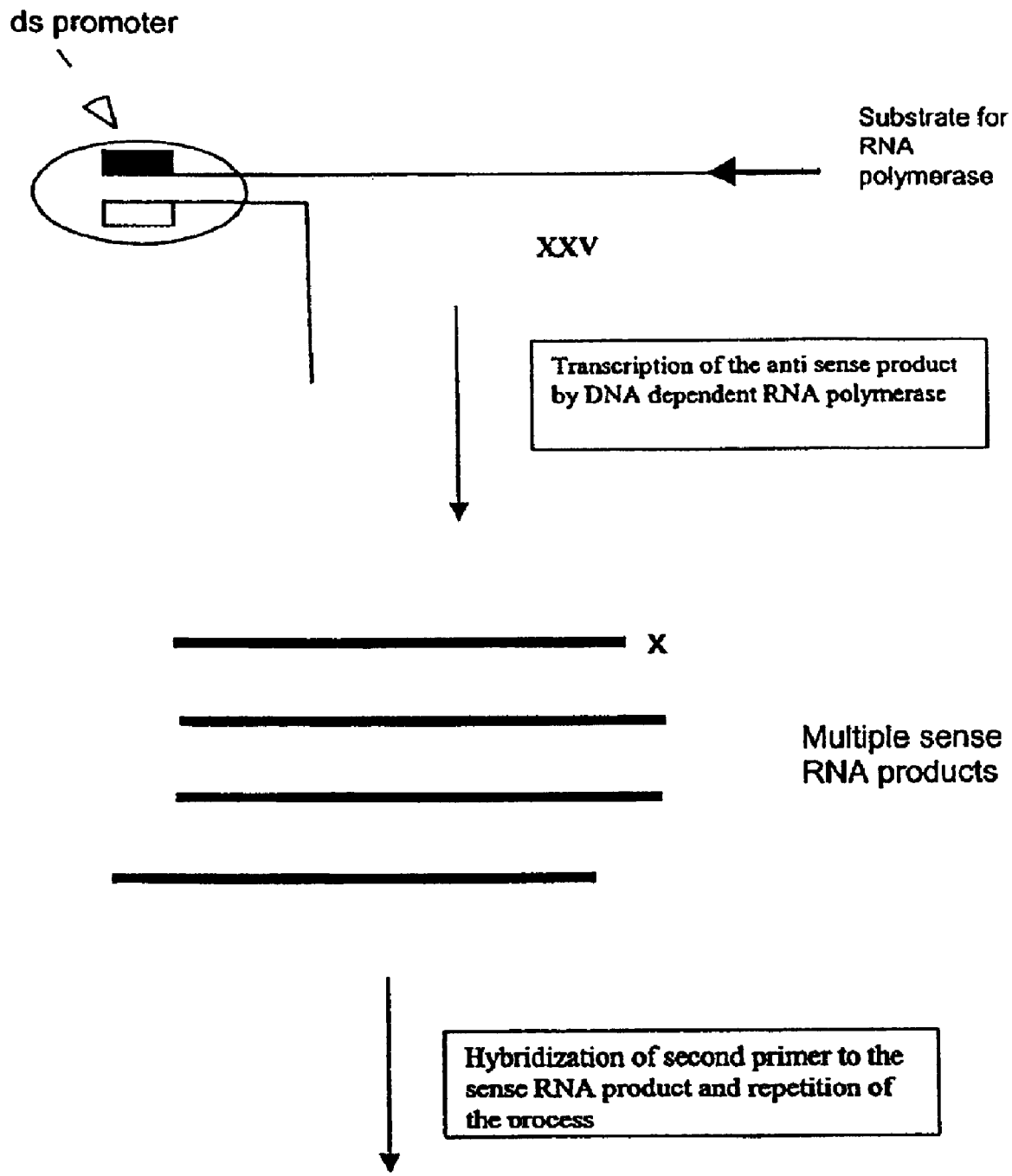

As described in method 1 and shown in FIGS. 2D-E, the isothermal amplification described above is linked to further amplification by the combination of the reaction mixture with a second primer, 4, RT, RNaseH, a DNA dependent RNA polymerase and the required nucleotide triphosphates. The second primer 4 hybridizes at the 5' portion of the sense RNA product, as in method 1, and is extended by RT to form an RNA/DNA hybrid duplex XXII (FIG. 2D). RNaseH cleaves the RNA strand of XXII to generate a single stranded anti sense DNA primer extension product XXIII (FIG. 2D). The 3'-end of the primer extension product is complementary to a sequence on the TSO. Hybridization of the primer extension product and free TSO results in formation of complex XXIV (FIG. 2D). DNA polymerase extends the 3' end of the primer extension product along the 5'-end of the TSO to form partial duplex XXV (FIG. 2E). The last is a substrate for DNA dependent RNA polymerase insofar as it comprises a double stranded promoter sequence at one end. Transcription of the primer extension product results in the generation of multiple copies of sense single stranded RNA product X (FIG. 2E).

Hybridization of the second primer 4 to the RNA product and extension by RT reinitiates the process as described above, thus enabling a cyclical amplification of the target nucleic acid sequence, as described for method 1.

Propromoter TSO-Based Amplification Methods

Propromoter TSO-based methods of the invention are based on the formation of a unique primer extension product using a template switch mechanism. The nucleic acid amplification methods of the invention encompass both primer extension by nucleotide polymerase and primer-independent transcription. The methods employ a single primer and a propromoter TSO capable of effecting template switching during primer extension. Both the primer and propromoter TSO are complementary to the same target nucleic acid strand. The propromoter TSO comprises a 3' portion which is complementary to the target polynucleotide; and a 5' portion which is not hybridizable to the target (under a given set of conditions), wherein the non-hybridizable 5' portion comprises a sequence (generally, a 5' most sequence) that is a single strand of a promoter for a DNA dependent RNA polymerase used in the amplification steps according to the methods of the invention. In some embodiments the sequence of the propromoter TSO which is immediately adjacent to the propromoter sequence (for example, 3' with respect to the propromoter sequence), is designed to maximize transcription by the RNA polymerase. Such sequences are known in the art and are described herein. TSO sequences capable of effecting template switch can be designed according to criteria known in the art (see Patel et. al., Proc. Natl. Acad. Sci. USA (1996), 93:2969-2974); U.S. Pat. Nos. 5,679,512; 5,683,879; & 6,030,774.

The propromoter TSO-based methods of amplification generally utilize several enzymes: a DNA-dependent DNA polymerase, a DNA-dependent RNA polymerase, an enzyme that cleaves RNA in an RNA/DNA hybrid (such as RNaseH), and an RNA-dependent DNA polymerase (such as reverse transcriptase). The enzymatic activities may be provided in individual enzymes or in various combinations (i.e., in one or more enzymes with multiple activities). The enzymes used for the amplification according to the methods of the invention are commercially available, as known to people skilled in the art.

The primer and the propromoter TSO are generally provided at high concentrations similar to those commonly used in PCR methods. The level of amplification of the target polynucleotide is generally limited by the concentration of these oligonucleotides. Whereas the primer is consumed by incorporation into the extension products, the propromoter TSO is not incorporated into the extension products. As illustrated in FIGS. 3A-B & 5A-B, the propromoter TSO participates in the initial template switch for the formation of a unique complex that is a substrate for DNA-dependent RNA polymerase (a transcription process). In certain embodiments, the propromoter TSO also participates, as illustrated in FIG. 3B, in binding to a single stranded DNA product (reverse transcribed from an RNA transcript from the first transcription module) for the formation of a second substrate for transcription. It is understood that any polynucleotide that comprises a propromoter sequence and a region capable of hybridizing to said single stranded DNA product can be used. For example, a PTO may be used.

Unlike other transcription-based isothermal amplification schemes, such as NASBA, TMA and the like, the propromoter TSO-based methods of the invention do not require the formation of a fully double stranded DNA product, which is an essential intermediate in these previously described transcription-based nucleic acid amplification methods. Since a double stranded intermediate DNA product is not required, forward and reverse primer pairs (for primer extensions along a target polynucleotide strand and its complement) are not used. This reduces the complexity of the primer extension reactions by eliminating the formation of primer-dimers where two or more primers hybridize and are extended to form double stranded substrates for transcription comprising double stranded promoters in a target-independent manner. The ability to use a single primer as described in the present invention reduces the complexity of the process. The process is further simplified by the ability to use a promoter template that does not have to be extended, for example, by using the same propromoter TSO in both the first primer extension step and in hybridization to a second primer extension product.

An Illustrative Embodiment of Propromoter TSO-Based Methods of the Invention

The amplification of target nucleic acid is generally based on a single stranded target, and so is typically preceded by rendering a target single stranded (if it is not already single stranded). Therefore, if the target nucleic acid is a double stranded DNA, the first step of the amplification is denaturation to yield a single stranded target. When the target nucleic acid is RNA, amplification can proceed directly from the single stranded target RNA, as shown below. Alternatively, the amplification may be preceded by synthesis of cDNA from the RNA target by methods known in the art.

Figure 3A:
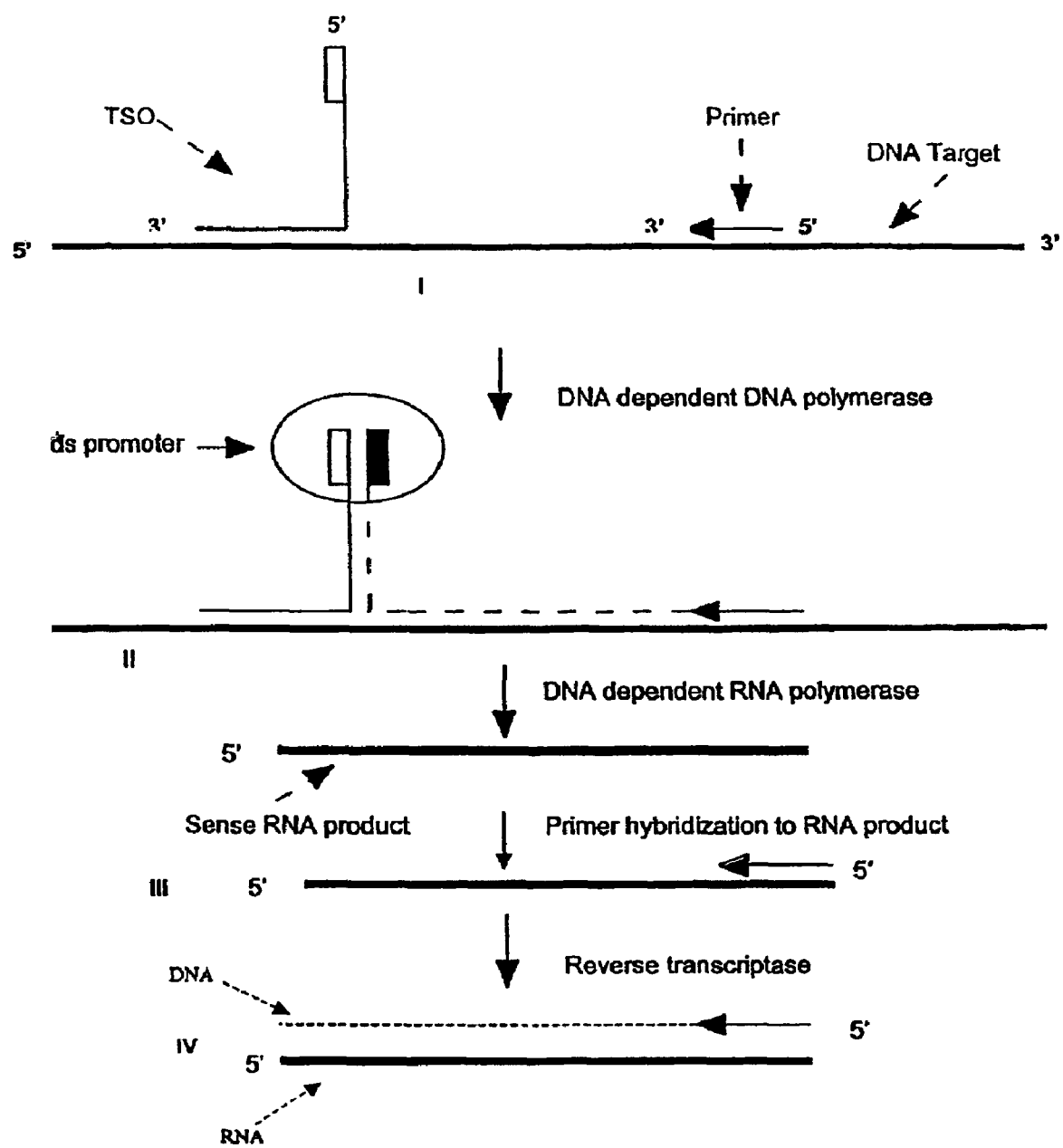
FIGS. 3A-B is a diagrammatic representation of the steps of a single primer isothermal amplification of a DNA target using template switching.
Figure 3B:
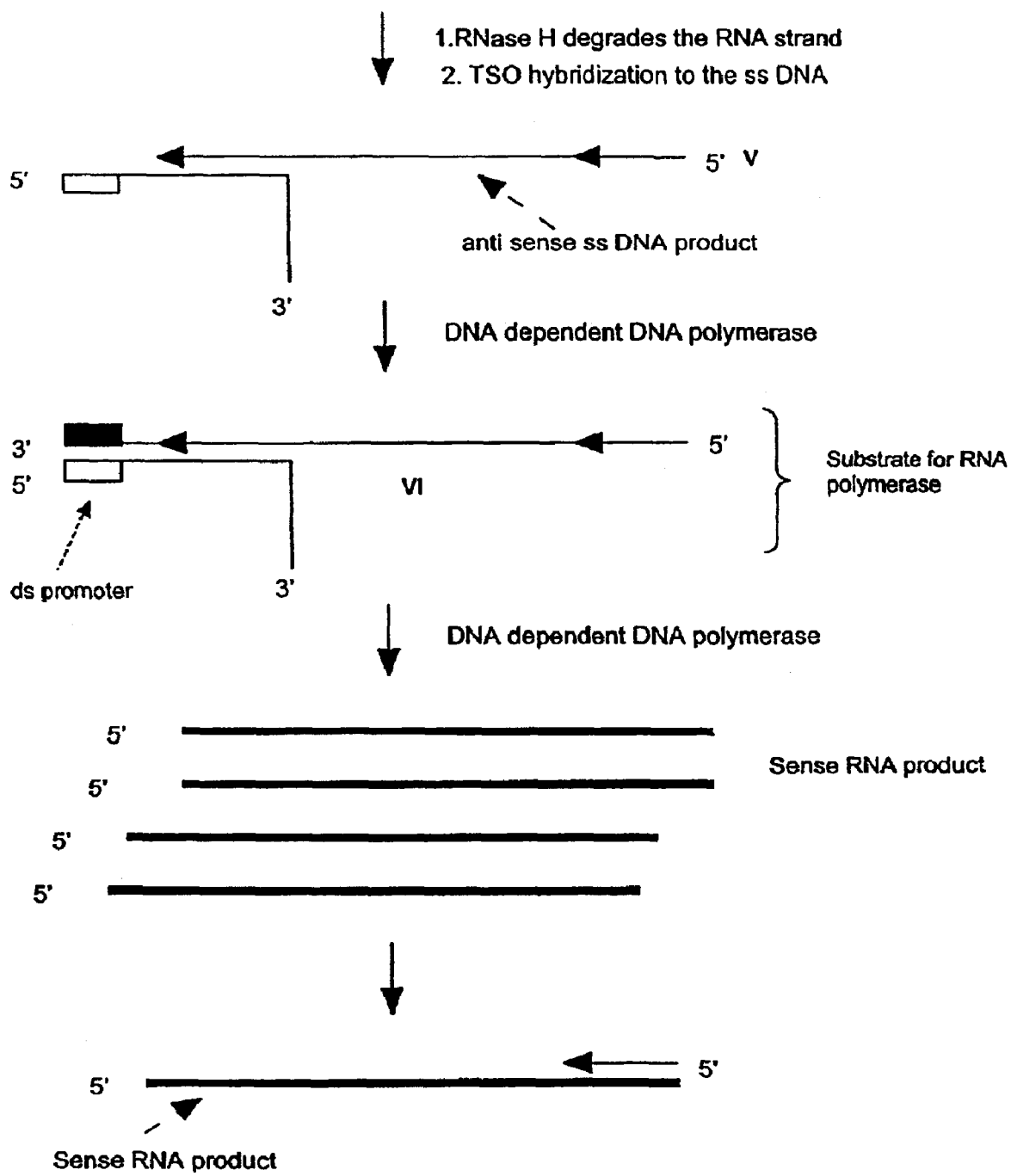

As illustrated in FIG. 3A-B, in one embodiment of the methods of the invention, a TSO and a single primer hybridize to a target nucleic acid strand to form the tri molecular complex I. The target strand of the complex may be DNA, as illustrated in FIG. 3A-B, or RNA, as illustrated in FIG. 4A-B.

A DNA polymerase carries out primer extension along the target strand of complex I. When the target is DNA, the enzyme is generally a DNA-dependent DNA polymerase, and when the target is RNA, the enzyme is generally an RNA-dependent DNA polymerase such as reverse transcriptase.

As illustrated in FIGS. 3A-B & 4A-B, primer extension is switched from the target to the 5' non-hybridized portion of the propromoter TSO at the point where the TSO is bound to the target thus effectively terminating replication of the target-specific sequence. Extension along the 5' non-hybridized portion of the TSO results in the formation of a unique extension product which is composed of a target-related portion and a TSO-related portion. The unique tri-molecular complex II (FIGS. 3A & 4A) of the target, TSO and the first primer extension product, comprises a double stranded promoter region, thus making it a substrate for a DNA-dependent RNA polymerase.

Figure 4A:
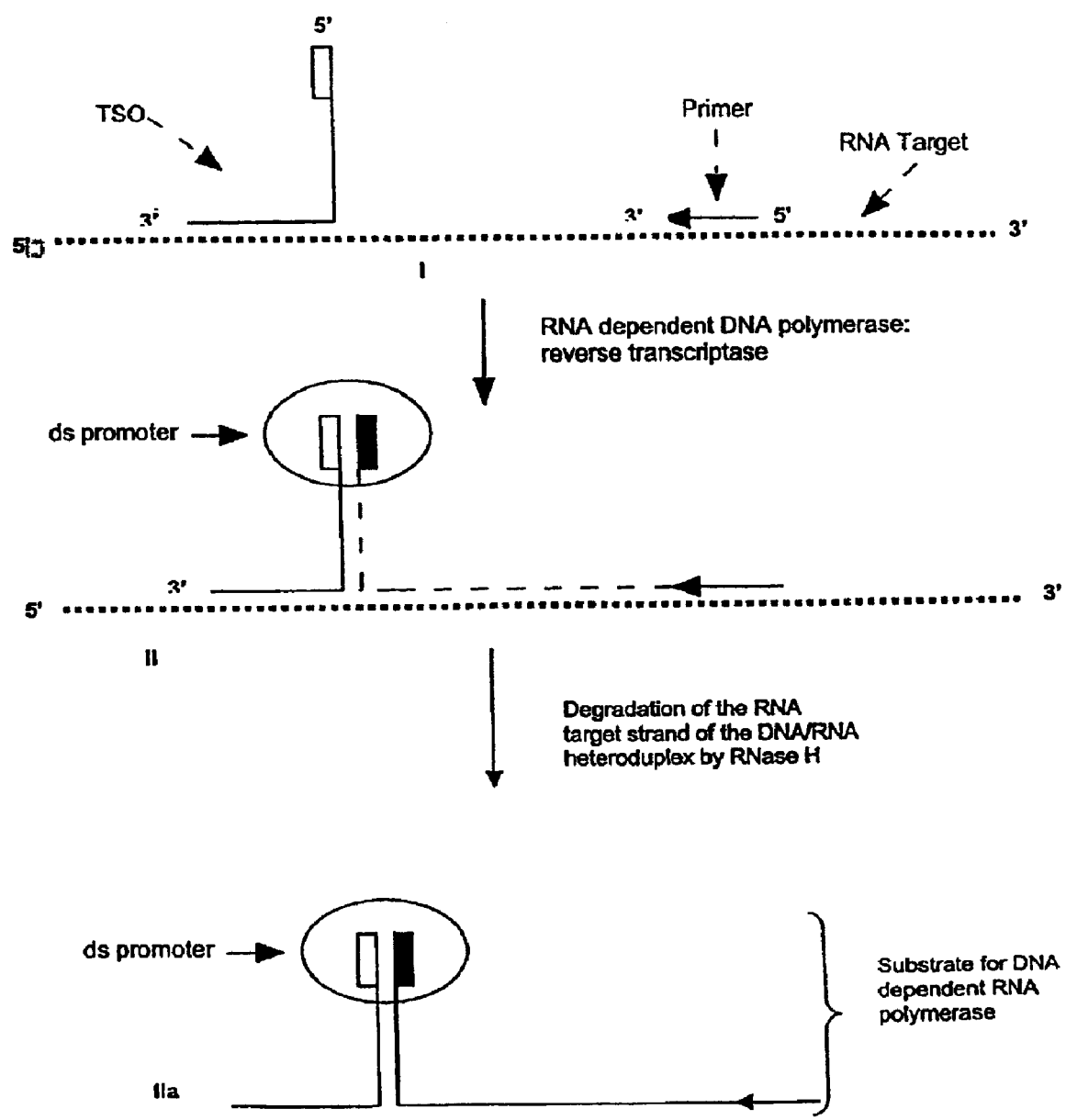
FIGS. 4A-B is a diagrammatic representation of the steps of a single primer isothermal amplification of an RNA target using template switching.
Figure 4B:
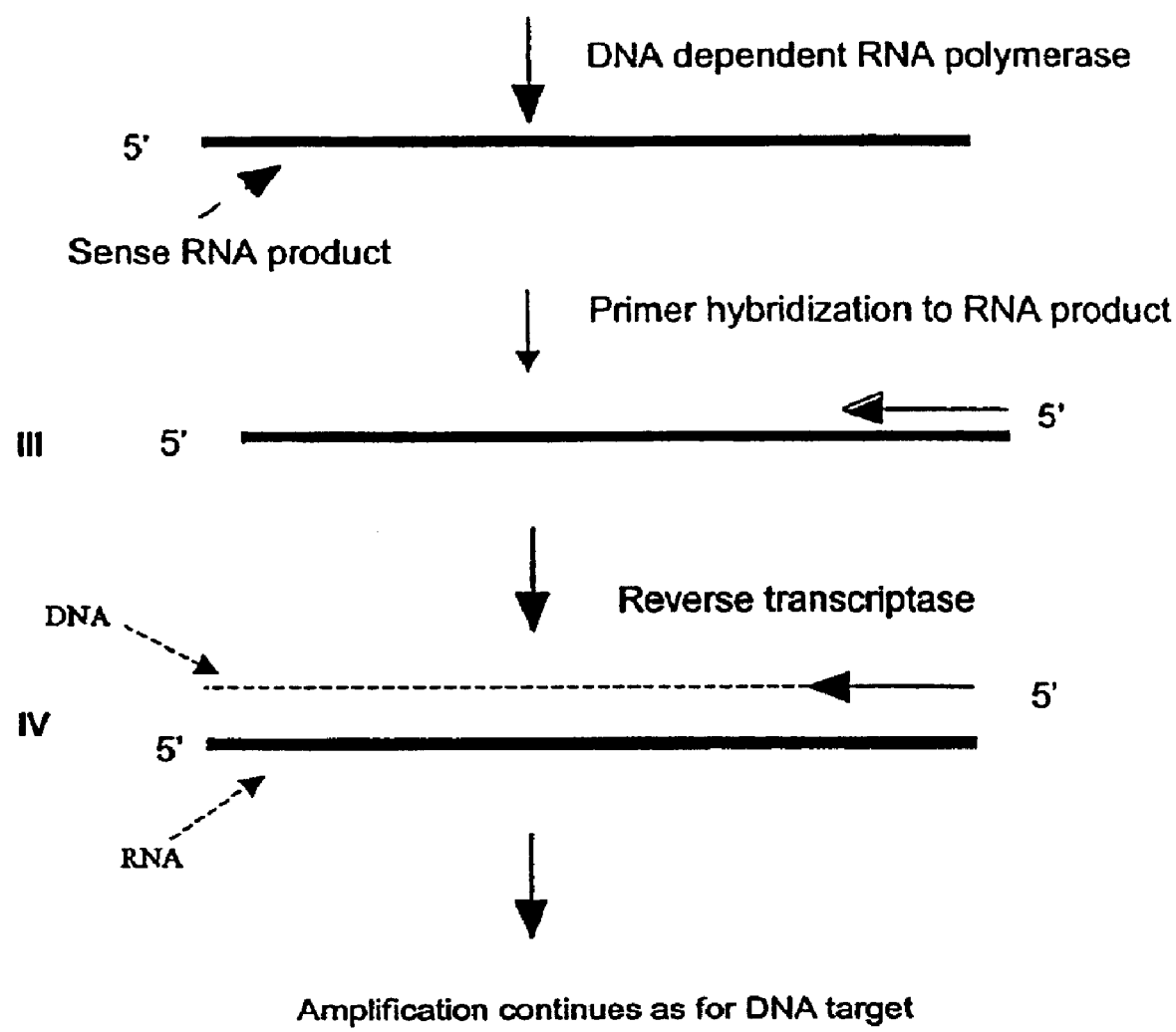

As illustrated in FIG. 4A-B, when the target is RNA, the RNA strand of complex II can be (but is not necessarily) degraded by RNaseH to form complex IIa, comprising the propromoter TSO and the first primer extension product. This complex further comprises a double stranded promoter and is a substrate for an RNA polymerase.

A DNA-dependent RNA polymerase binds to the double stranded promoter of complexes II (FIG. 3) and IIa (FIG. 4), and transcription of the unique primer extension product is initiated. This process results in the generation of multiple copies of a single stranded RNA product which are of the same sense as the target polynucleotide.

A second primer hybridizes to the sense RNA product to form complex III (FIGS. 3A & 4B). The second primer is generally and preferably the same as the first primer. In embodiments wherein the first and second primers are different, the second primer is generally of the same polarity as the first primer. Primer extension along the RNA product is carried out by an RNA-dependent DNA polymerase such as reverse transcriptase, yielding a DNA/RNA heteroduplex IV (FIGS. 3A & 4B).

RNaseH digestion of the RNA strand of complex IV results in the formation of a single stranded DNA product of primer extension by the RNA-dependent DNA polymerase (the second primer extension product). A free propromoter polynucleotide (shown in FIG. 3B as a propromoter TSO) hybridizes to the 3' portion of the single stranded DNA product to form complex V (FIG. 3B). If the propromoter polynucleotide is a TSO used in the first step, a sequence on the second primer extension product (DNA) which is complementary to a sequence on the TSO would have been incorporated into the second primer extension product by the template switch process.

The binding of a propromoter polynucleotide (illustrated in FIG. 3B as a TSO) to the DNA product results in a 5' overhang of the TSO, so the 3' end of the single stranded DNA product of complex V is extended along the propromoter polynucleotide (TSO) to replicate the promoter sequence. This results in the formation of complex VI (FIG. 3B) which contains a functional double stranded promoter sequence. Complex VI is a substrate for a DNA-dependent RNA polymerase. The polymerase binds to the double stranded promoter and transcribes the second primer extension product to produce multiple copies of the sense RNA product. The RNA products are substrates for further primer hybridization and extension as described above. Thus, cyclical amplification proceeds to form multiple copies of the sense RNA products.

Unless terminated deliberately, amplification can be expected to proceed until all free TSO is hybridized to the second primer extension product, or the primer is fully consumed.

As illustrated in FIGS. 3A-B, once formed following the transcription of the first primer extension products, the RNA product of amplification of either DNA or RNA target is the same, and the amplification schemes from that step on are the same.

Each transcription step (i.e., transcription of the first or second primer extension product) is expected to result in the production of preferably at least about 1, more preferably at least about 100, more preferably at least about 500, and most preferably at least about 1000, copies of a single stranded RNA product from a starting template (in the first transcription module, the template would be the target polynucleotide; in the second transcription module, the template would be an RNA transcript generated in the first transcription module).

The amplification products of the amplification method of the invention are single stranded and are thus readily detectable by any of a variety of methods known in the art. Both homogeneous and heterogeneous methods for detection of single stranded nucleic acids are known and would be suitable for the detection and quantification of the reaction products of the amplification method of the invention.

Components and Reaction Conditions Used in the Methods of the Invention

Template Nucleic Acid

The nucleic acid target to be amplified includes nucleic acids from any source in purified or unpurified form, which can be DNA (dsDNA and ssDNA) or RNA, including tRNA, mRNA, rRNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof. Obtaining and purifying nucleic acids use standard techniques in the art. In some embodiments, amplification of an RNA target will require initial cDNA synthesis, as known in the art. Amplification of a DNA-RNA hybrid would require denaturation of the hybrid to obtain a ssDNA or ssRNA, or denaturation followed by reverse transcription to obtain a cDNA. The target nucleic acid can be only a minor fraction of a complex mixture such as a biological sample and can be obtained from various biological material by procedures well known in the art.

The initial step of the amplification of a target polynucleotide is rendering the polynucleotide single stranded. If the target polynucleotide is double stranded, the initial step is target denaturation. The denaturation step may be thermal denaturation or any other method known in the art, such as alkali treatment.

Composite Primer

In one aspect, methods of the invention employ a composite primer that is composed of RNA and DNA portions. The composite design of the primer is designed such that subsequent displacement of the primer extension product by binding of a new (additional) composite primer and the extension of the new primer by the polymerase can be achieved. In addition, cleavage of the RNA portion of the primer extension product leads to generation of amplification product which is not a substrate for amplification by the composite primer, as described below.

Composite primers for use in the methods and compositions of the present invention comprise at least one RNA portion that is capable of (a) binding (hybridizing) to a sequence on the target nucleic acid (template) independent of hybridization of the DNA portion(s) to a sequence on the target nucleic acid; and (b) being cleaved with a ribonuclease when hybridized to the target DNA. The composite primers bind to the target nucleic acid to form a partial heteroduplex in which only the RNA portion of the primer is cleaved upon contact with a ribonuclease such as RNaseH, while the target strand remains intact, thus enabling annealing of another composite primer.

The composite primers also comprise a 3' DNA portion that is capable of hybridization to a sequence on the target nucleic acid (template) such that its hybridization to the target sequence (template) is favored over that of the nucleic acid strand that is displaced from the target nucleic acid by the DNA polymerase. Such primers can be rationally designed based on well known factors that influence nucleic acid binding affinity, such as sequence length and/or identity, as well as hybridization conditions. In a preferred embodiment, hybridization of the 3' DNA portion of the composite primer to its complementary sequence in the target nucleic acid is favored over the hybridization of the homologous sequence in the 5' end of the displaced strand to the target nucleic acid.

Generation of primers suitable for extension by polymerization is well known in the art, such as described in PCT Pub. No. WO99/42618 (and references cited therein). The composite primer comprises a combination of RNA and DNA (see definition above), with the 3'-end nucleotide being a nucleotide suitable for nucleic acid extension. The 3'-end nucleotide can be any nucleotide or analog that when present in a primer, is extendable by a DNA polymerase. Generally, the 3'-end nucleotide has a 3'-OH. Suitable primers include those that comprise at least one portion of RNA and at least one portion of DNA. For example, composite primers can comprise a 5'-RNA portion and a 3'-DNA portion (in which the RNA portion is adjacent to the 3'-DNA portion); or 5'- and 3'-DNA portions with an intervening RNA portion. Accordingly, in one embodiment, the composite primer comprises a 5' RNA portion and a 3'-DNA portion, preferably wherein the RNA portion is adjacent to the 3'-DNA portion. In another embodiment, the composite primer comprises 5'- and 3'-DNA portions with at least one intervening RNA portion (i.e., an RNA portion between the two DNA portions). In yet another embodiment, the composite primer of the invention comprises a 3'-DNA portion and at least one intervening RNA portion (i.e., an RNA portion between DNA portions).

The length of an RNA portion in a composite primer comprising a 3'-DNA portion and an RNA portion can be preferably from about 1 to about 50, more preferably from about 3 to about 20, even more preferably from about 4 to about 15, and most preferably from about 5 to about 10 nucleotides. In some embodiments of a composite primer comprising a 3'-DNA portion and an RNA portion, an RNA portion can be at least about any of 1, 3, 4, 5 nucleotides, with an upper limit of about any of 10, 15, 20, 25, 3, 50 nucleotides.

The length of the 5'-RNA portion in a composite primer comprising a 5'-RNA portion and a 3'-DNA portion can be preferably from about 3 to about 50 nucleotides, more preferably from about 5 to about 20 nucleotides, even more preferably from about 7 to about 18 nucleotides, preferably from about 8 to about 17 nucleotides, and most preferably from about 10 to about 15 nucleotides. In other embodiments of a composite primer comprising a 5'-RNA portion and a 3'-DNA portion, the 5'-RNA portion can be at least about any of 3, 5, 7, 8, 10 nucleotides, with an upper limit of about any of 15, 17, 18, 20, 50 nucleotides.

In embodiments of a composite primer comprising a 5'-RNA portion and a 3'-DNA portion further comprising non-5'-RNA portion(s), a non-5'-RNA portion can be preferably from about 1 to about 7 nucleotides, more preferably from about 2 to about 6 nucleotides, and most preferably from about 3 to about 5 nucleotides. In certain embodiments of a composite primer comprising a 5'-RNA portion and a 3'-DNA portion further comprising non-5'-RNA portion(s), a non-5'-RNA portion can be at least about any of 1, 2, 3, 5, with an upper limit of about any of 5, 6, 7, 10 nucleotides.

In embodiments of a composite primer comprising a 5'-RNA portion and a 3'-DNA portion, in which the 5'-RNA portion is adjacent to the 3'-DNA portion, the length of the 5'-RNA portion can be preferably from about 3 to about 50 nucleotides, more preferably from about 5 to about 20 nucleotides, even more preferably from about 7 to about 18 nucleotides, preferably from about 8 to about 17 nucleotides, and most preferably from about 10 to about 15 nucleotides. In certain embodiments of a composite primer comprising a 5'-RNA portion and a 3'-DNA portion, in which the 5'-RNA portion is adjacent to the 3'-DNA portion, the 5'-RNA portion can be at least about any of 3, 5, 7, 8, 10 nucleotides, with an upper limit of about any of 15, 17, 18, 20, 50 nucleotides.

The length of an intervening RNA portion in a composite primer comprising 5'- and 3'-DNA portions with at least one intervening RNA portion can be preferably from about 1 to about 7 nucleotides, more preferably from about 2 to about 6 nucleotides, and most preferably from about 3 to about 5 nucleotides. In some embodiments of a composite primer comprising 5'- and 3'-DNA portions with at least one intervening RNA portion, an intervening RNA portion can be at least about any of 1, 2, 3, 5 nucleotides, with an upper limit of about any of 5, 6, 7, 10 nucleotides. The length of an intervening RNA portion in a composite primer comprising a 3'-DNA portion and at least one intervening RNA portion can be preferably from about 1 to about 7 nucleotides, more preferably from about 2 to about 6 nucleotides, and most preferably from about 3 to about 5 nucleotides. In some embodiments of a composite primer comprising a 3'-DNA portion and at least one intervening RNA portion, an intervening RNA portion can be at least about any of 1, 2, 3, 5 nucleotides, with an upper limit of about any of 5, 6, 7, 10 nucleotides. In a composite primer comprising a 3'-DNA portion and at least one intervening RNA portion, further comprising a 5'-RNA portion, the 5'-RNA portion can be preferably from about 3 to about 25 nucleotides, more preferably from about 5 to about 20 nucleotides, even more preferably from about 7 to about 18 nucleotides, preferably from about 8 to about 17 nucleotides, and most preferably from about 10 to about 15 nucleotides. In some embodiments of a composite primer comprising a 3'-DNA portion and at least one intervening RNA portion, further comprising a 5'-RNA portion, the 5'-RNA portion can be at least about any of 3, 5, 7, 8, 10 nucleotides, with an upper limit of about any of 15, 17, 18, 20 nucleotides.

The length of the 3'-DNA portion in a composite primer comprising a 3'-DNA portion and an RNA portion can be preferably from about 1 to about 20, more preferably from about 3 to about 18, even more preferably from about 5 to about 15, and most preferably from about 7 to about 12 nucleotides. In some embodiments of a composite primer comprising a 3'-DNA portion and an RNA portion, the 3'-DNA portion can be at least about any of 1, 3, 5, 7, 10 nucleotides, with an upper limit of about any of 10, 12, 15, 18, 20, 22 nucleotides.

The length of the 3'-DNA portion in a composite primer comprising a 5'-RNA portion and a 3'-DNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising a 5'-RNA portion and a 3'-DNA portion, the 3DNA portion can be at least about any of 1, 3, 5, 7, 10 nucleotides, with an upper limit of about any of 10, 12, 15, 18, 20, 22 nucleotides.

In embodiments of a composite primer comprising a 5'-RNA portion and a 3'-DNA portion, further comprising non-3'-DNA portion(s), a non-3'-DNA portion can be preferably from about 1 to about 10 nucleotides, more preferably from about 2 to about 8 nucleotides, and most preferably from about 3 to about 6 nucleotides. In some embodiments of a composite primer comprising a 5'-RNA portion and a 3'-DNA portion, further comprising non-3'-DNA portion(s), a non-3'-DNA portion can be at least about any of 1, 2, 3, 5 nucleotides, with an upper limit of about any of 6, 8, 10, 12 nucleotides.

In embodiments of a composite primer comprising a 5'-RNA portion and a 3'-DNA portion in which the 5'-RNA portion is adjacent to the 3'-DNA portion, the length of the 3'-DNA portion can be preferably from about 1 to about 20 nucleotides, more preferably from about 3 to about 18 nucleotides, even more preferably from about 5 to about 15 nucleotides, and most preferably from about 7 to about 12 nucleotides. In certain embodiments of the primer comprising a 5'-RNA portion and a 3'-DNA portion in which the 5'-RNA portion is adjacent to the 3'-DNA portion, the 3'-DNA portion can be at least about any of 1, 3, 5, 7, 10 nucleotides, with an upper limit of about any of 10, 12, 15, 18, 20, 22 nucleotides.

The length of a non-3'-DNA portion in a composite primer comprising 5'- and 3'-DNA portions with at least one intervening RNA portion can be preferably from about 1 to about 10 nucleotides, more preferably from about 2 to about 8 nucleotides, and most preferably from about 3 to about 6 nucleotides. In some embodiments of a primer comprising 5'- and 3'-DNA portions with at least one intervening RNA portion, a non-3'-DNA portion can be at least about any of 1, 2, 3, 5 nucleotides, with an upper limit of about any of 6, 8, 10, 12 nucleotides.

The length of the 3'-DNA portion in a composite primer comprising 5'- and 3'-DNA portions with at least one intervening RNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising 5'- and 3'-DNA portions with at least one intervening RNA portion, the 3'-DNA portion can be at least about any of 1, 3, 5, 7, 10 nucleotides, with an upper limit of about any of 10, 12, 15, 18, 20, 22 nucleotides.

The length of a non-3'-DNA portion (i.e., any DNA portion other than the 3'-DNA portion) in a composite primer comprising a 3'-DNA portion and at least one intervening RNA portion can be preferably from about 1 to about 10 nucleotides, more preferably from about 2 to about 8 nucleotides, and most preferably from about 3 to about 6 nucleotides. In some embodiments of a composite primer comprising a 3'-DNA portion and at least one intervening RNA portion, a non-3'-DNA portion can be at least about any of 1, 3, 5, 7, 10 nucleotides, with an upper limit of about any of 6, 8, 10, 12 nucleotides. The length of the 3'-DNA portion in a composite primer comprising a 3'-DNA portion and at least one intervening RNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising a 3'-DNA portion and at least one intervening RNA portion, the 3'-DNA portion can be at least about any of 1, 3, 5, 7, 10 nucleotides, with an upper limit of about any of 10, 12, 15, 18, 20, 22 nucleotides. It is understood that the lengths for the various portions can be greater or less, as appropriate under the reaction conditions of the methods of this invention.

In some embodiments, the 5'-DNA portion of a composite primer includes the 5'-most nucleotide of the primer. In some embodiments, the 5'-RNA portion of a composite primer includes the 5' most nucleotide of the primer. In other embodiments, the 3'-DNA portion of a composite primer includes the 3' most nucleotide of the primer. In other embodiments, the 3'-DNA portion is adjacent to the 5'-RNA portion and includes the 3' most nucleotide of the primer (and the 5'-RNA portion includes the 5' most nucleotide of the primer).

The total length of the composite primer can be preferably from about 10 to about 50 nucleotides, more preferably from about 15 to about 30 nucleotides, and most preferably from about 20 to about 25 nucleotides. In some embodiments, the length can be at least about any of 10, 15, 20, 25 nucleotides, with an upper limit of about any of 25, 30, 50, 60 nucleotides. It is understood that the length can be greater or less, as appropriate under the reaction conditions of the methods of this invention.

To achieve hybridization to a target nucleic acid (which, as is well known and understood in the art, depends on other factors such as, for example, ionic strength and temperature), the portion of the primer that is hybridizable to the target polynucleotide is preferably of at least about 60%, more preferably at least about 75%, even more preferably at least about 90%, and most preferably at least about 95% complementarity to the target polynucleotide.

As described herein, one or more composite primers may be used in an amplification reaction.

Depending on the method of amplification, the first primer may or may not be a composite primer. The composite primer-based methods generally require the use of a first primer that is a composite primer. The propromoter TSO-based methods may or may not utilize a first primer that is a composite primer. In some embodiments, the first primer of propromoter TSO-based methods consists of DNA.

Second Primer

The second primer in the methods of the invention comprises a sequence (which may or may not be the whole of the primer) that is hybridizable (under a given set of conditions) to a sense RNA transcript generated in a first transcription module at a site on the transcript such that the second primer extension product would include the sequence of interest. In some embodiments, the hybridizable sequence of the second primer is designed based on a known sequence of the desired binding site on a sense RNA transcript. In other embodiments, the hybridizable sequence is based on random sequences. In some embodiments, the second primer is a random primer.

In preferred embodiments of propromoter TSO-based methods, the first and second primers are the same. In other embodiments of propromoter TSO-based methods, the first and second primers are different. In yet other embodiments of propromoter TSO-based methods, the first and second primers hybridize to different complementary sequences.

To achieve hybridization to a sense RNA transcript (which, as is well known and understood in the art, depends on other factors such as, for example, ionic strength and temperature), the sequence of the second primer that is hybridizable to the sense RNA transcript is preferably of at least about 60%, more preferably at least about 75%, even more preferably at least about 90%, and most preferably at least about 95% complementarity to the sense RNA transcript.

In one embodiment, the second primer comprises DNA. In another embodiment, the second primer consists of DNA. In another embodiment, the second primer comprises RNA. In still another embodiment, the second primer consists of RNA. In yet another embodiment, the second primer comprises DNA and RNA.

In some embodiments, the second primer is provided by self priming (for example, by a hairpin loop) at the 3' end of the sense RNA transcript. In these embodiments, a sequence at the 3' end of the sense RNA transcript hybridizes to another sequence in the transcript itself. Self priming of polynucleotides has been described in, for example, U.S. Pat. No. 6,132,997. In these embodiments, said sequence at the 3' of the sense RNA transcript is generally cleaved following its hybridization to the transcript and/or its extension along the transcript.

As described herein, one or more second primers may be used in an amplification reaction.

Template Switch Oligonucleotide (TSO)

One aspect of the invention employs a template switch oligonucleotide (TSO) to effect template switching during primer extension along a target polynucleotide. In some embodiments of composite primer-based methods of the invention, the TSO functions as a termination sequence. In certain embodiments, the TSO functions as a propromoter polynucleotide.

A TSO comprises a 3' portion that can hybridize to the target and a 5' portion which is designed for strand switch during polymerization. Design of a TSO that would effect strand switch is known in the art, such as was previously described by Patel et al., (Proc. Nat'l Acad. Sci. USA, 93:2969-2974 (1996)).

The 3' portion hybridizes to the template at a location 5' to the position or region in the target polynucleotide that is complementary to the 3' end of the primer extension product prior to switching template from the target polynucleotide to the unhybridized portion of the TSO ("termination site").

In one embodiment, strand switch is promoted by the presence of mutually complementary short sequences in the TSO segments immediately 5' and 3' to the junction between the hybridized and non-hybridized portions of the TSO. Without intending to be bound by theory, one explanation is that in the event that the primer extension product is extended into the portion of the target nucleic acid that is hybridized to the TSO (through displacement of the hybridized portion of the TSO), the 3' end of the primer extension product would comprise a short sequence that can bind to its complementary short sequence in the segment of the TSO immediately adjacent to the junction between the hybridized and non-hybridized portions of the TSO. This increases the efficiency of template switching by increasing the probability that the primer extension product would switch to the TSO tail portion as a template. The length of the short complementary sequences is preferably from about 3 to about 20 nucleotides, more preferably from about 5 to about 15 nucleotides, and most preferably from about 7 to about 10 nucleotides. In some embodiments, length is at least about any of 1, 3, 5, 7, 10 nucleotides, with an upper limit of about any of 10, 15, 20, 25 nucleotides. It is understood that the length can be greater or less, as appropriate under the reaction conditions of the methods of this invention.

In some embodiments, the 5' portion of the TSO (referred to herein as a "propromoter TSO") comprises a propromoter sequence that is designed for formation of a double stranded promoter of an RNA polymerase. This embodiment of the TSO can function both as a termination sequence and to provide a promoter template. In this embodiment, the propromoter sequence of the TSO serves as a template for incorporation of a propromoter sequence (generally complementary to the propromoter sequence of the template TSO) into the primer extension product. Subsequent hybridization of a TSO comprising a propromoter sequence that is hybridizable to the propromoter sequence of the primer extension product results in formation of a double stranded promoter capable of effecting transcription by a suitable RNA polymerase. Promoter sequences that allow transcription of a template DNA are known in the art, as are methods of obtaining and/or making them. Preferably, the promoter sequence is selected to provide optimal transcriptional activity of the particular RNA polymerase used. Criteria for such selection, i.e., a particular promoter sequence particularly favored by a particular RNA polymerase, are also known in the art. For example, the sequences of the promoters for transcription by T7 DNA dependent RNA polymerase and SP6 are known in the art. The promoter sequence can be from a prokaryotic or eukaryotic source.

In one embodiment, the promoter sequence is adjacent to a sequence that is designed to provide for enhanced, or more optimal, transcription by the RNA polymerase used. In some embodiments, the sequence is not related (i.e., it does not substantially hybridize) to the target nucleic acid. More optimal transcription occurs when transcriptional activity of the polymerase from a promoter that is operatively linked to said sequence is greater than from a promoter that is not so linked. The sequence requirements for optimal transcription are generally known in the art as previously described for various DNA dependent RNA polymerases, such as in U.S. Pat. Nos. 5,766,849 and 5,654,142.

In a preferred embodiment, a segment of the 3' portion of the TSO (including the entire 3' portion that hybridizes to target) that hybridizes to the template DNA is attached to the template DNA such that displacement of the TSO by the polymerase that effects primer extension is substantially, or at least sufficiently, inhibited. Suitable methods for achieving such attachment includes techniques known in the art, such as using a cytosine analog that contains a G-clamp heterocyclic modification (described in Flanagan et al., Proc. Natl. Acad. Sci. USA 1999, 96(7):3513-8); and locked nucleic acids (described, e.g., in Kumar et al., Bioorg. Med. Chem. Lett. 1998, 8(16):2219-22; and Wahlestedt et al., Proc. Natl. Acad. Sci. USA 2000, 97(10):5633-8). Other suitable methods include using, where appropriate, sequences with a high GC content and/or cross-linking. Any of these methods for obtaining enhanced attachment may be used alone or in combination. Displacement of the TSO is substantially or sufficiently inhibited if the polymerase switches template from the target nucleic acid strand to the unhybridized portion of the TSO in at least about 25%, preferably at least about 50%, more preferably at least about 75%, and most preferably at least about 90%, of the events of primer extension. Substantially or sufficiently inhibited TSO displacement can also be empirically indicated if the amplification methods lead to a satisfactory result in terms of amount of the desired product. Generally, under a given set of conditions, the "modified" TSO binds more tightly to template as compared to a TSO not so modified.

The length of the TSO portion that hybridizes to the target nucleic acid strand is preferably from about 15 to 50 nucleotides, more preferably from about 20 to 45 nucleotides, and most preferably from about 25 to 40 nucleotides. In other embodiments, the length is at least about any of the following: 10, 15, 20, 25, 30; and less than about any of the following: 35, 40, 45, 50, 55. It is understood that the length can be greater or less, as appropriate under the reaction conditions of the methods of this invention. The complementarity of the TSO portion that hybridizes to the target nucleic acid strand is preferably at least about 25%, more preferably at least about 50%, even more preferably at least about 75%, and most preferably at least about 90%, to its intended binding sequence on the target nucleic acid.

Polynucleotide Comprising a Termination Polynucleotide Sequence

In some embodiments of the methods of the present invention, a polynucleotide comprising a termination sequence is included, examples of which are provided below.

(i) TSO

As described above, a TSO can function as a polynucleotide comprising a termination sequence to affect primer extension along a target polynucleotide.

(ii) Blocker Sequence

In some embodiments, the primer extension termination sequence is provided by a blocker sequence. The blocker sequence is a polynucleotide, usually a synthetic polynucleotide, that is single stranded and comprises a sequence that is hybridizable, preferably complementary, to a segment of target nucleic acid sequence 5' of the position in the target sequence that is complementary to the 3' end of the primer extension product ("termination site"). The blocker comprises nucleotides that bind to the target nucleic acid with an affinity, preferably a high affinity, such that the blocker sequence resists displacement by DNA polymerase in the course of primer extension, in preferably more than about 30%, more preferably more than about 50%, even more preferably more than about 75%, and most preferably more than about 90%, of primer extension events. The length and composition of the blocker polynucleotide should be such that excessive random non-specific hybridization is avoided under the conditions of the methods of the present invention. The length of the blocker polynucleotide is preferably from about 3 to about 30 nucleotides, more preferably from about 5 to about 25 nucleotides, even more preferably from about 8 to about 20 nucleotides, and most preferably from about 10 to about 15 nucleotides. In other embodiments, the blocker polynucleotide is at least about any of the following: 3, 5, 8, 10, 15; and less than about any of the following: 20, 25, 30, 35. It is understood that the length can be greater or less as appropriate under the reaction conditions of the methods of this invention. The complementarity of the blocker polynucleotide is preferably at least about 25%, more preferably at least about 50%, even more preferably at least about 75%, and most preferably at least about 90%, to its intended binding sequence on the target nucleic acid.

In one embodiment, the blocker sequence comprises a segment that is attached to the target DNA such that displacement of the blocker sequence by the polymerase that effects primer extension is substantially, or at least sufficiently, inhibited. Suitable means for achieving such attachment and determining substantial, or sufficient, inhibition of displacement are as described above for TSO used in the methods of the present invention.

In one embodiment, the blocker polynucleotide cannot function efficiently as a primer for nucleic acid extension (i.e., extension from the blocker sequence is reduced, or inhibited). Techniques for blocking the primer function of the blocker polynucleotide include any that prevent addition of nucleotides to the 3' end of the primer by a DNA polymerase. Such techniques are known in the art, including, for example, substitution or modification of the 3' hydroxyl group, or incorporation of a modified nucleotide, such as a dideoxynucleotide, in the 3'-most position of the blocker polynucleotide that is not capable of anchoring addition of nucleotides by a DNA polymerase.

Polynucleotide Comprising a Propromoter and a Region Which Hybridizes to a Primer Extension Product Some embodiments employ a propromoter polynucleotide comprising a propromoter and a region which hybridizes to a primer extension product. In some embodiments, the propromoter polynucleotide is provided as a PTO, as described in greater detail below. In other embodiments, the propromoter polynucleotide is provided as a TSO (as described herein). In yet other embodiments, a propromoter polynucleotide comprises a portion (generally a 3' portion) that comprises a termination sequence (which does not substantially effect template switch), and a portion (generally a 5' portion) that comprises a propromoter sequence, wherein the portion that comprises a propromoter sequence is generally not hybridizable to a target polynucleotide (under conditions wherein the portion that comprises a termination sequence is hybridizable to a target polynucleotide). In some embodiments wherein a propromoter polynucleotide that comprises a portion comprising a termination sequence (which does not substantially effect template switch) and a portion comprising a propromoter sequence is provided, the propromoter polynucleotide may function both to effect termination of primer extension and to provide a propromoter sequence in the same amplification reaction.

Propromoter Template Oligonucleotide

In some embodiments, the methods employ a promoter sequence for transcription which is provided by a propromoter template oligonucleotide (PTO).

A PTO for use in the methods and compositions of the invention is a single-stranded polynucleotide, generally DNA, comprising a propromoter sequence that is designed for formation of a double stranded promoter of an RNA polymerase, and a portion capable of hybridizing to the 3' end of a primer extension product. In a preferred embodiment, the propromoter sequence is located in the 5' portion of the oligonucleotide and the hybridizing sequence is located in the 3' portion of the oligonucleotide. In one embodiment, and most typically, the promoter and hybridizing sequences are different sequences. In another embodiment, the promoter and hybridizing sequences overlap in sequence identity. In yet another embodiment, the promoter and hybridizing sequences are the same sequence, and thus are in the same location on the PTO. In the embodiments wherein hybridization of the PTO to the primer extension product results in a duplex comprising an overhang (the 5' end of the PTO that does not hybridize to the primer extension product, typically comprising all or part of the propromoter sequence), DNA polymerase fills in the overhang to create a double stranded promoter capable of effecting transcription by a suitable RNA polymerase.

Promoter sequences that allow transcription of a template polynucleotide are known in the art and have been discussed above. Preferably, the promoter sequence is selected to provide optimal transcriptional activity of the particular RNA polymerase used. Criteria for such selection, i.e., a particular promoter sequence particularly favored by a particular RNA polymerase, is also known in the art. For example, the sequences of the promoters for transcription by T7 DNA dependent RNA polymerase and SP6 are known in the art. The promoter sequence can be from a prokaryotic or eukaryotic source.

In some embodiments, the PTO comprises an intervening sequence between a propromoter sequence and a portion capable of hybridizing to the 3' end of the primer extension product. Suitable length of the intervening sequence can be empirically determined, and can be at least about 1, 2,4, 6, 8, 10, 12, 15 nucleotides. Suitable sequence identity of the intervening sequence can also be empirically determined, and the sequence is designed to preferably, but not necessarily, enhance degree of amplification as compared to omission of the sequence. In one embodiment, the intervening sequence is a sequence that is designed to provide for enhanced, or more optimal, transcription by the RNA polymerase used. Generally, the sequence is not related (i.e., it does not substantially hybridize) to the target nucleic acid. More optimal transcription occurs when transcriptional activity of the polymerase from a promoter that is operatively linked to said sequence is greater than from a promoter that is not so linked. The sequence requirements for optimal transcription are generally known in the art as previously described for various DNA dependent RNA polymerases, such as in U.S. Pat. Nos. 5,766, 849 and 5,654,142, and can also be empirically determined.

In another embodiment, the PTO comprises a sequence that is 5' to the propromoter sequence, i.e., the PTO comprises additional nucleotides (which may or may not be transcriptional regulatory sequences) located 5' to the propromoter sequence. Generally, but not necessarily, the sequence is not hybridizable (under a given set of conditions) to the primer extension product.

In one embodiment, the PTO cannot function efficiently as a primer for nucleic acid extension. Techniques for blocking the primer function of the PTO include any that prevent addition of nucleotides to the 3' end of the PTO by a DNA polymerase. Such techniques are known in the art, including, for example, substitution or modification of the 3' hydroxyl group, or incorporation of a modified nucleotide, such as a dideoxynucleotide, in the 3'-most position of the PTO that is not capable of anchoring addition of nucleotides by a DNA polymerase. It is possible to block the 3' end using a label, or a small molecule which is a member of a specific binding pair, such as biotin. It is also possible to render the 3' end non-extendable by addition of nucleotides which cannot hybridize to a primer extension product, either due to non-complementarity or due to structural modifications which do not support hydrogen bonding. In other embodiments, the PTO is not blocked.

The length of the portion of the PTO that hybridizes to a primer extension product of interest is preferably from about 5 to about 50 nucleotides, more preferably from about 10 to about 40 nucleotides, even more preferably from about 15 to about 35 nucleotides, and most preferably from about 20 to 30 nucleotides. In some embodiments, the hybridizing portion is at least about any of the following: 3, 5, 10, 15, 20; and less than about any of the following: 30, 40, 50, 60. The complementarity of the hybridizing portion is preferably at least about 25%, more preferably at least about 50%, even more preferably at least about 75%, and most preferably at least about 90%, to its intended binding sequence on the primer extension product of interest.

Combination Polynucleotide Comprising a Termination Sequence and a Propromoter Sequence In some embodiments of methods of the invention, a termination sequence and a propromtoer sequence are provided in a single combination polynucleotide. The combination polynucleotide comprises a portion (generally a 3' portion) that comprises a termination sequence that does not effect template switch under conditions wherein the termination sequence is hybridizable to a target polynucleotide, and a portion (generally a 5' portion) that comprises a propromoter sequence, wherein the portion that comprises a propromoter sequence is generally not hybridizable to the target polynucleotide (under conditions wherein the portion that comprises a termination sequence is hybridizable to the target polynucleotide). A termination sequence can be designed so as not to effect template switch using techniques known in the art, for example by ensuring that design characteristics that are known to promote template switch (such as described in Patel et al., Proc. Nat'l Acad. Sci. USA 1996, 93:2969-2974) are not present in the combination polynucleotide. The combination polynucleotide is hybridizable to the sequence of the template which is in the 5' direction with respect to the template sequence which is hybridizable to the primer. The polynucleotide further comprises a sequence which is hybridizable to a complementary sequence of the target polynucleotide. The sequence that is hybridizable to a complementary sequence of the target polynucleotide may be non-overlapping, overlapping or co-extensive with the termination sequence and/or propromoter sequence of the combination polynucleotide. Generally and preferably the sequence that is hybridizable to a complementary sequence of the target polynucleotide is hybridizable to a 3' portion of the complementary sequence of the target polynucleotide. Thus, in some embodiments of methods of the invention, a combination polynucleotide that comprises a portion comprising a termination sequence and a portion comprising a propromoter sequence functions both to effect termination of primer extension and to provide a propromoter sequence in the same amplification reaction.

DNA Polymerase, Ribonuclease and RNA Polymerase

The amplification methods of the invention employ some or all of the following enzymes: an RNA-dependent DNA polymerase, a DNA-dependent DNA polymerase, a ribonuclease such as RNaseH, and a DNA-dependent RNA polymerase. One or more of these activities may be found and used in a single enzyme. For example, RNaseH activity may be supplied by an RNA-dependent DNA polymerase (such as reverse transcriptase) or may be provided in a separate enzyme. Reverse transcriptases useful for this method may or may not have RNaseH activity.

One aspect of the invention is the formation of a single stranded cDNA from a primer-RNA complex. This process generally utilizes the enzymatic activities of an RNA-dependent DNA polymerase and a ribonuclease activity.

RNA-dependent DNA polymerases for use in the methods and compositions of the invention are capable of effecting extension of a primer according to the methods of the invention. Accordingly, a preferred RNA-dependent RNA polymerase is one that is capable of extending a nucleic acid primer along a nucleic acid template that is comprised at least predominantly of ribonucleotides. Suitable RNA-dependent DNA polymerases for use in the methods and compositions of the invention include reverse transcriptase. Many reverse transcriptases, such as those from avian myeloblastosis virus (AMV-RT), and Moloney murine leukemia virus (MMLV-RT) comprise more than one activity (for example, polymerase activity and ribonuclease activity) and can function in the formation of cDNA molecules. However, in some instances, it is preferable to employ a reverse transcriptase which lacks the RNaseH activity. Reverse transcriptase devoid of RNaseH activity are known in the art, including those comprising a mutation of the wild type reverse transcriptase where the mutation eliminates the RNaseH activity. In these cases, the addition of an RNaseH from other sources, such as that isolated from E. coli, can be employed for the formation of cDNA.

DNA-dependent DNA polymerases for use in the methods and compositions of the invention are capable of effecting extension of a primer according to the methods of the invention. Accordingly, a preferred polymerase is one that is capable of extending a nucleic acid primer along a nucleic acid template that is comprised at least predominantly of deoxynucleotides. Amplification of a polynucleotide according to certain methods of the invention involves the use of a DNA polymerase that is able to displace a nucleic acid strand from the polynucleotide to which the displaced strand is bound, and, generally, the more strand displacement capability the polymerase exhibits (i.e., compared to other polymerases which do not have as much strand displacement capability) is preferable. Preferably, the DNA polymerase has high affinity for binding at the 3'-end of an oligonucleotide hybridized to a nucleic acid strand. Preferably, the DNA polymerase does not possess substantial nicking activity. Generally, the polymerase preferably has little or no 5'→3' exonuclease activity so as to minimize degradation of primer, or primer extension polynucleotides. Generally, this exonuclease activity is dependent on factors such as pH, salt concentration, whether the template is double stranded or single stranded, and so forth, all of which are familiar to one skilled in the art. Mutant DNA polymerases in which the 5'→3' exonuclease activity has been deleted, are known in the art and are suitable for the amplification methods described herein. It is preferred that the DNA polymerase displaces primer extension products from the template nucleic acid in at least about 25%, more preferably at least about 50%, even more preferably at least about 75%, and most preferably at least about 90%, of the incidence of contact between the polymerase and the 5' end of the primer extension product. In some embodiments, the use of thermostable DNA polymerases with strand displacement activity is preferred. Such polymerases are known in the art, such as described in U.S. Pat. No. 5,744,312 (and references cited therein). Preferably, the DNA polymerase has little to no proofreading activity.

Suitable DNA polymerases for use in the methods and compositions of the invention include those disclosed in U.S. Pat. Nos. 5,648,211 and 5,744,312, which include exo-Vent (New England Biolabs), exo-Deep Vent (New England Biolabs), Bst (BioRad), exo-Pfu (Stratagene), Bca (Panvera), sequencing grade Taq (Promega), and thermostable DNA polymerases from *Thermoanaerobacter thermohydrosulfuricus*.

The ribonuclease for use in the methods and compositions of the invention is capable of cleaving ribonucleotides in an RNA/DNA hybrid. Preferably, the ribonuclease cleaves ribonucleotides regardless of the identity and type of nucleotides adjacent to the ribonucleotide to be cleaved. It is preferred that the ribonuclease cleaves independent of sequence identity. Examples of suitable ribonucleases for the methods and compositions of the invention are well known in the art, including ribonuclease H (RNaseH).

The DNA-dependent RNA polymerase for use in the methods and compositions of the invention are known in the art. Either eukaryotic or prokaryotic polymerases may be used. Examples include T7, T3 and SP6 RNA polymerases. Generally, the RNA polymerase selected is capable of transcribing from the promoter sequence provided by the propromoter polynucleotides as described herein. Generally, the RNA polymerase is a DNA-dependent polymerase, which is preferably capable of transcribing from a single stranded DNA template so long as the promoter region is double stranded.

In general, the enzymes used in the methods and compositions of the invention should not produce substantial degradation of the nucleic acid components of said methods and compositions.

Reaction Conditions and Detection

Appropriate reaction media and conditions for carrying out the methods of the invention are those that permit nucleic acid amplification according to the methods of the invention. Such media and conditions are known to persons of skill in the art, and are described in various publications, such as U.S. Pat. Nos. 5,554,516; 5,716,785; 5,130,238; 5,194,370; 6,090,591; 5,409,818; 5,554,517; 5,169,766; 5,480,784; 5,399,491; 5,679,512; and PCT Pub. No. WO99/42618. For example, a buffer may be Tris buffer, although other buffers can also be used as long as the buffer components are non-inhibitory to enzyme components of the methods of the invention. The pH is preferably from about 5 to about 11, more preferably from about 6 to about 10, even more preferably from about 7 to about 9, and most preferably from about 7.5 to about 8.5. The reaction medium can also include bivalent metal ions such as Mg2+ or Mn2+, at a final concentration of free ions that is within the range of from about 0.01 to about 15 mM, and most preferably from about 1 to 10 mM. The reaction medium can also include other salts, such as KCl or NaCl, that contribute to the total ionic strength of the medium. For example, the range of a salt such as KCl is preferably from about 0 to about 125 mM, more preferably from about 0 to about 100 mM, and most preferably from about 0 to about 75 mM. The reaction medium can further include additives that could affect performance of the amplification reactions, but that are not integral to the activity of the enzyme components of the methods. Such additives include proteins such as BSA, single strand binding proteins (for e.g., T4 gene 32 protein), and non-ionic detergents such as NP40 or Triton. Reagents, such as DTT, that are capable of maintaining enzyme activities can also be included. Such reagents are known in the art. Where appropriate, an RNase inhibitor (such as RNasin) that does not inhibit the activity of the RNase employed in the method can also be included. Any aspect of the methods of the invention can occur at the same or varying temperatures. Preferably, the amplification reactions (particularly, primer extension other than the first and second strand cDNA synthesis steps, and strand displacement) are performed isothermally, which avoids the cumbersome thermocycling process. The amplification reaction is carried out at a temperature that permits hybridization of the oligonucleotides (primer and/or propromoter polynucleotide) of the invention to the template polynucleotide and primer extension products, and that does not substantially inhibit the activity of the enzymes employed. The temperature can be in the range of preferably about 25° C. to about 85° C., more preferably about 30° C. to about 80° C., and most preferably about 37° C. to about 75° C. In some embodiments, the temperature for the transcription steps is lower than the temperature(s) for the preceding steps. In these embodiments, the temperature of the transcription steps can be in the range of preferably about 25° C. to about 85° C., more preferably about 30° C. to about 75° C., and most preferably about 37° C. to about 70° C.

Nucleotide and/or nucleotide analogs, such as deoxyribonucleoside triphosphates, that can be employed for synthesis of the primer extension products in the methods of the invention are provided in the amount of from preferably about 50 to about 2500 µM, more preferably about 100 to about 2000 µM, even more preferably about 200 to about 1700 µM, and most preferably about 250 to about 1500 µM. In some embodiments, a nucleotide or nucleotide analog whose presence in the primer extension strand enhances displacement of the strand (for example, by causing base pairing that is weaker than conventional AT, CG base pairing) is included. Such nucleotide or nucleotide analogs include deoxyinosine and other modified bases, all of which are known in the art. Nucleotides and/or analogs, such as ribonucleoside triphosphates, that can be employed for synthesis of the RNA transcripts in the methods of the invention are provided in the amount of from preferably about 0.25 to about 6 mM, more preferably about 0.5 to about 5 mM, even more preferably about 0.75 to about 4 mM, and most preferably about 1 to about 3 mM.

The oligonucleotide components of the amplification reactions of the invention are generally in excess of the number of target nucleic acid sequence to be amplified. They can be provided at about or at least about any of the following: 10, 102, 104, 106, 108, 1010, 1012 times the amount of target nucleic acid. Composite primers and propromoter polynucleotide can each be provided at about or at least about any of the following concentrations: 50 nM, 100 nM, 500 nM, 1000 nM, 2500 nM, 5000 nM.

In one embodiment, the foregoing components are added simultaneously at the initiation of the amplification process. In another embodiment, components are added in any order prior to or after appropriate timepoints during the amplification process, as required and/or permitted by the amplification reaction. Such timepoints, some of which are noted below, can be readily identified by a person of skill in the art. The enzymes used for nucleic acid amplification according to the methods of the invention can be added to the reaction mixture either prior to the target nucleic acid denaturation step, following the denaturation step, or following hybridization of the primer to the target polynucleotide, as determined by their thermal stability and/or other considerations known to the person of skill in the art. In these embodiments, the reaction conditions and components may be varied between the different reactions. Thus, for example, it is possible to mix a sample containing the target with a primer and the propromoter TSO in the propromoter TSO-based methods, prior to formation of a single stranded species from a double stranded DNA target. Depending on the heat stability of the amplification enzymes used, the enzymes required for the amplification according to the present invention can be added to the sample either prior to the initial step of formation of single stranded target, or at a later stage. In some embodiments, it may be desirable to include a nucleic acid modification enzyme (as described herein) early in the amplification process, which would generally require the use of thermostable nucleic acid modification enzymes, which are known in the art. These enzymes include, for example, thermostable DNA ligases (such as *Thermus thermophilus* (Tth) ligase; *Thermus* sp. AK16D ligase; *Aquifex aeolicus* ligase); thermostable DNA polymerases (such as Taq, Tth or Pfu DNA polymerase); and thermostable reverse transcriptase (such as rTth RNA-dependent DNA polymerase).

The amplification process can be stopped at various timepoints, and resumed at a later time. Said timepoints can be readily identified by a person of skill in the art. One timepoint is at the end of first primer extension. Another timepoint is at the end of second primer extension. Methods for stopping the reactions are known in the art, including, for example, cooling the reaction mixture to a temperature that inhibits enzyme activity or heating the reaction mixture to a temperature that destroys an enzyme. Methods for resuming the reactions are also known in the art, including, for example, raising the temperature of the reaction mixture to a temperature that permits enzyme activity or replenishing a destroyed (depleted) enzyme. In some embodiments, one or more of the components of the reactions is replenished prior to, at, or following the resumption of the reactions. Alternatively, the reaction can be allowed to proceed (i.e., from start to finish) without interruption.

The detection of the amplification product is indicative of the presence of the target sequence. Quantitative analysis is also feasible. Direct and indirect detection methods (including quantitation) are well known in the art. For example, by comparing the amount of product amplified from a test sample containing an unknown amount of a polynucleotide containing a target sequence to the product of amplification of a reference sample that has a known quantity of a polynucleotide that contains the target sequence, the amount of target sequence in the test sample can be determined. The amplification methods of the invention can also be extended to analysis of sequence alterations and sequencing of the target nucleic acid. Further, detection could be effected by, for example, examination of translation products from RNA amplification products.

Compositions and Kits of the Invention

The invention also provides compositions and kits used in the methods described herein. The compositions may be any component(s), reaction mixture and/or intermediate described herein, as well as any combination.

For example, the invention provides compositions comprising any two, preferably three, more preferably four, of the following: (a) a first primer which is a composite primer; (b) a second primer; (c) a DNA-dependent DNA polymerase; (d) an RNA-dependent DNA polymerase; (e) a propromoter polynucleotide; (f) an RNA polymerase; and (g) an enzyme that cleaves RNA from an RNA/DNA hybrid. In some embodiments, the composite primer, if included in the compositions, comprises an RNA portion and a 3' DNA portion (in some embodiments, the RNA portion is adjacent to the DNA portion). In other embodiments, the composite primer comprises 5'- and 3'-DNA portions with at least one intervening RNA portion. In other embodiments, the compositions further comprise a TSO (i.e., any of the TSO embodiments described herein, including TSOs containing one or more modifications which enhance binding to template). In some embodiments, the compositions further comprise a polynucleotide comprising a termination polynucleotide sequence.

In another embodiment, the invention provides compositions comprising any two, preferably three, more preferably four, of the following: (a) a propromoter TSO; (b) a first primer (which may consist of DNA); (c) a DNA-dependent DNA polymerase; (d) an RNA-dependent DNA polymerase; (e) an enzyme that cleaves RNA from an RNA/DNA hybrid; (f) optionally a second primer (which may consist of DNA); and (g) an RNA polymerase.

In some embodiments of the compositions described herein, the compositions further comprise single enzymes comprising multiple enzymatic activities. For example, the DNA-dependent DNA polymerase and the RNA-dependent DNA polymerase may be the same enzyme (such as reverse transcriptase); the DNA-dependent DNA polymerase and enzyme that cleaves RNA from an RNA/DNA hybrid may be the same enzyme; the RNA-dependent DNA polymerase and enzyme that cleaves RNA from an RNA/DNA hybrid may be the same enzyme; or all three activities of RNA-dependent DNA polymerase, DNA-dependent DNA polymerase and enzyme that cleaves RNA from an RNA/DNA hybrid may reside in a single enzyme.

Any of the above compositions may further comprise template (which comprises a target sequence) and/or any of the enzymes described herein (such as DNA polymerase, RNaseH, and/or RNA polymerase). The compositions are generally in aqueous form, preferably in a suitable buffer.

The invention also provides compositions comprising the amplification products described herein. Accordingly, the invention provides a population of sense RNA molecules which are copies of a target sequence, which are produced by any of the methods described herein.

The compositions are generally in a suitable medium, although they can be in lyophilized form. Suitable media include, but are not limited to, aqueous media (such as pure water or buffers).

The invention provides kits for carrying out the methods of the invention. Accordingly, a variety of kits are provided in suitable packaging. The kits may be used for any one or more of the uses described herein, and, accordingly, may contain instructions for any one or more of the following uses: amplifying a polynucleotide (RNA and/or DNA) sequence; sequencing of a nucleic acid sequence of interest; and detection of sequence mutation based on amplifying a nucleic acid sequence.

The kits of the invention comprise one or more containers comprising any combination of the components described herein, and the following are examples of such kits. For example, the invention provides kits comprising any two, preferably three, more preferably four, of the following: (a) a first primer which is a composite primer; (b) a second primer; (c) a DNA-dependent DNA polymerase; (d) an RNA-dependent DNA polymerase; (e) a propromoter polynucleotide; (f) an RNA polymerase; and (g) an enzyme that cleaves RNA from an RNA/DNA hybrid. In some embodiments, the composite primer, if included in the kits, comprises an RNA portion and a 3' DNA portion (in some embodiments, the RNA portion is adjacent to the DNA portion). In other embodiments, the composite primer comprises 5'- and 3'-DNA portions with at least one intervening RNA portion. In other embodiments, the kits further comprise a TSO (i.e., any of the TSO embodiments described herein, including TSOs containing one or more modifications which enhance binding to template). In some embodiments, the kits further comprise a polynucleotide comprising a termination polynucleotide sequence. In some embodiments, the kits further comprise instructions for using any of the components provided in the kits to amplify a target polynucleotide according to composite primer-based methods described herein.

In another embodiment, the invention provides kits comprising any two, preferably three, more preferably four, of the following: (a) a propromoter TSO; (b) a first primer (which may consist of DNA); (c) a DNA-dependent DNA polymerase; (d) an RNA-dependent DNA polymerase; (e) an enzyme that cleaves RNA from an RNA/DNA hybrid; (f) optionally a second primer (which may consist of DNA); and (g) an RNA polymerase. In some embodiments, the kits further comprise instructions for using any of the components provided in the kits to amplify a target polynucleotide according to any of the propromoter TSO-based methods described herein.

Kits may also optionally include deoxynucleoside triphosphates and/or ribonucleoside triphosphates. Kits may also include one or more suitable buffers (as described herein). Kits useful for nucleic acid sequencing may optionally include labeled or unlabelled nucleotide analogs that upon incorporation into a primer extension product effect termination of nucleotide polymerization. One or more reagents in the kit can be provided as a dry powder, usually lyophilized, including excipients, which on dissolution will provide for a reagent solution having the appropriate concentrations for performing any of the methods described herein. Each component can be packaged in separate containers or some components can be combined in one container where cross-reactivity and shelf life permit.

The kits of the invention may optionally include a set of instructions, generally written instructions relating to the use of components of the methods of the invention for the intended nucleic acid amplification, and/or, as appropriate, for using the amplification products for purposes such as nucleic acid sequencing and detection of sequence mutation. Electronic storage media (e.g., magnetic diskette or optical disk) containing instructions are acceptable modes of providing the instructions. Instructions may also be provided by storing said instructions in a central server, which is accessible via wide area networks (WAN) such as the internet.

The instructions included with the kit generally include information as to reagents (whether or not included in the kit) necessary for practicing the methods of the invention, instructions on how to use the kit, and/or appropriate reaction conditions. For example, the invention provides kits that comprise a first composite primer that comprises a sequence which is hybridizable to a target polynucleotide and instructions for using the primer to amplify a target polynucleotide according to composite primer-based methods described herein. In another example, kits can further comprise a second primer, and optionally instructions for using the primer to amplify a target polynucleotide according to composite primer-based methods described herein. In other examples, the kits can contain further components, such as any of (a) a propromoter polynucleotide (such as a PTO); and (b) any of the enzymes described herein, such as an enzyme which cleaves RNA from an RNA/DNA hybrid (for example, RNaseH), DNA polymerase (RNA-dependent or DNA-dependent) and RNA polymerase, and instructions for using the components to amplify a target polynucleotide according to composite primer-based methods described herein.

The component(s) of the kit may be provide in any convenient, appropriate packaging. The components may be packaged separately, or in one or multiple combinations. Where kits are provided for practicing amplification methods of the invention, the RNA polymerase (if included) is preferably provided separately from the components used in the steps prior to the transcription steps.

The relative amounts of the various components in the kits can be varied widely to provide for concentrations of the reagents that substantially optimize the reactions that need to occur to practice the methods disclosed herein and/or to further optimize the sensitivity of any assay. With respect to the compositions and kits of the invention, any component may comprise any of the embodiments of the components as described herein.

The invention also provides systems for effecting the methods described herein. These systems comprise various combinations of the components discussed above. A system may generally include one or more apparatuses for performing the amplification methods of the invention. Such apparatuses include, for example, heating devices (such as heating blocks or water baths) and apparatuses which effect automation of one or more steps of the methods described herein.

The invention also provides reaction mixtures (or compositions comprising reaction mixtures) which contain various combinations of components described herein. An example of a reaction mixture is (a) a complex of a first primer extension product and a target polynucleotide; (b) a polynucleotide comprising a propromoter sequence (for example, a PTO or a TSO); (c) RNA polymerase; and (d) a second primer. Other reaction mixtures are described herein and are encompassed by the invention.

The invention also includes compositions comprising any of the complexes (which are intermediates in the methods described herein) described herein. Examples of such complexes are schematically depicted in FIGS. 1-4.

Methods for Using the Amplification Methods and Compositions of the Invention

The methods and compositions of the invention can be used for a variety of purposes. For purposes of illustration, methods of sequencing, genotyping (nucleic acid mutation), microarray preparation, and characterizing nucleic acid sequences using the amplified nucleic acid products generated by the methods of the invention, are described.

Sequencing of Polynucleotides Using the Methods of the Invention

The amplification methods of the invention are useful, for example, for sequencing of a sequence of interest. The sequencing process is carried out as described for the amplification methods described herein.

Sequencing using the methods of the invention can be based on effecting premature (deliberate) termination of RNA transcription. The inclusion of rNTP analogs, which may be labeled or unlabelled, that upon incorporation into an RNA transcript effects termination of rNTP polymerization in the reaction mixture, will result in production of truncated RNA products, which result from blocking of the RNA polymerase at sites of incorporation of the analogs.

In one embodiment, the methods of sequencing comprise (a) amplifying a target polynucleotide containing the sequence of interest by the methods described herein in the presence of a mixture of rNTPs and rNTP analogs such that transcription is terminated upon incorporation of an rNTP analog; and (b) analyzing the amplification products to determine sequence.

In another embodiment, the methods of sequencing comprise (a) amplifying a target polynucleotide containing the sequence of interest by the methods described herein, wherein RNA transcripts are generated from the second primer extension product in the presence of a mixture of rNTPs and rNTP analogs such that transcription is terminated upon incorporation of a rNTP analog; and (b) analyzing the amplification products to determine sequence.

Suitable rNTP analogs include those commonly used in other sequencing methods and are well known in the art. Examples of rNTP analogs (such as RNA polymerase terminators) include 3'-dNTP. Sasaki et al., Biochemistry (1998) 95:3455-3460. These analogs may be labeled, for example, with fluorochromes or radioisotopes. The labels may also be labels which are suitable for mass spectroscopy. The label may also be a small molecule which is a member of a specific binding pair, and can be detected following binding of the other member of the specific binding pair, such as biotin and streptavidin, respectively, with the last member of the binding pair conjugated to an enzyme that catalyzes the generation of a detectable signal that could be detected by methods such as colorimetry, fluorometry or chemiluminescence. All of the above examples are well known in the art. These are incorporated into the RNA transcripts by the polymerase and serve to stop further extension along a template sequence. The resulting truncated polymerization products are labeled. The accumulated truncated products vary in length, according to the site of incorporation of each of the analogs, which represent the various sequence locations of a complementary nucleotide on the template sequence.

Analysis of the reaction products for elucidation of sequence information can be carried out using any of various methods known in the art. Such methods include gel electrophoresis and detection of the labeled bands using appropriate scanner, sequencing gel electrophoresis and detection of the radiolabeled band directly by phosphorescence such as Molecular Dynamics reader, capillary electrophoresis adapted with a detector specific for the labels used in the reaction, and the like. The label can also be a ligand for a binding protein which is used for detection of the label in combination with an enzyme conjugated to the binding protein, such as biotin-labeled chain terminator and streptavidin conjugated to an enzyme. The label is detected by the enzymatic activity of the enzyme, which generates a detectable signal. As with other sequencing methods known in the art, the sequencing reactions for the various nucleotide types (A, C, G, T or U) are carried out either in a single reaction vessel, or in separate reaction vessels (each representing 1 of the various nucleotide types). The choice of method to be used is dependent on practical considerations readily apparent to one skilled in the art, such as the nucleotide tri phosphate analogs and/or label used. Thus, for example, when each of the analogs is differentially labeled, the sequencing reaction can be carried out in a single vessel. The considerations for choice of reagent and reaction conditions for optimal performance of sequencing analysis according to the methods of the invention are similar to those for other previously described sequencing methods. The reagent and reaction conditions should be as described above for the nucleic acid amplification methods of the invention.

Detection of Mutation Based on Single Stranded Conformation Polymorphism Utilizing the Amplification Methods of the Invention The RNA amplification products generated according to the methods of the invention are also suitable for analysis for the detection of any alteration in the target nucleic acid sequence, as compared to a reference nucleic acid sequence which is identical to the target nucleic acid sequence other than the sequence alteration.

The RNA products of the amplification methods are suitable for single stranded conformation polymorphism (rSSCP) based mutation detection. The amplification methods of the invention can be directly linked to appropriate means for detecting single stranded conformation polymorphism, such as an electrophoretic separation method for the identification of specific mobility pattern of the single stranded RNA products for the elucidation of the presence of specific sequence feature(s), and/or the presence of any difference in a test nucleic acid as compared to a reference nucleic acid.

Methods based on gel electrophoresis or capillary electrophoresis can be used for the detection and analysis of the various single stranded conformational isomers. Alternatively, it is also likely that cleavage of the single stranded RNA product using nucleases which recognize sequence dependent secondary structures may be useful for the determination of sequence specific conformation polymorphism. Such secondary structure-specific nucleases are known in the art, such as the 5'-nucleases known as Cleavase™ enzymes (Third Wave). The electrophoretic methods are potentially more suitable for high throughput mutation, or genotyping, detection methods.

The determination of sequence specific electrophoretic pattern for a given nucleic acid sequence is useful for, for example, the detection of specific alleles of a test sequence. Furthermore, it is expected that an electrophoretic mobility pattern for the various alleles could be well differentiated, thus allowing the detection of two alleles in a nucleic acid sample from a single individual, as required for heterozygous genotype, or multiple alleles. Any alteration in the test nucleic acid sequence, such as base substitution, insertions or deletion, could be detected using this method. The method is expected to be useful for detection of specific single base polymorphism, SNP, and the discovery of new SNPs. Thus, the invention also provides methods for detecting a polynucleotide comprising a single nucleotide polymorphism, comprising: (a) amplifying a target polynucleotide using any of the methods described herein; and (b) analyzing the amplification products for single stranded conformation, wherein a difference in conformation as compared to a reference single stranded polynucleotide indicates a single nucleotide polymorphism in the target polynucleotide, whereby a polynucleotide comprising a single nucleotide polymorphism is detected.

Mutation Detection Utilizing the Composite Primer-Based Amplification Methods of the Invention The unique properties of the composite primer for use in the isothermal amplification methods of the invention provide the basis for an isothermal method for the detection of defined mutations, or polymorphic sites (such as SNPs), in a target nucleic acid sequence. The method is useful for genotyping, detection of mutation leading to drug resistance and the like. These methods are applicable to characterizing sequences in a region in the template strand which generally hybridize to the RNA portion of the composite primer—hence reference to "defined" mutations, which are defined in terms of their location.

In one embodiment, the RNA portion(s) of the composite primer is designed to be complementary to the sequence of the test target nucleic acid in which the presence of a sequence alteration is suspected. Stated alternatively, the primer comprises an RNA portion(s) that comprises a sequence that is complementary to the reference sequence (for example, a wild type sequence) against which the sequence in the test target nucleic acid is to be compared. In some embodiments, the altered sequence (i.e., the sequence comprising a sequence alteration) and the reference sequence are alleles. The sequence alteration may be a single nucleotide substitution, a deletion or insertion.

In another embodiment, the RNA portion(s) of the composite primer is designed to be complementary to the altered sequence suspected to be present in the test target nucleic acid. Stated alternatively, the primer comprises an RNA portion(s) that comprises a sequence that is complementary to the test target nucleic, and thus is not complementary to the reference sequence (for example, a wild type sequence) against which the sequence in the test target nucleic acid is to be compared. In some embodiments, the altered sequence (i.e., the sequence comprising a sequence alteration) and the reference sequence are alleles.

The RNA portion, generally 5' RNA portion, of the composite primer comprises a sequence which is complementary to a known normal wild type sequence, or a known mutant or a polymorphic genotype. Generally, a suitable composite primer comprises an RNA portion that allows the primer to preferentially hybridize to a target nucleic acid if the target nucleic sequence comprises a sequence complementary to the RNA portion of the primer compared to if there is a mismatch (i.e., the primer has the mutated sequence and the target does not, or vice versa), wherein the target nucleic acid has a bound primer extension product and has had its 5'-RNA portion cleaved. The presence of sequence alteration does not generally prevent the initial step of the amplification. The composite primer hybridizes to the target sequence, to form a tri molecular complex, and is extended. A ribonuclease, such as RNaseH, then cleaves the RNA portion of the extended primer of the complex. While it is likely that the presence of a mismatched base pair will affect the pattern of cleavage of the RNA/DNA hybrid, the cleavage is nonetheless likely to take place. The next step of binding of a composite primer to the complex by hybridization of the 5' RNA portion will be inhibited, preferably prevented, by a mismatch. This effect is dependent on factors such as the size of the hybridizing oligonucleotide and the stringency of the reaction condition. These factors are considered in the design of the composite primer, according to techniques well known and routine in the art. It is also possible that the mismatch will inhibit cleavage of the RNA portion(s) of the composite primer, thus preventing the amplification of the target sequence. Another possibility is that the mismatch will result in lower efficiency of cleavage of the RNA portion of the primer thus resulting in lower efficiency of amplification or production of less amplification product. The inability of the composite primer to hybridize to the target at this step of the amplification prevents further steps of primer extension strand displacement and production of multiple copies of the amplification products. It is understood that the detection of mutation by the methods of the present invention can be based on absence or presence of an amplification product, or quantitative comparisons of amount of accumulated amplification products. For example, when the composite primer comprises the reference sequence (for example, wild type), the presence of a mutation in a target strand may lead to no detectable amplification products; alternatively, it may lead to detectable products, but less than those produced from a template strand without the mutation.

When the composite primer comprises an RNA portion, generally a 5' RNA portion, that is fully complementary to a mutant genotype, amplification of a sequence which is of the normal genotype will be prevented, while a mutant genotype target will be amplified. Thus, in this case the detection and/or quantitative determination of multiple copies of the amplification product will be indicative of the presence of a target sequence of the mutant genotype. For example, parallel reactions that include either the nucleic acid sample of interest or reference sample of target nucleic with a wild type sequence could be run. Accumulation of more amplification products in the former compared to the latter reaction would be indicative of the presence of a mutant genotype in the sample of interest. Alternatively, when the composite primer comprises a 5' RNA sequence that is fully complementary to a normal genotype sequence of the test target, amplification of a target sequence of the mutant genotype is prevented, and the detection and/or quantitative determination of amplification products is indicative of a normal genotype.

Any of the composite primer-based amplification methods of the present invention are suitable for detection of mutation as described above.

Method of Preparing Microarrays of Nucleic Acids

The single stranded nature of the products of the amplification methods of the invention are particularly suitable for preparing microarrays comprising the amplification products.

Amplification products can be attached to a solid or semi-solid support or surface, which may be made, e.g., from glass, plastic (e.g., polypropylene, nylon), polyacrylamide, nitrocellulose, or other materials.

Several techniques are well-known in the art for attaching nucleic acids to a solid substrate such as a glass slide. One method is to incorporate modified bases or analogs that contain a moiety that is capable of attachment to a solid substrate, such as an amine group, a derivative of an amine group or another group with a positive charge, into the amplified nucleic acids. The amplified product is then contacted with a solid substrate, such as a glass slide, which is coated with an aldehyde or another reactive group which will form a covalent link with the reactive group that is on the amplified product and become covalently attached to the glass slide. Microarrays comprising the amplified products can be fabricated using a Biodot (BioDot, Inc. Irvine, Calif.) spotting apparatus and aldehyde-coated glass slides (CEL Associates, Houston, Tex.). Amplification products can be spotted onto the aldehyde-coated slides, and processed according to published procedures (Schena et al., Proc. Natl. Acad. Sci. U.S.A. (1996), 93: 10614-10619). Arrays can also be printed by robotics onto glass, nylon (Ramsay, G., Nature Biotechnol. (1998), 16:40-44), polypropylene (Matson, et al., Anal Biochem. (1995), 224(1):110-6), and silicone slides (Marshall, A. and Hodgson, J., Nature Biotechnol. (1998), 16:27-31). Other approaches to array assembly include fine micropipetting within electric fields (Marshall and Hodgson, supra), and spotting the polynucleotides directly onto positively coated plates. Methods such as those using amino propyl silicon surface chemistry are also known in the art, as disclosed at http://www.cmt.corning.com and http://cmgm.stanford.edu/pbrown/.

One method for making microarrays is by making high-density polynucleotide arrays. Techniques are known for rapid deposition of polynucleotides (Blanchard et al., Biosensors & Bioelectronics, 11:687-690). Other methods for making microarrays, e.g., by masking (Maskos and Southern, Nuc. Acids. Res. (1992),20:1679-1684), may also be used. In principle, and as noted above, any type of array, for example, dot blots on a nylon hybridization membrane, could be used. However, as will be recognized by those skilled in the art, very small arrays will frequently be preferred because hybridization volumes will be smaller.

The amplified polynucleotides may be spotted as a matrix on substrates comprising paper, glass, plastic, polypropylene, nylon, polyacrylamide, nitrocellulose, silicon, optical fiber or any other suitable solid or semi-solid (e.g., thin layer of polyacrylamide gel ((Khrapko, et al., DNA Sequence (1991), 1:375-388)) surface.

An array may be assembled as a two-dimensional matrix on a planar substrate or may have a three-dimensional configuration comprising pins, rods, fibers, tapes, threads, beads, particles, microtiter wells, capillaries, cylinders and any other arrangement suitable for hybridization and detection of target molecules. In one embodiment the substrate to which the amplification products are attached is magnetic beads or particles. In another embodiment, the solid substrate comprises an optical fiber. In yet another embodiment, the amplification products are dispersed in fluid phase within a capillary which, in turn, is immobilized with respect to a solid phase.

Characterization of Nucleic Acids

The amplification products obtained by the methods of the invention are particularly amenable to further characterization, in part because the products are single stranded. The amplified products can be analyzed using, for example, probe hybridization techniques known in the art, such as Northern blotting, and hybridizing to probe arrays. They can also be analyzed by electrophoresis-based methods, such as differential display and size characterization, which are known in the art.

Amplification products can be used for determining the sequence of a sequence of interest. For example, an amplification product comprising a sequence of interest generated by amplification methods of the invention can be subjected to sequencing by any suitable sequencing method. Suitable sequencing methods are known in the art, and include, for example, using nucleotide triphosphates that upon incorporation into a primer extension product terminates nucleotide polymerization.

Amplification products can also be used for detecting presence of and/or quantifying a nucleic acid sequence of interest in a sample. For example, presence of a nucleic acid sequence of interest in a sample can be detected by detecting the sequence of interest in amplification product resulting from amplifying polynucleotides in a sample suspected of comprising the sequence of interest. In some embodiments, a sequence of interest comprises a mutation, for example, a single nucleotide polymorphism, an insertion, a deletion or a substitution. A sequence of interest in an amplification product can be detected by any of a variety of methods known in the art, including, for example, hybridizing amplification product comprising (or suspected of comprising) the sequence of interest with a nucleic acid probe that is hybridizable to the sequence of interest. Suitable nucleic acid probes would be evident to one skilled in the art, and include, for example, probes that comprise DNA, RNA or DNA and RNA. These probes can be provided in any suitable form, including, for example, as microarrays, which may comprise the probe immobilized on a suitable substrate that can be fabricated from a material such as paper, glass, plastic, polypropylene, nylon, polyacrylamide, nitrocellulose, silicon and optical fiber. Detection of sequence of interest in an amplification product can also be achieved by methods such as limited primer extension, which are known in the art and described in, for example, U.S. Pat. Nos. 5,888,819; 6,004,744; 5,882,867; 5,710,028; 6,027,889; 6,004,745; 5,763,178; 5,011,769; 5,185,243; 4,876,187; 5,882,867; WO US88/02746; WO 99/55912; WO92/15712; WO 00/09745; WO 97/32040; WO 00/56925, and in co-pending U.S. Application Ser. No. 60/255,638, filed 13 Dec. 2000.

In one embodiment, the amplification methods of the invention are utilized to generate multiple copies of single stranded RNA products that are labeled by the incorporation of labeled nucleotides during RNA polymerization. For example, amplification according to the methods of the invention can be carried out with suitable labeled rNTPs. These labeled rNTPs can be directly attached to a label, or can comprise a moiety which could be attached to a label. The label may be attached covalently or non-covalently to the amplification products. Suitable labels are known in the art, and include, for example, a ligand which is a member of a specific binding pair which can be detected/quantified using a detectable second member of the binding pair. Thus, amplification of a target polynucleotide according to the methods of the invention in the presence of, for example, Cye3-dATP or Cye5-dATP results in the incorporation of these nucleotides into the amplification products.

The labeled amplified products are particularly suitable for analysis (for example, detection and/or quantification) by contacting them with, for example, microarrays (of any suitable surface, which includes glass, chips, plastic), beads, or particles, that comprise suitable probes such as cDNA and/or oligonucleotide probes. Thus, the invention provides methods to characterize (for example, detect and/or quantify) a sequence of interest by generating labeled RNA products using amplification methods of the invention, and analyzing the labeled products. Analysis of labeled products can be performed by, for example, of the labeled amplification products to, for example, probes immobilized at, for example, specific locations on a solid or semi-solid substrate, probes immobilized on defined particles, or probes immobilized on blots (such as a membrane), for example arrays, which have been described above. Other methods of analyzing labeled products are known in the art, such as, for example, by contacting them with a solution comprising probes, followed by extraction of complexes comprising the labeled amplification products and probes from solution. The identity of the probes provides characterization of the sequence identity of the amplified products, and thus by extrapolation the identity of the target polynucleotide present in a sample. Hybridization of the labeled products is detectable, and the amount of specific labels that are detected is proportional to the amount of the labeled amplification products of a specific sequence of interest. This measurement is useful for, for example, measuring the relative amounts of the various polynucleotide species in a sample. The amount of labeled products (as indicated by, for example, detectable signal associated with the label) hybridized at defined locations on an array can be indicative of the detection and/or quantification of the corresponding target polynucleotide species in the sample.

Determination of Gene Expression Profile

The amplification methods of the invention are particularly suitable for use in determining the levels of expression of multiple genes in a sample since the methods described herein are capable of amplifying multiple target polynucleotides (RNA as a direct target or cDNA prepared from an RNA sample), in the same sample. As described above, amplification products can be detected and quantified by various methods, as described herein and/or known in the art. Since RNA is a product of gene expression, the levels of the various RNA species, such as mRNAs, in a sample is indicative of the relative expression levels of the various genes (gene expression profile). Thus, determination of the amount of sequences of interest present in a sample, as determined by quantifying amplification products of the sequences, can provide for determination of the gene expression profile of the sample source.

The following Examples are provided to illustrate, but not limit, the invention.

EXAMPLES

Example 1

The First Transcription Module of Composite Primer-Based Methods

The general methods that are described in this example are also utilized in other examples of the first transcription module of composite primer-based methods provided herein.

Buffers

Buffers that were used throughout the composite primer-based examples are made with the following materials.

TE Buffer: 10 mM Tris-HCl, pH 8.0, 1 mM EDTA

TBE Buffer: 89 mM Tris base, 89 mM boric acid, 2 mM EDTA, pH 8.3

FX Buffer: 20 mM Tris-SO4, pH 9.0, 20 mM (NH4)2SO4, 0.1% NP-40

A First Illustration of the First Transcription Module of Amplification Methods Using a Single Composite Primer, DNA Polymerase and Rnase H Sequence amplification was performed in 15 µl reactions containing 20 mM Tris-HCl, pH 8.5, 6.0 mM MgCl2, 1.0 mM dATP, 1.0 mM dCTP, 1.0 mM dTTP, 0.8 mM dGTP, 0.2 mM dITP (dNTP's from Amersham), 0-6% DMSO, 0-8% glycerol, 0-100 ug/ml acetylated BSA (Ambion, Austin, Tex.), 0.6 Units/µl recombinant ribonuclease inhibitor (rRNasin, Promega, Madison, Wis.), 0.5-5 uM composite primer IA005, and 100-200 nM promoter-template oligonucleotide (PTO) IA015C. Composite primer IA005 is a 20-mer primer with the sequence of: ACGGAUGCGGUCUCCAGTGT (SEQ ID NO:1). Promoter-template oligonucleotide (PTO) IA015C is a 55-mer oligonucleotide with the sequence of:

ggAATTCTAATACgACTCACTATAgg-gAgAgCggTACgCTgATCAAAgATCCgTg-biotin (SEQ ID NO: 12).

Reactions were assembled with all components except the two enzymes. After heating to 70° C. or 99° C. for 10 sec. in a programmable thermal cycler (GeneAmp 9600, Perkin Elmer), the reaction mixtures were cooled down to 55° C., 60° C. or 65° C., as described in the individual examples. Upon attaining the lower temperature, 0.05-0.24 Unit of RNase H (diluted from the 5 U/µl stock solution using a diluent/storage solution: 10 mM Tris-HCl, pH 8.5, 30% glycerol; Hybridase thermostable RNase H, Epicentre Technologies, Madison, Wis.) and 1.0-5.0 Units Bca DNA polymerase (2 U/μl; Panvera, Madison, Wis.) were added. The reactions were incubated at 55° C.-65° C. for 30 minutes At the end of the incubation, reactions were cooled to 4° C. until RNA transcription step was desired.

RNA transcription was performed at 37° C. for 3 hours in 10 ul reactions containing 2.5 ul of the linear amplification reaction mixtures above, and 40 mM Tris-HCl, pH 8.5, 70 mM KCl, 5.0 mM DTT, 12 mM MgCl2, 110 μg/ml BSA, 3 mM each rNTP (ATP, UTP, CTP, GTP, Amersham), 7.5% DMSO, 1 Unit/μl rRNasin (Promega, Madison, Wis.), and 20 Units T7 RNA polymerase (Ambion, Austin, Tex.).

DNA Templates

A sequence from the J-gene region of *E. coli* K12 was chosen as a DNA template for several of the following Examples. Three DNA templates were used for these experiments: a synthetic DNA target (IA013), a primarily single-stranded DNA (351 bases) template produced by PCR amplification, and genomic DNA from the K12 strain of *E. coli* (preparation described in Example 4). Synthetic DNA target IA013 comprises:

Spacer18-
Spacer18CGGTACGCTGATCAAAGATCCGTGCAA-CAAATGTCA
TGGTCATGGTCGTGTTGAGCGCAG-CAAAACGCTGTCCGTTAAAATCCCGGCA GGGGTG-GACACTGGAGACCGCATCCGT (SEQ ID NO: 2). Spacer18 refers to polyoxyethylene spacers. These were added to the oligo in order to retard its mobility with respect to the 100-bp ssDNA product. The sequence of the aforementioned primarily single-stranded DNA (351 bases) template produced by PCR amplification is:
CGGTACGCTGATCAAAGATCCGTGCAA-
  CAAATGTCATGGTCATGGTCGTGTTGAGCGCAG
  CAAAACGCTGTCCGTTAAAATCCCG-
  GCAGGGGTGGACACTGGA GACCGCA TCCGTCT-
  TGCGG GCGAAGGTGAAGCGGGCGAGCATGGCG-
  CACCGGCAGGCGATCTGTACGTTCAGGTTCAGGT
  TAAACAGCACCCGATTTTCGAGCGT-
  GAAGGCAACAACCTGTATTGCGAAGTC-
  CCGATCAACT TCGCTATGGCGGCGCTGGGTGGC-
  GAAATCGAAGTACCGACCCTTGATGGTCGCGTCA-
  AACTG   AAAGTGCCTGGCGAAACCCAGACCGG-
  TAAGCTATTCCGTATGCG (SEQ ID NO: 3) wherein the PCR primers are bolded and underlined and the composite primers are bolded, with RNA portion in italics.

Preparation of ssDNA target from PCR amplification product

Single-stranded DNA template for amplification was prepared by. PCR amplification of a 351-bp segment of the *E. coli* J gene using the primers IA006 and IA004. Primer IA006 is a 23-mer with the sequence of: CGGTACGCTGATCAAA-gATCCGT (SEQ ID NO: 4). Primer IA004 is a 26-mer with the sequence of: CGCATACGGAATAGCTTACCGGTCT (SEQ ID NO: 5).

PCR was performed in 100 μl reactions containing 20 mM Tris-SO4, pH 9.0, 20 mM (NH4)2SO4, 0.1% NP-40, 2.0 mM MgCl2, 300 μM each dNTP (dATP, dTTP, dCTP, dGTP), 5 Units Taq DNA polymerase, 400 nM primer IA006, 400 nM 5'-phosphate-primer IA004, and 0.2 ul of a crude lysate of *E. coli* K12 strain. A modified "touchdown PCR" protocol was used with the following parameters: 95° C. for 5 seconds, 68° C. for 1 minute for 5 cycles; 94° C. for 5 seconds, 60° C. for 30 seconds, 72° C. for 1 minute for 5 cycles; 94° C. for 5 seconds, 55° C. for 30 seconds, 72° C. for 1 minute for 40 cycles; 72° C. for 15 minutes and then held indefinitely at 4° C. Primer IA004 was synthesized with a 5'-phosphate to protect the sense-strand from digestion by lambda exonuclease (Strandase kit, Novagen, Madison, Wis.). The Strandase digestion was performed according to the manufacturer's recommendation. Briefly, PCR product prepared as described above, was precipitated from the reaction mixture by the addition of 1/10 volume 3M sodium acetate, pH 5.2 and 0.6 volumes isopropanol, cooling to −20° C. for 1 hour, and centrifuged at maximum speed in a microcentrifuge for 30 minutes. The DNA pellet was washed once with 75% ethanol, then air-dried briefly before resuspension in 80 μl water. Concentration was estimated from O.D. at 260 nm, and 60 Units of lambda exonuclease (Strandase, Novagen) was added. Digestion was allowed to proceed at 37° C. for 20 minutes, reactions were then heated to 75° C. for 10 minutes, and cooled to 4° C. Incubations were performed in a programmable thermal cycler (GeneAmp 9600, Perkin Elmer). Remaining DNA was purified using QiaQuick Nucleotide Removal Columns (Qiagen, Valencia, Calif.) following the manufacturer's recommended procedure and using the buffers provided with the kit (Qiagen, Valencia Calif.). Briefly, 10 volumes of Buffer PN (Qiagen) were added to the sample. The entire volume was then applied to a Qiagen spin column and centrifuged (6000 rpm 1 minute in a microcentrifuge). The filtrate was discarded, and the column was washed twice with 500 ul of Buffer PE (Qiagen). The column was then dried thoroughly by centrifugation at maximum speed for 3 minutes. The DNA was eluted in 50 μl Buffer EB (10 mM Tris-HCl, pH 8.5) (Qiagen). The concentration was estimated to be about $2.5 \times 10^{12}$ copies/5 μl from OD at 260 nm. Gel analysis revealed that significant double stranded DNA (less than half the total) remained, but the error in concentration was less than 2-fold. The DNA was diluted to $10^{10}$ copies/5 μl in TE Buffer. Serial dilutions were prepared from the $10^{10}$ copy stock solution as needed. Concentration based on O.D. measurement was confirmed by limiting dilution PCR analysis.

Gel Electrophoresis

Amplification products were electrophoretically separated on Novex pre-cast 4-20% polyacrylamide gradient gels (Invitrogen, Carlsbad, Calif.; part no. EC62255) in 1× TBE Buffer (89 mM Tris base, 89 mM boric acid, 2 mM EDTA, pH 8.3) in a Novex electrophoresis apparatus (EI9001-XCell II Mini Cell, Novex). Reaction mixtures (5 μl) were mixed with 1 μl of 6× Gel Loading Solution (40% sucrose, 0.25% bromophenol blue, 0.25% xylene cyanole), and the entire sample was immediately loaded into each well. Gels were subjected to 250V for approximately 5 minutes, until all samples had entered the gel, and the voltage was lowered to 175V for 45 minutes. Gels were removed from between the plastic plates and stained in 0.5 ug/ml ethidium bromide in 1× TBE Buffer (89 mM Tris base, 89 mM boric acid, 2 mM EDTA, pH 8.3). A double stranded DNA molecular size marker (Hi-Lo DNA Marker, Bionexus, San Leandro, Calif.) was included in one lane of each gel run. This marker contains 16 fragments of the following sizes: 50, 100, 200, 300, 400, 500, 750, 1000, 1400, 1550, 2000, 3000, 4000, 6000, 8000, and 10000 bp. Typically, 50-2000 bp could be resolved on the gels used.

Hybridization

Oligonucleotide probes for hybridization examples (IA010 for ssDNA products; IA014 for ssRNA products) were 5'-end-labelled using T4 polynucleotide kinase (New England Biolabs, Beverly, Mass.) and γ-32P-ATP (adenosine 5'-[γ-32P] triphosphate, triethylammonium salt, Amersham, Piscataway, N.J.; PB 10218, >5000 Ci/mmol, 10 mCi/ml). Primer IA010 is a 21-mer with the sequence of: ATGTCATGGTCATGGTCGTGT (SEQ ID NO: 6). Primer IA014 is a 31-mer with the sequence of: CTCAACAC- GACCATGACCATGACATTTGTTG (SEQ ID NO: 7). Labelling reactions (50 μl total volume) contained 70 mM Tris-HCl, pH 7.6, 10 mM MgCl2, 5 mM DTT, 1 μg oligo (147 pmol for primer IA010; 101 pmol for primer IA014), 250 μCi γ-32P-ATP, and 30 Units T4 polynucleotide kinase. Incubation was at 37° C. for 30 minutes, followed by removal of unincorporated nucleotide using QIAquick Nucleotide Removal Kit (Qiagen, Valencia, Calif.). The decay rate (cpm) was determined in a Packard Minaxi Tri-Carb 4000 Series liquid scintillation counter by Cherenkov counting of 1 μl of the labeled oligo.

Hybridization was performed in 30 μl reactions. Product DNA (or RNA) (10 μl) was added to 20 μl of probe mix. Reactions contained 100 mM NaCl and 106 cpm of probe (correcting for decay using a half-life of 14.3 days). After heating to 65° C. 15 seconds, hybridization was allowed to proceed at 42° C. for 30 minutes, followed by cooling to 4° C. These steps were performed in a programmable thermal cycler with a heated cover (GeneAmp 9600, Perkin Elmer). The entire volume of hybridization reaction was electrophoresed in 10% polyacrylamide gels in 1× TBE Buffer (89 mM Tris base, 89 mM boric acid, 2 mM EDTA, pH 8.3) at 150V for 3 hours. Gels were removed from the glass plates, wrapped in plastic wrap, and exposed to autoradiography film (BioMax MR, Kodak) at −20° C. overnight (~16 hours) with two intensifying screens.

Example 2

A Second Illustration of the First Transcription Module of a Composite Primer-Based Amplification Method Amplification using a single composite primer, DNA polymerase, RNase H, and TSO or blocker was performed. Reaction mixtures containing all reaction components, as described above, as well as reaction mixtures without one of the key reagents such as composite primer, RNase H, or Bca DNA polymerase (Panvera, Madison, Wis.) were spiked with 1010 copies of synthetic ssDNA target (IA010—sequence listed in Example 1). A negative control reaction containing all the reagents and no target ssDNA, was also included. The amplification of target DNA sequence was carried out as described above. Target denaturation was carried out at 70° C. and the isothermal amplification was carried out at 65° C.

The amplification products were resolved by gel electrophoresis. No amplification products were detected in reaction mixtures without primer, RNase H or Bca DNA polymerase.

Probe IA010 hybridization and autoradiography to the ssDNA product of the linear amplification method, verified the identity of the amplification product. The linear amplification of the synthetic oligonucleotide target in this experiment was done using a non blocked promoter-template oligonucleotide (IA015b). Promoter-template oligonucleotide IA015b is a 55-mer with a sequence of:
GGAATTCTAATACGACTCACTATAGG-GAGAGCGGTACGCTGATCAAAGATCCGTG. (SEQ ID NO: 12). The standard reaction components used for this amplification reaction are as given above. The initial denaturation step was performed at 70° C. for 10 seconds. The reactions were cooled down to 65° C., and further incubated at this temperature for 30 minutes following the addition of Bca polymerase and RNase H. No hybridization was detected in the control reactions (no DNA, no primer, no RNase H, no Bca).

Example 3

Promoter Template Oligonucleotide-Based First Transcription Module of a Composite Primer-Based Amplification Method The promoter-template oligonucleotide (PTO) contains two essential sequence motifs: a T7 promoter sequence (5'-TAATACGACTCACTATAGGGAgGAG(SEQ ID NO: 8)) and a sequence complementary to the ssDNA template. Four versions of a PTO were designed (IA012, IA012b, IA015, IA015b). IA012 PTO is a 67-mer and has a sequence of:
GGAATTCTAATACGACTCACTATAGG-GAGAGATCGAGTAGCTCCGGTACGCT-GATCAAAGAT CCGTG (SEQ ID NO: 9). IA012 PTO contains two sequences in addition to the core T7 promoter: a 5'-extension (5'-GGAATTC) and a spacer (5'-ATCGAGTAGCTC(SEQ ID NO: 10)) between the promoter and the target DNA-complementary sequence. IA015 is the shorter PTO (48-mer), lacking both the 5'-extension and the spacer. IA015 PTO has the sequence of:
TAATACGACTCACTATAGGGAGAGCGG-TACGCTGATCAAAGATCCGTG(SEQ ID NO: 11). IA012b PTO is a 60-mer which contains the spacer, but not the extension. IA012b PTO has the sequence:
TAATACGACTCACTATAGGGAGAGATC-GAGTAGCTCCGGTACGCTGATCAAAGATCCGTG (SEQ ID NO: 13). IA015b contains the extension, but not the spacer. The sequence of IA015b is disclosed in Example 2. All primers other than the chimeric oligonucleotides IA005, IA019, and IA020 were synthesized by Keystone (Division of BioSource International, Camarillo, Calif.) and were PAGE purified.

The ability of IA012, IA012b, IA015, and IA015b to convert the ssDNA template into a substrate for T7 RNA polymerase was assessed by comparing the amount of RNA produced after transcription of overlap-extension products formed between a synthetic oligo product (IA009) and each of the PTO's. Synthetic oligo product IA009 is a 100-mer with the sequence of:
AGTGTCCACCCCTGCCGGGATTTTAACGGACAGCG TTTTGCTGCGCTCAACACGACCATGAC-CATGACATTTGTTGCACGGA TCTTTGATCAGCG-TACCG (SEQ ID NO: 14). Overlap-extension was performed in 15 ul reactions containing 20 mM Tris-HCl, pH 8.5, 6 mM MgCl2, 1 mM each dNTP (dATP, dTTP, dCTP, dGTP), 100 nM IA009, 100 nM PTO, and 1 Unit Bca DNA polymerase. Reactions were constituted without Bca DNA polymerase, heated to 95° C. then cooled over 10 minutes to 60° C. After addition of DNA polymerase, reactions were incubated at 60° C. for 30 minutes. A portion (2.5 μl) of the reaction mixture was added to the standard RNA transcription reaction mixture and the transcription reactions were assessed by gel electrophoresis.

Significantly more RNA was produced by the transcription substrate produced with the shorter PTO's (IA015, IA015b) than by either of IA012 or IA012b. The PTO containing the 5'-extension but not the spacer (IA015b) produced demonstrably higher yields of RNA. In all cases, however, multiple products appeared in addition to the major RNA band. A fifth PTO was designed having the same sequence as IA015b, but with a 3'-blocking group (biotin) to eliminated the free 3'-OH, to demonstrate the improved performance of a 3'-blocked PTO. Blocking the free 3'-OH of the PTO eliminates its ability to initiate non-specific incorporation of a functional promoter sequence to the amplifiction products leading to non-specific generation of transcription products. The performance of 3-blocked and unblocked PTO in the enhanced isothermal linear amplification was assessed from amplification of a synthetic oligonucleotide target, using the standard conditions. The 3'-blocked PTO (IA015c) produced comparable yields of specific RNA as IA015b, but with significantly less background. Negative control reactions (no DNA template) and reactions containing 1010 copies of oligo target (IA013) were amplified by strand displacement for 30 minutes, 1 hour, or 2 hours at 55 C, with either IA015b or IA015c included in the strand-displacement reaction. When the 3'-OH was not blocked, non-specific RNA was produced in all reactions and obscured identification of the specific RNA band. In contrast, the blocked PTO produced primarily a single RNA product.

Example 4

Amplification of a J Gene Sequence of *E. coli* Genomic DNA by the First Transcription Module of a Composite Primer-Based Amplification Method DNA was isolated from 25 ml of *E. coli* K12 (ATCC 10798) grown overnight in Tryptone-NaCl medium. Genomic DNA was isolated by lysozyme digestion and solubilization in a chaotropic lysis solution (Bactozol Kit, Molecular Research Center, Cincinnati, Ohio) following the manufacturer's recommended procedure. Briefly, bacteria were collected by centrifugation at 6000×g for 5 minutes. Cell pellets were resuspended in Bactozyme digestion buffer and incubated at 50° C. for 30 minutes. The resulting lysate was clear at the end of the digestion, without any visible clumps of undigested cells. The lysate was mixed with 4 volumes of DNazol reagent (Molecular Research Center, Cincinnati, Ohio) and incubated for 15 minutes at room temperature. DNA was precipitated from the solution by addition of 0.6 volume ice-cold ethanol. After incubation for 5 minutes at room temperature, the precipitated DNA was collected by centrifugation for 5 minutes at maximum speed in a microcentrifuge. The DNA pellet was washed with 75% ethanol, centrifuged again, and resuspended in 1.5 ml TE Buffer (10 mM Tris-HCl, pH 8.0, 1 mM EDTA) by heating at 50°-55° C. for 30 minutes, with frequent agitation. The resulting solution was passed repeatedly through a 22 gauge syringe needle to shear the DNA and reduce the viscosity of the solution. DNA was precipitated again (EPI005-35) by the addition of 1/10 volume of 5M ammonium acetate and 3 volumes ice-cold ethanol. After incubation at −20° C. for 1 hr, the DNA was collected by centrifugation at maximum speed in a microcentrifuge. The pellet was washed with 75% ethanol, centrifuged again, and resuspended in 150 µl TE Buffer. Two dilutions in TE Buffer were prepared for O.D. measurement (Beckman DU640 spectrophotometer), from which DNA concentration was calculated by assuming 50 µg/ml dsDNA produces an O.D. at 260 nm of 1. DNA concentrations of the two dilutions were 24.2 ug/10 µl and 24.6 ug/10 µl. The average of these two measurements (24.4 ug/10 µl) corresponds to approximately 2.5×109 genome copies/5 µl (5 fg of *E. coli* genomic DNA=1 copy).

DNA Amplification

DNA was serially diluted in TE Buffer to 109, 108, or 107 copies/5 ul, and denatured by heating to 95° C. for 5 minutes followed by rapid cooling on ice. Single-stranded template DNA also was diluted to 109 copies/5 ul. Reactions were assembled to contain no DNA, 107, 108, 109, or 2.5×109 copies of genomic DNA.

Amplification was performed in 15 µl reactions containing 20 mM Tris-HCl, pH 8.5, 6.0 mM MgCl2, 1.0 mM dATP, 1.0 mM dCTP, 1.0 mM dTTP, 0.8 mM dGTP, 0.2 mM dITP (dNTP's from Amersham), 6% DMSO, 8% glycerol, 100 µg/ml acetylated BSA (Ambion, Austin, Tex.), 0.6 Units/µl recombinant ribonuclease inhibitor (rRNasin, Promega, Madison, Wis.), 5 uM composite primer IA005 (sequence disclosed in Example 1), 200 nM promoter-template oligonucleotide (PTO) IA015C (sequence disclosed in Example 1). Reactions were assembled with all components except the two enzymes. After heating to 99° C. for 10 seconds in a programmable thermal cycler (GeneAmp 9600, Perkin Elmer), reactions were incubated at 60° C. for 30 minutes Upon attaining 60° C., 0.6 µl of RNase H (0.05 Units diluted from the 5 U/µl stock solution in 10 mM Tris-HCl, pH 8.5, 30% glycerol) (Hybridase, Epicentre Technologies, Madison, Wis.) and 1.0 µl Bca DNA polymerase (2.0 Units, Panvera, Madison, Wis.) were added. At the end of the 60° C. incubation, reactions were cooled to 4° C. A volume of 5.0 µl of strand-displacement product was added to each RNA transcription reaction (total volume 20 µl). RNA transcription was performed using the standard conditions and scaling up the reaction volume to 20 µl to provide sufficient material for direct gel analysis (5 µl) and probe hybridization (10 µl).

Unlike the amplification of defined single stranded synthetic target, the amplification of genomic DNA according to the composite primer-based method of the invention generally requires the formation of a defined stop for the formation of a ssDNA product with a defined 3'-end. The formation of a defined stop for primer extension can be achieved by a blocker, which hybridizes to a defined site on the target strand and can not be displaced by the polymerase. Alternatively, as in the present example, a GC rich sequence up stream of the primer site, provided a stop point for primer extension, thus leading to the formation of a ssDNA product with defined 3-end.

Amplification of a defined sequence of genomic DNA by the enhanced isothermal linear amplification method of the invention (first transcription module of a composite primer-based method) was achieved. The ssRNA product was found to hybridize to a specific oligonucleotide probe.

Example 5

Evaluation of the Effect of Composite Primer Design on the Performance of the First Transcription Module of a Composite Primer-Based Amplification Method The performance of each of the three composite primers in the first transcription module of composite primer-based amplification methods of the invention was assessed. The isothermal linear amplification was performed in 15 µl reactions containing 20 mM Tris-HCl, pH 8.5, 6.0 mM MgCl2, 1.0 mM dATP, 1.0 mM dCTP, 1.0 mM dTTP, 0.8 mM dGTP, 0.2 mM dITP (dNTP's from Amersham), 6% DMSO, 8% glycerol, 100 µg/ml acetylated BSA (Ambion, Austin, Tex.), 0.6 Units/µl recombinant ribonuclease inhibitor (rRNasin, Promega, Madison, Wis.), 5 µM composite primer, 200 nM promoter-template oligonucleotide (PTO) IA015C. The sequence of PTO IA015C is disclosed in Example 1. The sequence of composite primers IA005 (20-mer) is disclosed in Example 1. Other composite primer sequences with alpha-numerical names are as follows:

```
                                    (SEQ ID NO: 1)
    IA019    (20-mer)    ACGGAUGCGGUCUCCAGTGT (SEQ ID NO: 15)
    IA020    (21-mer)    GACGGAUGCGGUCUCCAGTGT
```

Four other composite primer sequence were used that did not have alphanumerical names. Their sequences are, respectively:

```
    (1)    GCAAGACGGAUGCGGUCUCCAGTGT    (SEQ ID NO: 16)

(2)    GACGATGCGUCTCCAGTGT          (SEQ ID NO: 17)

(3)    GACGGATGCGGUCTCCAGUGT        (SEQ ID NO: 18)

(4)    GACGGATGCGGUCTCCAGUGUCCA     (SEQ ID NO: 19)
```

These composite primers were synthesized by Dharmacon Research, Inc. (Boulder, Colo.). The RNA portion of the oligonucleotide was synthesized using a 5'-silyl protecting group in conjunction with an acid-labile 2'-orthoester protecting group (2'-bis(acetoxyethoxy)-methyl ether or "2'-ACE" (Scaringe, S. A., et al. J. Am. Chem. Soc. 120:11820-11821 (1998) and Scaringe, S. A. Advanced 5'-silyl-2'-orthoester approach to RNA oligonucleotide synthesis. Methods in Enzymology (in press)). Primers were PAGE purified.

Reactions were assembled with all components except the two enzymes. After heating to 70° C. for 10 seconds in a programmable thermal cycler (GeneAmp 9600, Perkin Elmer), reactions were cooled to 55° C.-65° C. Upon attaining the lower temperature, 0.05 Unit of RNase H (diluted from the 5 U/µl stock solution using a diluent/storage solution: 10 mM Tris-HCl, pH 8.5, 30% glycerol; Hybridase thermostable RNase H, Epicentre Technologies, Madison, Wis.) and 2.0 Units Bca DNA polymerase (2 U/µl; Panvera, Madison, Wis.) were added. The reactions were incubated at 55° C.-65° C. for 30 minutes. At the end of the incubation, reactions were cooled to 4° C. until RNA transcription. RNA transcription was performed at 37° C. for 3 hours in 10 µl reactions containing 2.5 µl of linear amplification reaction above, and 40 mM Tris-HCl, pH 8.5, 70 mM KCl, 5.0 mM DTT, 12 mM MgCl2, 110 µg/ml BSA, 3 mM each rNTP (ATP, UTP, CTP, GTP, Amersham), 7.5% DMSO, 1 Unit/µl rRNasin (Promega, Madison, Wis.), and 20 Units T7 RNA polymerase (Novagen, Madison, Wis.).

The products of the enhanced linear amplification generated with each of the composite primers were resolved by gel electrophoresis. The composite primers were designed to hybridize at the same site on the target strand, and differed by the number of deoxynucleotides at the 3'-end. The highest yield of RNA product was produced with primer IA020, followed by IA005 and IA019 equally. The other four composite primers yielded less RNA products. The optimal temperature for the isothermal linear amplification step was different for the different primers, as expected.

Example 6

Genotyping Using the First Transcription Module of a Composite Primer-Based Amplification Method and Genotype Specific Composite Primer Genomic DNA is isolated from test cells using methods described in previous examples or by other means known to the skilled artisan. Different organisms including, but not limited to, bacteria, viruses, fungi, yeast, plants, and animals are genotyped. Genotype specific primers are designed either to comprise a 3'-end nucleotide which hybridizes to one genotype of a specific nucleic acid sequence, or hybridize to the counterpart genotype. The sequence variation determining specific genotypes may be point mutation, single nucleotide polymorphism (SNP), insertions deletions and the like.

Amplification of the defined target nucleic acid sequence is carried out as described for amplification of genomic E. coli sequence, in the above example. Using the genotype specific primer and DNA polymerase which is devoid of proofreading activity, the generation of amplification product indicates the presence of target sequence of the defined genotype. Sequence variation that prevents hybridization of the 3'-end of the primer to the target nucleic acid sequence will prevent amplification. The amplification product is detected by any one of various methods for detection of single stranded nucleic acid sequence, which is known in the art. For example, the hybridization of specific labeled oligonucleotide probes to the amplification product is detected by gel electrophoresis.

In cases where the genotyping of diploid cells is required, such as the determination of homozygote or heterozygote genotype, it is feasible to carry out the amplification of the specific nucleic acid target sequence using specific primers which are designed for either the wild type and mutant genotype, or one genotype and the other genotype. The amplification reactions using the specific primers are carried out in separate reaction vessels. The detection of amplification product in only one reaction tube or less amplification product is indicative of a homozygote genotype, i.e. either wild type or mutant homozygote. The detection of amplification product in both amplification reactions indicates a heterozygote genotype.

Example 7

Genotyping Using a Composite Primer-Based Amplification Method and Genotype Specific Probe Hybridization Methods for sequencing by hybridization are described in previous examples. Determination of sequence identity by hybridization of specific probe is particularly advantageous using the isothermal method of the invention insofar as the amplification product generated by the method of the invention is single stranded and readily available to be used in hybridization of specific probes. Probes specific for a defined genotype are designed using methods known in the art. It is possible to determine hybridization criteria which will support selective probe hybridization to amplification products generated by amplification of one genotype and not the other. Sequence variation as small as a single nucleotide can prevent probe hybridization. The following factors are taken into consideration for hybridization criteria: probe length, temperature of the hybridization reaction, and buffer composition, in particular divalent ion concentration. The probes used for the analysis may be in solution, or may be attached to a solid surface. Further, the probes may be directly labeled or attached to a member of a specific binding pair and thus, able to specifically bind to another member of the specific binding pair which may be directly or indirectly labeled.

Genomic DNA is isolated from test samples by methods known in the art or as described in the above example. Test DNA is combined with the described amplification components, target-specific composite primer, and propromoter sequence (such as PTO). The combination is subjected to incubation conditions as described herein to generate single stranded RNA amplification product. Hybridization of the amplification product to genotype specific probes is carried out in solution or solid phase with attached genotype specific probes. Since the amplification products are single stranded, the products are ideally suited to be attached to a solid phase, such as glass slide, to generate an array of spatially resolved specific probes (i.e., gene chip). Alternatively, the solid phase comprises particles to which specific probes are attached. The detection of probe hybridization to the amplification products is carried out by various methods known in the art, for example, disclosed in Sambrook et al. supra. The specific probes is labeled, and the change in label spectral properties due to hybridization is detected and recorded by computer algorithms.

Particle association due to hybridization of specific probes to amplification products is also used for the detection of probe hybridization. Labeled amplification products are generated and product hybridization to probes immobilized on solid surfaces is detected and recorded by computer algorithms. The generation of labeled amplification product is carried out by incorporation of labeled rNTPs during a transcription step by substituting of one of the four rNTPs by a rNTP analog, which is labeled. The label is a dye, or a small molecule such as biotin, which is then detected by binding to specific binding entity, such as labeled streptavidin. Methods for detecting probe hybridization on solid surfaces are known in the art.

Example 8

Genotyping by rSSCP (RNA Single Stranded Conformation Polymorphism) Using a Composite Primer-Based Amplification Method Genotyping is carried out by amplification of the specific target nucleic acid sequence using a composite primer-based method described herein and by determination of the electrophoretic band pattern of the single stranded RNA product, which reflects the single stranded conformation. The use of SSCP for detection of sequence alteration is widely used. Genotype specific single stranded conformation is determined by subjecting samples to gel or capillary electrophoresis. The generation of single stranded product by amplification of target nucleic acid sequence according to the method of the invention, renders this method particularly suitable for genotype determination by combining the amplification method with rSSCP analysis.

Purified test genomic DNA is combined with components of the amplification method of the invention, as described above, and target specific composite primer and propromoter sequence, such as PTO. The combination is subjected to conditions for isothermal amplification of the target sequence. The reaction mixture containing the amplification product is subjected to either gel electrophoresis or capillary electrophoresis, using instrument and conditions known in the art. The electrophoretic band pattern of the amplification product is determined. The visualization of the oligonucleotide product is achieved by inclusion of a dye intercalator. The electrophoretic pattern of the amplification product is compared to that of amplification products generated by amplification of target nucleic acid sequence obtained from cells of known genotype. Any change in the electrophoretic mobility pattern is indicative of sequence variability. The combination of the amplification method of the invention and rSSCP provides a simple method for both the discovery of sequence polymorphism of defined target sequences, and detection of previously defined genotypes. The electrophoretic pattern of known nucleic acid sequences, or defined genotypes, can be predetermined, and the pattern generated by products of amplification of test DNA will be compared to known patterns for genotype determination.

Example 9

Amplification of *E. coli* J-Gene Target Sequence Using a Composite Primer-Based Method Linking a First and Second Transcription Module This example describes the enhanced isothermal linear amplification of a defined sequence of the J-gene of *E. coli*, followed by isothermal exponential amplification of this sequence to yield multiple copies of ssRNA.

(i) In the first example, RNA products of enhanced linear isothermal amplification were generated using three different designs of the single composite primer. The performance of each of the three composite primers in the amplification method of the invention was assessed.

The isothermal linear amplification was performed in 15 µl reactions containing 20 mM Tris-HCl, pH 8.5, 6.0 mM MgCl2, 1.0 mM dATP, 1.0 mM dCTP, 1.0 mM dTTP, 0.8 mM dGTP, 0.2 mM dITP (dNTP's from Amersham), 6% DMSO, 8% glycerol, 100 µg/ml acetylated BSA (Ambion, Austin, Tex.), 0.6 Units/µl recombinant ribonuclease inhibitor (rRNasin, Promega, Madison, Wis.), 5 µM composite primer (IA005 or IA019 or IA020), 200 nM promoter-template oligonucleotide (PTO) IA015C. All reactions had 109 copies of a 351-nucleotide single stranded DNA template. Reactions were assembled with all components except the two enzymes.

After heating at 700 C for 10 sec. in a programmable thermal cycler (GeneAmp 9600, Perkin Elmer), reactions were cooled to 550 C-650 C. The composite primer IA005 was cooled to 60° C., the composite primers IA019 and IA020 were cooled to 55° C., 60° C. and 65° C. respectively in separate reactions. Upon attaining the lower temperature, 0.05 Unit of RNase (diluted from the 5 U/µl stock solution using a diluent/storage solution: 10 mM Tris-HCl, pH 8.5, 30% glycerol; Hybridase thermostable RNaseH, Epicentre Technologies, Madison, Wis.) and 2.0 Units Bca DNA polymerase (2 U/µl; Panvera, Madison, Wis.) were added. The reactions were incubated at 550 C-650 C for 30 min. At the end of the incubation, reactions were cooled to 40 C until RNA transcription which was performed at 370 C for 3 h in 10 µl reactions containing 2.5 µl of linear amplification reaction above, and 40 mM Tris-HCl, pH 8.5, 70 mM KCl, 5.0 mM DTT, 12 mM MgCl2, 110 ugh/ml BSA, 3 mM each rNTP (ATP, UTP, CTP, GTP, Amersham), 7.5% DMSO, 1 Unit/µl rRNasin (Promega, Madison, Wis.), and 20 Units T7 RNA polymerase (Novagen, Madison, Wis.).

The products of the enhanced linear amplification generated with each of the composite primers were resolved by gel electrophoresis. The three composite primers were designed to hybridize at the same site on the target strand, and differed by the number of deoxynucleotides at the 3'-end. The highest yield of RNA product was produced with primer IA020. The optimal temperature for isothermal linear amplification step was different for the different primers, as expected. Further optimization of primer design would be expected to enhance the performance of amplification.

(ii) The product of the linear amplification produced with primer IA020, as described above was then subjected to isothermal exponential amplification.

The reaction mixture from the linear amplification described above with primer IA020 at 55° C., including the ssDNA product, was diluted 1:10, and 2.5 μl of this dilution was added to a 5 μl transcription mixture containing: 40 mM Tris-HCl, pH 8.5, 70 mM KCl, 5.0 mM DTT, 12 mM MgCl2, 110 μg/ml BSA, 3 mM each rNTP (ATP, UTP, CTP, GTP, Amersham), 7.5% DMSO, 1 Unit/μl rRNasin (Promega, Madison, Wis.), and 20 units of T7 RNA polymerase (Novagen, Madison, Wis.), dNTPs (1.0 mM dATP, 1.0 mM dCTP, 1.0 mM dTTP, 0.8 mM dGTP, 0.2 mM dITP, Amersham), MMLV-reverse transcriptase (200 U), RNaseH (0.05 U), PTO IA015c (200 nM) and primer IA024 (1 μM). The reactions were incubated at 37° C. for 0, 5, 10, 20, 40, and 60 mins., respectively. Aliquots from these time points were subjected to gel electrophoresis (5-20% polyacrylamide gel, Novex), the gel was stained with SyberGreen™ and the product bands were visualized using an imaging system. Products were clearly detectable following a 20 minute reaction.

(iii) In an effort to determine conditions for optimizing reaction efficiency, the following conditions/factors were examined:

I. The RNaseH in the above protocol was a thermostable enzyme. It was postulated that replacement of this enzyme with an *E. coli* RNaseH, which is not thermostable, and may be more active at 37° C., would improve amplification conditions.

II. Lowering the reverse transcriptase concentration for improved specificity (reduced smearing).

Reactions were set up as above with the following modifications: *E. coli* RNaseH (0.08 U) and MMLV-reverse transcriptase (25 U) were used in place of the RNaseH and reverse transcriptase in the above protocol. Two target sequences were tested using these conditions: the J gene target sequence as described above, and also a synthetic single stranded DNA target (IA009). The reactions were carried out for 60 min. at 37° C. The amplification efficiency appeared to improve under these conditions yielding more defined product bands and less overall streaking (which is indicative of high non-specific product generation).

Sequences:
The sequences used in this example are as follows:

```
composite RNA/DNA primers
                                       (SEQ ID NO: 20)
IA005    r{ACggAUgCggUCUCC} AgTgT      (20-mer)

(SEQ ID NO: 21)
IA019    r{ACggAUgCggUCUCCAg} TgT      (20-mer)

(SEQ ID NO: 22)
IA020    r{gACggAUgCggUCU} CCAgTgT     (21-mer)
```

These primers were synthesized by Dharmacon Research, Inc. (Boulder, Colo.). The RNA portion of the oligonucleotide was synthesized using a 5'-silyl protecting group in conjunction with an acid-labile 2'-orthoester protecting group (2'-bis(acetoxyethoxy)-methyl ether or "2'-ACE" (Scaringe, S A, F E Wincott, and M H Caruthers. J. Am. Chem. Soc. 120:11820-11821 (1998); and Scaringe, S A. Advanced 5'-silyl-2'-orthoester approach to RNA oligonucleotide synthesis. Methods in Enzymology (Academic Press, in press)). Oligonucleotides were purified by polyacrylamide gel electrophoresis.

All oligonucleotides other than the composite oligonucleotides were synthesized by Keystone (Division of BioSource International, Camarillo, Calif.).

PTO
IA015c (55-mer):

```
                                       (SEQ ID NO: 12)
ggAATTCTAATACgACTCACTATAgggAgAgCggTACgCTgATCAAAgAT
CGgTg-biotin J-gene target sequence (PCR nroduct from J-gene)

CggTACgCTgATCAAAgATCCgTgCAACAAATgTCATggTCATggTCgTg
                                       (SEQ ID NO: 3)
TTgAgCgCAgCAAAACgCTgTCCgTTAAAATCCCggCAggggTggACACT ggAgACCgCATCCgTCTTgCgggCgAAggTgAAgCgggCgAgCATggCgC ACCggCAggCgATCTgTACgTTCAggTTCAggTTAAACAgCACCCgATTT TCgAgCgTgAAggCAACAACCTgTATTgCgAAgTCCCgATCAACTTCgCT ATggCggCgCTgggTggCgAAATCgAAgTACCgACCCTTgATggTCgCgT CAAACTgAAAgTgCCTggCgAAACCCAgACCggTAAgCTATTCCgTATgC g
```

PCR primers are shown in bold/underlined. Chimeric primer is shown in bold, with RNA portion in italics.

Synthetic Oligo Strand-Displacement Product (IA009)
IA009 (100-mer):

```
                                       (SEQ ID NO: 23)
AgTgTCCACCCCTgCCgggATTTTAACggACAgCgTTTTgCTgCgCTCAA CACgACCATgACCATgACATTTgTTgCACggATCTTTgATCAgCgTACCg
```

Although the foregoing invention has been described in some detail by way of illustration and example for purposes of clarity of understanding, it will be apparent to those skilled in the art that certain changes and modifications may be practiced. Therefore, the descriptions and examples herein should not be construed as limiting the scope of the invention, which is delineated by the appended claims.

What is claimed is:

1. A kit comprising a first composite primer for hybridization to a target polynucleotide, wherein said composite primer comprises an RNA portion and a 3' DNA portion; a propromoter polynucleotide; and a second primer.

2. The kit of claim 1 further comprising a polynucleotide comprising a termination polynucleotide sequence.

3. The kit of claim 1 wherein the polynucleotide comprising a termination polynucleotide sequence is a template switch oligonucleotide (TSO).

4. The kit of claim 1 further comprising an enzyme which cleaves RNA from an RNA/DNA hybrid.

5. The kit of claim 4 wherein the enzyme which cleaves RNA from an RNA/DNA hybrid has RNAse H activity.

6. The kit of claim 1 further comprising an enzyme with DNA dependent DNA polymerase activity.

7. The kit of claim 1 further comprising an enzyme with RNA dependent DNA polymerase activity.

8. The kit of claim 1 further comprising one or more enzymes with all of DNA dependent DNA polymerase activity, RNA dependent DNA polymerase activity, and RNAse H activity.

9. The kit of claim 1 further comprising an RNA polymerase.

10. The kit of claim 1 wherein, in the composite primer, the RNA portion is adjacent to the DNA portion.

11. The kit of claim 1 wherein the composite primer comprises 5' and 3' DNA portions with at least one intervening RNA portion.

12. A kit comprising one or more containers comprising a first primer comprising an RNA/DNA composite primer, wherein said composite primer comprises an RNA portion and a 3' DNA portion; a propromoter polynucleotide and any two of (a) a second primer, (b) an enzyme with DNA dependent DNA polymerase activity, (c) an enzyme with RNA dependent DNA polymerase activity (d) an RNA polymerase, and (e) an enzyme which cleaves RNA from an RNA/DNA hybrid.

13. The kit of claim 1 or 12 further comprising deoxynucleoside triphosphates or ribonucleoside triphosphates.

14. The kit of claim 13 wherein a nucleoside triphosphate or a ribonucleoside triphosphate is labeled.

15. The kit of claim 1 or 12 further comprising a nucleotide analog that upon incorporation into a primer extension product effects termination of nucleotide polymerization.

16. The kit of claim 15 wherein the nucleotide analog which effects termination is labeled.

17. The kit of claim 1 or 12 wherein one or more components is provided as a dry powder.

18. A system for amplifying a sequence of interest comprising: (a) a first primer which is a composite primer, wherein said composite primer comprises an RNA portion and a 3' DNA portion, (b) a second primer, (c) a DNA dependent DNA polymerase, (d) an RNA dependent DNA polymerase, (e) a propromoter polynucleotide, (f) an RNA polymerase, and (g) an enzyme which cleaves RNA from an RNA/DNA hybrid.

19. The system of claim 18 further comprising a polynucleotide comprising a termination polynucleotide sequence.

20. The system of claim 18 wherein the DNA-dependent DNA polymerase and the RNA-dependent DNA polymerase are the same enzyme.

21. The system of claim 18 wherein the DNA-dependent DNA polymerase and enzyme that cleaves RNA from an RNA/DNA hybrid are the same enzyme.

22. The system of claim 18 wherein the RNA-dependent DNA polymerase and enzyme that cleaves RNA from an RNA/DNA hybrid are the same enzyme.

* * * * *